(12) United States Patent
Chen et al.

(10) Patent No.: US 11,274,287 B2
(45) Date of Patent: *Mar. 15, 2022

(54) ENGINEERED ALDOLASE POLYPEPTIDES AND USES THEREOF

(71) Applicant: Enzymaster (Ningbo) Bio-Engineering Co., Ltd, Ningbo (CN)

(72) Inventors: Haibin Chen, Ningbo (CN); Yong Koy Bong, Ningbo (CN); Baoqin Cai, Ningbo (CN); Qing Xu, Ningbo (CN); Tianran Shen, Ningbo (CN); Ameng Zhou, Ningbo (CN); Jiadong Yang, Ningbo (CN); Zhuhong Yang, Ningbo (CN); Yaoyao Ji, Ningbo (CN); Yingxin Zhang, Ningbo (CN)

(73) Assignee: Enzymaster (Ningbo) Bio-Engineering Co., Ltd, Ningbo (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/616,370

(22) PCT Filed: May 9, 2018

(86) PCT No.: PCT/CN2018/086228
§ 371 (c)(1),
(2) Date: Nov. 22, 2019

(87) PCT Pub. No.: WO2018/219108
PCT Pub. Date: Dec. 6, 2018

(65) Prior Publication Data
US 2020/0123525 A1    Apr. 23, 2020

(30) Foreign Application Priority Data

May 27, 2017 (CN) .......................... 201710386955.9
May 27, 2017 (CN) .......................... 201710405791.X

(51) Int. Cl.
| | | |
|---|---|---|
| C12P 13/04 | (2006.01) | |
| C12N 9/88 | (2006.01) | |
| C12N 9/16 | (2006.01) | |
| C07K 17/00 | (2006.01) | |

(52) U.S. Cl.
CPC ................ *C12N 9/88* (2013.01); *C07K 17/00* (2013.01); *C12P 13/04* (2013.01); *C12Y 401/02048* (2013.01)

(58) Field of Classification Search
CPC ........... C12P 19/40; C12P 13/04; C12P 5/005; C12N 15/52; C12N 9/0006; C12N 15/70; C12N 9/0008; C12Y 301/01; C12Y 402/01
USPC .... 435/189, 92, 121, 106, 138, 320.1, 252.3
See application file for complete search history.

(56) References Cited

PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
NCBI Reference Sequence: BAD91544.1, "phenylserine aldolase [Pseudomonas putida]", GenBank (Aug. 10, 2005).
NCBI Reference Sequence: WP_057714849.1, "low specificity L-threonine aldolase [Pseudomonas fluoresens]", GenBank (May 15, 2017).
Dückers, N. et al., "Threonine Aldolases-Screening, Properties, and Applications in the Synthesis of Non-Proteinogenic Beta-Hydroxy-Alpha-Amino Acids", Appl. Microbiol. Biotechnol., vol. 88, pp. 409-424 (Aug. 2010).
Han, Y. Y. et al., "Synthesis of p-Methylsulfonylphenylserine Copper", Chem. Ind. & Eng., vol. 28. No. 2, pp. 29-34 (Mar. 2011).
Kimura, T. et al., "Enzymatic Synthesis of Beta-Hydroxy-Alpha-Amino Acids Based on Recombinant D-and L-Threonine Aldolases", J. Am. Chem. Soc., vol. 119, p. 11734-11742 (1997).
Liu, J et al., "Diversity of Microbial Threonine Aldolases and their Application", J. Mol. Cat. B: Enzym., vol. 10, pp. 107-115 (2000).

\* cited by examiner

*Primary Examiner* — Robert B Mondesi
*Assistant Examiner* — Mohammad Y Meah
(74) *Attorney, Agent, or Firm* — Smith Patent, LLC; Chalin A. Smith

(57) ABSTRACT

The present invention provides engineered polypeptides that are useful for the asymmetric synthesis of β-hydroxy-α-amino acids under industrial-relevant conditions. The present disclosure also provides polynucleotides encoding engineered polypeptides, host cells capable of expressing engineered polypeptides, and methods of producing β-hydroxy-α-amino acids using engineered polypeptides. Compared to other processes of preparation, the use of the engineered polypeptides of the present invention for the preparation of β-hydroxy-α-amino acids results in high purity of the desired stereoisomers, mild reaction conditions, low pollution and low energy consumption. So, it has good industrial application prospects.

20 Claims, No Drawings
Specification includes a Sequence Listing.

SEQUENCE LISTING

```
<160> NUMBER OF SEQ ID NOS: 216

<210> SEQ ID NO 1
<211> LENGTH: 1071
<212> TYPE: DNA
<213> ORGANISM: Artificial sequence
<220> FEATURE:
<223> OTHER INFORMATION: Engineered sequence

<400> SEQUENCE: 1
atgaacggtg aaacctcgcg tccgccggcg ctgggtttta gctctgataa tattgctggt      60
gcaagcccgg aagtcgcaca ggcactggtg aaacatagtt ccggccaagc gggtccgtat     120
ggcaccgatg aactgacggc ccaggtgaaa cgtaaatttt gcgaaatctt cgaacgcgac     180
gtcgaagtgt tcctggttcc gaccggtacg gcagcaaacg cactgtgtct gtccgcaatg     240
accccgccgt ggggtaatat ttactgccat ccggcgtccc acatcaacaa tgatgaatgt     300
ggtgcgccgg aattttttctc aaacggcgcc aaactgatga ccgttgatgg tccggcagct     360
aaactggaca ttgtccgtct gcgcgaacgt acgcgcgaaa aagtgggtga tgttcatacc     420
acgcagccgg catgcgtctc tattacccaa gctacggaag tgggcagtat ctataccctg     480
gatgaaattg aagccatcgg tgacgtgtgc aaatcatcga gcctgggtct gcacatggat     540
ggctctcgtt ttgctaatgc gctggtgtcc ctgggctgtt caccggcaga aatgacctgg     600
aaagccggtg ttgacgcact gagttttggt gcgacgaaaa acggcgttct ggcggccgaa     660
gcaattgtcc tgttcaatac ctcgctggct acggaaatga gctatcgtcg caaacgtgcc     720
ggccacctgt ctagtaaaat gcgctttctg agcgctcaga tcgatgcgta cctgaccgat     780
gacctgtggc tgcgtaacgc ccgcaaagca aatgcagctg cgcagcgtct ggcccaaggt     840
ctggaaggcc tgggcggtgt tgaagtcctg ggcggtaccg aagcaaacat tctgttctgt     900
cgcctggatt ctgccatgat cgacgcactg ctgaaagctg gctttggttt ctaccatgat     960 cgttgggggtc cgaacgtggt tcgctttgtt accagcttcg ctaccacggc ggaagatgtg    1020
gaccacctgc tgaatcaggt tcgcctggcc gcagaccgta cgcaagaacg c              1071

<210> SEQ ID NO 2
<211> LENGTH: 357
<212> TYPE: PRT
<213> ORGANISM: Pseudomonas putida

<400> SEQUENCE: 2

Met Asn Gly Glu Thr Ser Arg Pro Pro Ala Leu Gly Phe Ser Ser Asp
 1               5                  10                  15

Asn Ile Ala Gly Ala Ser Pro Glu Val Ala Gln Ala Leu Val Lys His
            20                  25                  30
```

Ser Ser Gly Gln Ala Gly Pro Tyr Gly Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 3
<211> LENGTH: 1128
<212> TYPE: DNA
<213> ORGANISM: Artificial sequence
<220> FEATURE:
<223> OTHER INFORMATION: Engineered sequence

<400> SEQUENCE: 3
atgaacggtg aaacctcgcg tccgccggcg ctgggttta gctctgataa tattgctggt      60
gcaagcccgg aagtcgcaca ggcactcgtt aagcacagtt cgggccaggc gggtccctat    120
ggcaccgacg agttgacggc acaggtcaag catagctccg ccaagctgg accttatggt    180

```
acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccct gctggctacg gaaatgagct atcgtcgcaa acgtgccggc    780
cacctgtcta gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 4
<211> LENGTH: 376
<212> TYPE: PRT
<213> ORGANISM: Artificial sequence
<220> FEATURE:
<223> OTHER INFORMATION: Engineered sequence
<400> SEQUENCE: 4

```
Met Asn Gly Glu Thr Ser Arg Pro Pro Ala Leu Gly Phe Ser Ser Asp
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190
```

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 5
<211> LENGTH: 1128
<212> TYPE: DNA
<213> ORGANISM: Artificial sequence
<220> FEATURE:
<223> OTHER INFORMATION: Engineered sequence

<400> SEQUENCE: 5

```
atgaacggtg aaacctcgcg tccgccggcg ctgggtttta gctctgataa tattgctggt     60
gcaagcccgg aagtcgcaca ggcactcgtt aagcacagtt cgggccagcc gggtccctat    120
ggcaccgacg agttgacggc acaggtcaag catagctccg ccaagctgg accttatggt     180 acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatatttta ctgccatccg cgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta tacgctggat    540
gaaattgaag ccatcggtga cgtgtgcaaa tcatcgagcc tggtctgca catggatggc    600 tctcgttttg ctaatgcgct ggtgtccctg gctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgtcta gtaaaatgcg cttttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggttttcta tcatgatcgt   1020
```

```
tggggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 6
<211> LENGTH: 376
<212> TYPE: PRT
<213> ORGANISM: Artificial sequence
<220> FEATURE:
<223> OTHER INFORMATION: Engineered sequence

<400> SEQUENCE: 6

| | | | | | | | | | | | | | | |
|---|---|---|---|---|---|---|---|---|---|---|---|---|---|---|
| Met | Asn | Gly | Glu | Thr | Ser | Arg | Pro | Pro | Ala | Leu | Gly | Phe | Ser | Ser | Asp |
| 1 | | | | 5 | | | | | 10 | | | | | 15 | |
| Asn | Ile | Ala | Gly | Ala | Ser | Pro | Glu | Val | Ala | Gln | Ala | Leu | Val | Lys | His |
| | | | 20 | | | | | 25 | | | | | 30 | | |
| Ser | Ser | Gly | Gln | Pro | Gly | Pro | Tyr | Gly | Thr | Asp | Glu | Leu | Thr | Ala | Gln |
| | | 35 | | | | | 40 | | | | | 45 | | | |
| Val | Lys | His | Ser | Ser | Gly | Gln | Ala | Gly | Pro | Tyr | Gly | Thr | Asp | Glu | Leu |
| | 50 | | | | | 55 | | | | | 60 | | | | |
| Thr | Ala | Gln | Val | Lys | Arg | Lys | Phe | Cys | Glu | Ile | Phe | Glu | Arg | Asp | Val |
| 65 | | | | | 70 | | | | | 75 | | | | | 80 |
| Glu | Val | Phe | Leu | Val | Pro | Thr | Gly | Thr | Ala | Ala | Asn | Ala | Leu | Cys | Leu |
| | | | | 85 | | | | | 90 | | | | | 95 | |
| Ser | Ala | Met | Thr | Pro | Pro | Trp | Gly | Asn | Ile | Tyr | Cys | His | Pro | Ala | Ser |
| | | | 100 | | | | | 105 | | | | | 110 | | |
| His | Ile | Asn | Asn | Asp | Glu | Cys | Gly | Ala | Pro | Glu | Phe | Phe | Ser | Asn | Gly |
| | | 115 | | | | | 120 | | | | | 125 | | | |
| Ala | Lys | Leu | Met | Thr | Val | Asp | Gly | Pro | Ala | Ala | Lys | Leu | Asp | Ile | Val |
| | 130 | | | | | 135 | | | | | 140 | | | | |
| Arg | Leu | Arg | Glu | Arg | Thr | Arg | Glu | Lys | Val | Gly | Asp | Val | His | Thr | Thr |
| 145 | | | | | 150 | | | | | 155 | | | | | 160 |
| Gln | Pro | Ala | Cys | Val | Ser | Ile | Thr | Gln | Ala | Thr | Glu | Val | Gly | Ser | Ile |
| | | | | 165 | | | | | 170 | | | | | 175 | |
| Tyr | Thr | Leu | Asp | Glu | Ile | Glu | Ala | Ile | Gly | Asp | Val | Cys | Lys | Ser | Ser |
| | | | 180 | | | | | 185 | | | | | 190 | | |
| Ser | Leu | Gly | Leu | His | Met | Asp | Gly | Ser | Arg | Phe | Ala | Asn | Ala | Leu | Val |
| | | 195 | | | | | 200 | | | | | 205 | | | |
| Ser | Leu | Gly | Cys | Ser | Pro | Ala | Glu | Met | Thr | Trp | Lys | Ala | Gly | Val | Asp |
| | 210 | | | | | 215 | | | | | 220 | | | | |
| Ala | Leu | Ser | Phe | Gly | Ala | Thr | Lys | Asn | Gly | Val | Leu | Ala | Ala | Glu | Ala |
| 225 | | | | | 230 | | | | | 235 | | | | | 240 |
| Ile | Val | Leu | Phe | Asn | Thr | Ser | Leu | Ala | Thr | Glu | Met | Ser | Tyr | Arg | Arg |
| | | | | 245 | | | | | 250 | | | | | 255 | |
| Lys | Arg | Ala | Gly | His | Leu | Ser | Ser | Lys | Met | Arg | Phe | Leu | Ser | Ala | Gln |
| | | | 260 | | | | | 265 | | | | | 270 | | |
| Ile | Asp | Ala | Tyr | Leu | Thr | Asp | Asp | Leu | Trp | Leu | Arg | Asn | Ala | Arg | Lys |
| | | 275 | | | | | 280 | | | | | 285 | | | |
| Ala | Asn | Ala | Ala | Ala | Gln | Arg | Leu | Ala | Gln | Gly | Leu | Glu | Gly | Leu | Gly |
| | 290 | | | | | 295 | | | | | 300 | | | | |
| Gly | Val | Glu | Val | Leu | Gly | Gly | Thr | Glu | Ala | Asn | Ile | Leu | Phe | Cys | Arg |
| 305 | | | | | 310 | | | | | 315 | | | | | 320 |
| Leu | Asp | Ser | Ala | Met | Ile | Asp | Ala | Leu | Leu | Lys | Ala | Gly | Phe | Gly | Phe |
| | | | | 325 | | | | | 330 | | | | | 335 | |
| Tyr | His | Asp | Arg | Trp | Gly | Pro | Asn | Val | Val | Arg | Phe | Val | Thr | Ser | Phe |

```
              340             345             350
Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 7
<211> LENGTH: 1128
<212> TYPE: DNA
<213> ORGANISM: Artificial sequence
<220> FEATURE:
<223> OTHER INFORMATION: Engineered sequence

<400> SEQUENCE: 7
atgaacggtg aaacctcgcg tccgccggcg ctgggtttta gctctgataa tattgctggt      60
gcaagcccgg aagtcgcaca ggcactcgtt aagcacagtt cgggccaggc gtttccctat     120
ggcaccgacg agttgacggc acaggtcaag catagctccg ccaagctgga accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa cgtgccggc     780 cacctgtcta gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg cggtgttga agtcctgggc ggtaccgaag caaacattct gttctgtcgc     960
ctggattctg ccatgatcga cgcactgctg aaagctggct ttggtttcta tcatgatcgt    1020
tggggtccga acgtggttcg ctttgttacc agcttcgcta ccacggcgga agatgtggac    1080
cacctgctga atcaggttcg cctggccgca gaccgtacgc aagaacgc                 1128

<210> SEQ ID NO 8
<211> LENGTH: 376
<212> TYPE: PRT
<213> ORGANISM: Artificial sequence
<220> FEATURE:
<223> OTHER INFORMATION: Engineered sequence

<400> SEQUENCE: 8
```

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Phe Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val

```
                65                  70                  75                  80
            Glu Val Phe Leu Val Pro Thr Gly Thr Ala Ala Asn Ala Leu Cys Leu
                            85                  90                  95

Ser Ala Met Thr Pro Pro Trp Gly Asn Ile Tyr Cys His Pro Ala Ser
                           100                 105                 110

His Ile Asn Asn Asp Glu Cys Gly Ala Pro Glu Phe Phe Ser Asn Gly
                           115                 120                 125

Ala Lys Leu Met Thr Val Asp Gly Pro Ala Ala Lys Leu Asp Ile Val
                       130                 135                 140

Arg Leu Arg Glu Arg Thr Arg Glu Lys Val Gly Asp Val His Thr Thr
            145                 150                 155                 160

Gln Pro Ala Cys Val Ser Ile Thr Gln Ala Thr Glu Val Gly Ser Ile
                           165                 170                 175

Tyr Thr Leu Asp Glu Ile Glu Ala Ile Gly Asp Val Cys Lys Ser Ser
                       180                 185                 190

Ser Leu Gly Leu His Met Asp Gly Ser Arg Phe Ala Asn Ala Leu Val
                       195                 200                 205

Ser Leu Gly Cys Ser Pro Ala Glu Met Thr Trp Lys Ala Gly Val Asp
                       210                 215                 220

Ala Leu Ser Phe Gly Ala Thr Lys Asn Gly Val Leu Ala Ala Glu Ala
            225                 230                 235                 240

Ile Val Leu Phe Asn Thr Ser Leu Ala Thr Glu Met Ser Tyr Arg Arg
                           245                 250                 255

Lys Arg Ala Gly His Leu Ser Ser Lys Met Arg Phe Leu Ser Ala Gln
                           260                 265                 270

Ile Asp Ala Tyr Leu Thr Asp Leu Trp Leu Arg Asn Ala Arg Lys
                       275                 280                 285

Ala Asn Ala Ala Ala Gln Arg Leu Ala Gln Gly Leu Glu Gly Leu Gly
                       290                 295                 300

Gly Val Glu Val Leu Gly Gly Thr Glu Ala Asn Ile Leu Phe Cys Arg
            305                 310                 315                 320

Leu Asp Ser Ala Met Ile Asp Ala Leu Leu Lys Ala Gly Phe Gly Phe
                           325                 330                 335

Tyr His Asp Arg Trp Gly Pro Asn Val Val Arg Phe Val Thr Ser Phe
                       340                 345                 350

Ala Thr Thr Ala Glu Asp Val Asp His Leu Leu Asn Gln Val Arg Leu
                       355                 360                 365

Ala Ala Asp Arg Thr Gln Glu Arg
                       370                 375

<210> SEQ ID NO 9
<211> LENGTH: 1128
<212> TYPE: DNA
<213> ORGANISM: Artificial sequence
<220> FEATURE:
<223> OTHER INFORMATION: Engineered sequence

<400> SEQUENCE: 9
atgaacggtg aaacctcgcg tccgccggcg ctgggtttta gctctgataa tattgctggt      60
gcaagcccgg aagtcgcaca ggcactcgtt aagcacagtt cgggccaggc gtatccctat     120
ggcaccgacg agttgacggc acaggtcaag catagctccg ccaagctgg accttatggt     180 acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
```

```
ccgccgtggg gtaatattta ctgccatccg cgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccctc gctggctacg gaaatgagct atcgtcgcaa acgtgccggc    780
cacctgtcta gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 10
<211> LENGTH: 376
<212> TYPE: PRT
<213> ORGANISM: Artificial sequence
<220> FEATURE:
<223> OTHER INFORMATION: Engineered sequence

<400> SEQUENCE: 10

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Tyr Pro Tyr Gly Thr Asp Glu Leu Thr Ala Gln
            35                  40                  45

Val Lys His Ser Ser Gly Gln Ala Gly Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
        210                 215                 220
```

```
Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 11
<211> LENGTH: 1128
<212> TYPE: DNA
<213> ORGANISM: Artificial sequence
<220> FEATURE:
<223> OTHER INFORMATION: Engineered sequence

<400> SEQUENCE: 11
atgaacggtg aaacctcgcg tccgccggcg ctgggttttta gctctgataa tattgctggt     60
gcaagcccgg aagtcgcaca ggcactcgtt aagcacagtt cgggccaggc ggatccctat    120
ggcaccgacg agttgacggc acaggtcaag catagctccg ccaagctgg accttatggt     180 acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta tacctggat   540 gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa cgtgccggc    780 cacctgtcta gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

```
<210> SEQ ID NO 12
<211> LENGTH: 376
<212> TYPE: PRT
<213> ORGANISM: Artificial sequence
<220> FEATURE:
<223> OTHER INFORMATION: Engineered sequence

<400> SEQUENCE: 12

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Asp Pro Tyr Gly Thr Asp Glu Leu Thr Ala Gln
            35                  40                  45

Val Lys His Ser Ser Gly Gln Ala Gly Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365
```

Ala Ala Asp Arg Thr Gln Glu Arg
        370                 375

<210> SEQ ID NO 13
<211> LENGTH: 1128
<212> TYPE: DNA
<213> ORGANISM: Artificial sequence
<220> FEATURE:
<223> OTHER INFORMATION: Engineered sequence

<400> SEQUENCE: 13

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcccggacg agttgacggc acaggtcaag catagctccg gccaagctgg accttatggt   180
acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg cgttctggc ggccgaagca   720
attgtcctgt caataccctc gctggctacg gaaatgagct atcgtcgcaa acgtgccggc   780
cacctgtcta gtaaaatgcg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcta tcatgatcgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 14
<211> LENGTH: 376
<212> TYPE: PRT
<213> ORGANISM: Artificial sequence
<220> FEATURE:
<223> OTHER INFORMATION: Engineered sequence

<400> SEQUENCE: 14

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Pro Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

```
Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 15
<211> LENGTH: 1128
<212> TYPE: DNA
<213> ORGANISM: Artificial sequence
<220> FEATURE:
<223> OTHER INFORMATION: Engineered sequence

<400> SEQUENCE: 15
atgaacggtg aaacctcgcg tccgccggcg ctgggtttta gctctgataa tattgctggt      60
gcaagcccgg aagtcgcaca ggcactcgtt aagcacagtt cgggccaggc gggtccctat    120
ggcaccgtgg agttgacggc acaggtcaag catagctccg ccaagctgg accttatggt     180 acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
```

```
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg gctgttcac cggcagaaat gacctggaaa     660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgtcta gtaaaatgcg cttctctgagc gctcagatcg atgcgtacct gaccgatgac   840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 16
<211> LENGTH: 376
<212> TYPE: PRT
<213> ORGANISM: Artificial sequence
<220> FEATURE:
<223> OTHER INFORMATION: Engineered sequence

<400> SEQUENCE: 16

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Val Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
```

|     |     |     |     |     | 245 |     |     |     |     | 250 |     |     |     |     | 255 |     |     |
| --- | --- | --- | --- | --- | --- | --- | --- | --- | --- | --- | --- | --- | --- | --- | --- | --- | --- |
| Lys | Arg | Ala | Gly | His | Leu | Ser | Ser | Lys | Met | Arg | Phe | Leu | Ser | Ala | Gln |     |     |
|     |     |     | 260 |     |     |     |     | 265 |     |     |     |     | 270 |     |     |     |     |

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 17
<211> LENGTH: 1128
<212> TYPE: DNA
<213> ORGANISM: Artificial sequence
<220> FEATURE:
<223> OTHER INFORMATION: Engineered sequence

<400> SEQUENCE: 17

```
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatttt actgccatcc ggcgtcccac atcaacaatg atgaatgtggt    360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct cgctggctac gaaatgagtc atcgtcgcaa acgtgccggc     780
cacctgtcta gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgtgc ggtaccgaag caaacattct gttctgtcgc     960
ctggattctg ccatgatcga cgcactgctg aaagctggct ttggtttcta tcatgatcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 18
<211> LENGTH: 376
<212> TYPE: PRT
<213> ORGANISM: Artificial sequence -continued
<220> FEATURE:
<223> OTHER INFORMATION: Engineered sequence

<400> SEQUENCE: 18

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Cys Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 19

<211> LENGTH: 1128
<212> TYPE: DNA
<213> ORGANISM: Artificial sequence
<220> FEATURE:
<223> OTHER INFORMATION: Engineered sequence

<400> SEQUENCE: 19

| | | |
|---|---|---|
| atgaacggtg aaacctcgcg tccgccggcg ctgggtttta gctctgataa tattgctggt | 60 |
| gcaagcccgg aagtcgcaca ggcactcgtt aagcacagtt cgggccaggc gggtccctat | 120 |
| ggcaccgacg agttgacggc acaggtcaag catagctccg gccaagctgg accttatggt | 180 |
| acagatgaac tgactgctca agttaaacgt aaattttgcg aaatcttcga acgcgacgtc | 240 |
| gaagtgttcc tggttccgac cggtacggca gcaaacgcac tgtgtctgtc cgcaatgacc | 300 |
| ccgccgtggg gtaatattta ctgccatccg gcgtcccaca tcaacaatga tgaatgtggt | 360 |
| gcgccggaat ttttctcaaa cggcgccaaa ctgatgaccg ttgatggtcc ggcagctaaa | 420 |
| ctggacattg tccgtctgcg cgaacgtacg cgcgaaaaag tgggtgatgt tcataccacg | 480 |
| cagccggcat gcgtctctat tacccaagct acggaagtgg gcagtatcta taccctggat | 540 |
| gaaattgaag ccatcggtga cgtgtgcaaa tcatcgagcc tgggtctgca catggatggc | 600 |
| tctcgttttg ctaatgcgct ggtgtccctg gctgttcac cggcagaaat gacctggaaa | 660 |
| gccggtgttg acgcactgag ttttggtgcg acgaaaaacg cgttctggc ggccgaagca | 720 |
| attgtcctgt tcaataccte gctggctacg gaaatgagct atcgtcgcaa cgtgccggc | 780 |
| cacctgtcta gtaaaatgcg ctttctgagc gctcagatcg atgcgtacct gaccgatgac | 840 |
| ctgtggctgc gtaacgcccg caaagcaaat gcagctgcgc agcgtctggc ccaaggtctg | 900 |
| gaaggcctgg gcggtgttga agtcctgggc ggtaccgaag caaacattct gttctgtcgc | 960 |
| ctggattctg ccatgatcga agcactgctg aaagctggct tggtttcta tcatgatcgt | 1020 |
| tggggtccga acgtggttcg ctttgttacc agcttcgcta ccacggcgga agatgtggac | 1080 |
| cacctgctga atcaggttcg cctggccgca gaccgtacgc aagaacgc | 1128 |

<210> SEQ ID NO 20
<211> LENGTH: 376
<212> TYPE: PRT
<213> ORGANISM: Artificial sequence
<220> FEATURE:
<223> OTHER INFORMATION: Engineered sequence

<400> SEQUENCE: 20

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

```
Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Glu Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 21
<211> LENGTH: 1128
<212> TYPE: DNA
<213> ORGANISM: Artificial sequence
<220> FEATURE:
<223> OTHER INFORMATION: Engineered sequence

<400> SEQUENCE: 21
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgg accttatggt      180 aacgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatttta ctgccatccg gcgtcccaca tcaacaatga tgaatgtggt    360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat taccaagct acgaagtgg gcagtatcta taccctggat      540
gaaattgaag ccatcggtga cgtgtgcaaa tcatcgagcc tgggtctgca catggatggc    600
```

```
tctcgttttg ctaatgcgct ggtgtccctg ggctgttcac cggcagaaat gacctggaaa      660
gccggtgttg acgcactgag ttttggtgcg acgaaaaacg gcgttctggc ggccgaagca      720
attgtcctgt tcaataccte gctggctacg gaaatgagct atcgtcgcaa acgtgccggc      780
cacctgtcta gtaaaatgcg cttttctgagc gctcagatcg atgcgtacct gaccgatgac    840
ctgtggctgc gtaacgcccg caaagcaaat gcagctgcgc agcgtctggc ccaaggtctg      900
gaaggcctgg gcggtgttga agtcctgggc ggtaccgaag caaacattct gttctgtcgc      960
ctggattctg ccatgatcga cgcactgctg aaagctggct ttggtttcta tcatgatcgt     1020
tggggtccga acgtggttcg ctttgttacc agcttcgcta ccacggcgga agatgtggac     1080
cacctgctga atcaggttcg cctggccgca gaccgtacgc aagaacgc                  1128
```

<210> SEQ ID NO 22
<211> LENGTH: 376
<212> TYPE: PRT
<213> ORGANISM: Artificial sequence
<220> FEATURE:
<223> OTHER INFORMATION: Engineered sequence

<400> SEQUENCE: 22

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Asn Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270
```

```
Ile Asp Ala Tyr Leu Thr Asp Leu Trp Leu Arg Asn Ala Arg Lys
        275                 280                 285

Ala Asn Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 23
<211> LENGTH: 1128
<212> TYPE: DNA
<213> ORGANISM: Artificial sequence
<220> FEATURE:
<223> OTHER INFORMATION: Engineered sequence

<400> SEQUENCE: 23
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
aaagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg cgttctggc ggccgaagca     720
attgtcctgt caataccctc gctggctacg gaaatgagct atcgtcgcaa cgtgccggc      780
cacctgtcta gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcgttgttga gtcctgggc ggtaccgaag caaacattct gttctgtcgc     960
ctggattctg ccatgatcga cgcactgctg aaagctggct ttggtttcta tcatgatcgt    1020
tggggtccga acgtggttcg ctttgttacc agcttcgcta ccacggcgga agatgtggac    1080
cacctgctga atcaggttcg cctggccgca gaccgtacgc aagaacgc              1128

<210> SEQ ID NO 24
<211> LENGTH: 376
<212> TYPE: PRT
<213> ORGANISM: Artificial sequence
<220> FEATURE:
<223> OTHER INFORMATION: Engineered sequence

<400> SEQUENCE: 24
```

```
Met Asn Gly Glu Thr Ser Arg Pro Pro Ala Leu Gly Phe Ser Ser Asp
1               5                   10                  15
Asn Ile Ala Gly Ala Ser Pro Glu Val Ala Gln Ala Leu Val Lys His
            20                  25                  30
Ser Ser Gly Gln Ala Gly Pro Tyr Gly Thr Asp Glu Leu Thr Ala Gln
        35                  40                  45
Val Lys His Ser Ser Gly Gln Ala Gly Pro Tyr Gly Lys Asp Glu Leu
50                  55                  60
Thr Ala Gln Val Lys Arg Lys Phe Cys Glu Ile Phe Glu Arg Asp Val
65                  70                  75                  80
Glu Val Phe Leu Val Pro Thr Gly Thr Ala Ala Asn Ala Leu Cys Leu
                85                  90                  95
Ser Ala Met Thr Pro Pro Trp Gly Asn Ile Tyr Cys His Pro Ala Ser
            100                 105                 110
His Ile Asn Asn Asp Glu Cys Gly Ala Pro Glu Phe Phe Ser Asn Gly
        115                 120                 125
Ala Lys Leu Met Thr Val Asp Gly Pro Ala Ala Lys Leu Asp Ile Val
130                 135                 140
Arg Leu Arg Glu Arg Thr Arg Glu Lys Val Gly Asp Val His Thr Thr
145                 150                 155                 160
Gln Pro Ala Cys Val Ser Ile Thr Gln Ala Thr Glu Val Gly Ser Ile
                165                 170                 175
Tyr Thr Leu Asp Glu Ile Glu Ala Ile Gly Asp Val Cys Lys Ser Ser
            180                 185                 190
Ser Leu Gly Leu His Met Asp Gly Ser Arg Phe Ala Asn Ala Leu Val
        195                 200                 205
Ser Leu Gly Cys Ser Pro Ala Glu Met Thr Trp Lys Ala Gly Val Asp
210                 215                 220
Ala Leu Ser Phe Gly Ala Thr Lys Asn Gly Val Leu Ala Ala Glu Ala
225                 230                 235                 240
Ile Val Leu Phe Asn Thr Ser Leu Ala Thr Glu Met Ser Tyr Arg Arg
                245                 250                 255
Lys Arg Ala Gly His Leu Ser Ser Lys Met Arg Phe Leu Ser Ala Gln
            260                 265                 270
Ile Asp Ala Tyr Leu Thr Asp Asp Leu Trp Leu Arg Asn Ala Arg Lys
        275                 280                 285
Ala Asn Ala Ala Ala Gln Arg Leu Ala Gln Gly Leu Glu Gly Leu Gly
290                 295                 300
Gly Val Glu Val Leu Gly Gly Thr Glu Ala Asn Ile Leu Phe Cys Arg
305                 310                 315                 320
Leu Asp Ser Ala Met Ile Asp Ala Leu Leu Lys Ala Gly Phe Gly Phe
                325                 330                 335
Tyr His Asp Arg Trp Gly Pro Asn Val Val Arg Phe Val Thr Ser Phe
            340                 345                 350
Ala Thr Thr Ala Glu Asp Val Asp His Leu Leu Asn Gln Val Arg Leu
        355                 360                 365
Ala Ala Asp Arg Thr Gln Glu Arg
370                 375

<210> SEQ ID NO 25
<211> LENGTH: 1128
<212> TYPE: DNA
<213> ORGANISM: Artificial sequence
<220> FEATURE:
<223> OTHER INFORMATION: Engineered sequence
```

<400> SEQUENCE: 25

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg gccaagctgg accttatggt   180
catgatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta tccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaatacctc gctggctacg gaaatgagct atcgtcgcaa cgtgccggc    780
cacctgtcta gtaaaatgcg cttctgagc gctcagatcg atgcgtacct gaccgatgac    840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcta tcatgatcgt  1020
tggggtccga acgtggttcg ctttgttacc agcttcgcta ccacggcgga agatgtggac  1080
cacctgctga atcaggttcg cctggccgca gaccgtacgc aagaacgc               1128
```

<210> SEQ ID NO 26  
<211> LENGTH: 376  
<212> TYPE: PRT  
<213> ORGANISM: Artificial sequence  
<220> FEATURE:  
<223> OTHER INFORMATION: Engineered sequence

<400> SEQUENCE: 26

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Gly Pro Tyr Gly His Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
```

```
            145                 150                 155                 160
        Gln Pro Ala Cys Val Ser Ile Thr Gln Ala Thr Glu Val Gly Ser Ile
                        165                 170                 175
        Tyr Thr Leu Asp Glu Ile Glu Ala Ile Gly Asp Val Cys Lys Ser Ser
                        180                 185                 190
        Ser Leu Gly Leu His Met Asp Gly Ser Arg Phe Ala Asn Ala Leu Val
                        195                 200                 205
        Ser Leu Gly Cys Ser Pro Ala Glu Met Thr Trp Lys Ala Gly Val Asp
                        210                 215                 220
        Ala Leu Ser Phe Gly Ala Thr Lys Asn Gly Val Leu Ala Ala Glu Ala
        225                 230                 235                 240
        Ile Val Leu Phe Asn Thr Ser Leu Ala Thr Glu Met Ser Tyr Arg Arg
                        245                 250                 255
        Lys Arg Ala Gly His Leu Ser Ser Lys Met Arg Phe Leu Ser Ala Gln
                        260                 265                 270
        Ile Asp Ala Tyr Leu Thr Asp Asp Leu Trp Leu Arg Asn Ala Arg Lys
                        275                 280                 285
        Ala Asn Ala Ala Ala Gln Arg Leu Ala Gln Gly Leu Glu Gly Leu Gly
                        290                 295                 300
        Gly Val Glu Val Leu Gly Gly Thr Glu Ala Asn Ile Leu Phe Cys Arg
        305                 310                 315                 320
        Leu Asp Ser Ala Met Ile Asp Ala Leu Leu Lys Ala Gly Phe Gly Phe
                        325                 330                 335
        Tyr His Asp Arg Trp Gly Pro Asn Val Val Arg Phe Val Thr Ser Phe
                        340                 345                 350
        Ala Thr Thr Ala Glu Asp Val Asp His Leu Leu Asn Gln Val Arg Leu
                        355                 360                 365
        Ala Ala Asp Arg Thr Gln Glu Arg
                        370                 375

<210> SEQ ID NO 27
<211> LENGTH: 1128
<212> TYPE: DNA
<213> ORGANISM: Artificial sequence
<220> FEATURE:
<223> OTHER INFORMATION: Engineered sequence

<400> SEQUENCE: 27
atgaacggtg aaacctcgcg tccgccggcg ctgggtttta gctctgataa ttatgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct cgctggctac ggaaatgagct atcgtcgcaa acgtgccggc     780
```

```
cacctgtcta gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct tggtttcta tcatgatcgt    1020 tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 28
<211> LENGTH: 376
<212> TYPE: PRT
<213> ORGANISM: Artificial sequence
<220> FEATURE:
<223> OTHER INFORMATION: Engineered sequence

<400> SEQUENCE: 28

```
Met Asn Gly Glu Thr Ser Arg Pro Pro Ala Leu Gly Phe Ser Ser Asp
1               5                   10                  15

Asn Tyr Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300
```

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
            325                 330                 335

Tyr His Asp Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
    355                 360                 365

Ala Ala Asp Arg Thr Gln Glu Arg
    370                 375

<210> SEQ ID NO 29
<211> LENGTH: 1128
<212> TYPE: DNA
<213> ORGANISM: Artificial sequence
<220> FEATURE:
<223> OTHER INFORMATION: Engineered sequence

<400> SEQUENCE: 29

```
atgaacggtg aaacctcgcg tccgccggcg ctgggttttta gctctgataa ttgggctggt      60
gcaagcccgg aagtcgcaca ggcactcgtt aagcacagtt cgggccaggc gggtccctat     120
ggcaccgacg agttgacggc acaggtcaag catagctccg ccaagctgg accttatggt      180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta tccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg cgttctggc ggccgaagca     720
attgtcctgt caataccctc gctggctacg gaaatgagct atcgtcgcaa acgtgccggc     780
cacctgtcta gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcta tcatgatcgt    1020
tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 30
<211> LENGTH: 376
<212> TYPE: PRT
<213> ORGANISM: Artificial sequence
<220> FEATURE:
<223> OTHER INFORMATION: Engineered sequence

<400> SEQUENCE: 30

Met Asn Gly Glu Thr Ser Arg Pro Pro Ala Leu Gly Phe Ser Ser Asp
1               5                   10                  15

Asn Trp Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
    35                  40                  45

Val Lys His Ser Ser Gly Gln Ala Gly Pro Tyr Gly Thr Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Pro Thr Gly Thr Ala Asn Ala Leu Cys Leu
                 85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
                115                 120                 125

Ala Lys Leu Met Thr Val Asp Gly Pro Ala Ala Lys Leu Asp Ile Val
                130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Met Asp Gly Ser Arg Phe Ala Asn Ala Leu Val
                195                 200                 205

Ser Leu Gly Cys Ser Pro Ala Glu Met Thr Trp Lys Ala Gly Val Asp
                210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
                260                 265                 270

Ile Asp Ala Tyr Leu Thr Asp Asp Leu Trp Leu Arg Asn Ala Arg Lys
                275                 280                 285

Ala Asn Ala Ala Ala Gln Arg Leu Ala Gln Gly Leu Glu Gly Leu Gly
                290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
    370                 375

<210> SEQ ID NO 31
<211> LENGTH: 1128
<212> TYPE: DNA
<213> ORGANISM: Artificial sequence
<220> FEATURE:
<223> OTHER INFORMATION: Engineered sequence

<400> SEQUENCE: 31
atgaacggtg aaacctcgcg tccgccggcg ctgggttttta gctctgataa tattgctggt    60

```
gcaagcccgg aagtcgcaca ggcactcgtt aagcacagtt cgggccaggc gggtccctat    120
ggcaccgacg agttgacggc acaggtcaag catagctccg gccaagctgg accttatggt    180
acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta tacccaggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctggtga gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc                 1128
```

<210> SEQ ID NO 32
<211> LENGTH: 376
<212> TYPE: PRT
<213> ORGANISM: Artificial sequence
<220> FEATURE:
<223> OTHER INFORMATION: Engineered sequence

<400> SEQUENCE: 32

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175
```

Tyr Thr Leu Asp Glu Ile Glu Ala Ile Gly Asp Val Cys Lys Ser Ser
                180                 185                 190

Ser Leu Gly Leu His Met Asp Gly Ser Arg Phe Ala Asn Ala Leu Val
            195                 200                 205

Ser Leu Gly Cys Ser Pro Ala Glu Met Thr Trp Lys Ala Gly Val Asp
        210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Val Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 33
<211> LENGTH: 1128
<212> TYPE: DNA
<213> ORGANISM: Artificial sequence
<220> FEATURE:
<223> OTHER INFORMATION: Engineered sequence

<400> SEQUENCE: 33
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctgg accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acgaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg gctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa acgtgccggc     780
cacctgcata gtaaaatgcg ctttctgagc gctcagatcg atgcgtacct gaccgatgac     840
ctgtggctgc gtaacgcccg caaagcaaat gcagctgcgc agcgtctggc ccaaggtctg     900

```
gaaggcctgg gcggtgttga agtcctgggc ggtaccgaag caaacattct gttctgtcgc    960
ctggattctg ccatgatcga cgcactgctg aaagctggct ttggtttcta tcatgatcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 34
<211> LENGTH: 376
<212> TYPE: PRT
<213> ORGANISM: Artificial sequence
<220> FEATURE:
<223> OTHER INFORMATION: Engineered sequence

<400> SEQUENCE: 34

```
Met Asn Gly Glu Thr Ser Arg Pro Pro Ala Leu Gly Phe Ser Asp
1               5                  10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Gly Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu His Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
```

```
                325                 330                 335
Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
            355                 360                 365

Ala Ala Asp Arg Thr Gln Glu Arg
            370                 375

<210> SEQ ID NO 35
<211> LENGTH: 1128
<212> TYPE: DNA
<213> ORGANISM: Artificial sequence
<220> FEATURE:
<223> OTHER INFORMATION: Engineered sequence

<400> SEQUENCE: 35
atgaacggtg aaacctcgcg tccgccggcg ctgggttta  gctctgataa tattgctggt    60
gcaagcccgg aagtcgcaca ggcactcgtt aagcacagtt cgggccaggc gggtccctat   120
ggcaccgacg agttgacggc acaggtcaag catagctccg ccaagctgg  accttatggt   180 acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatatta  ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta tacctggat   540 gaaattgaag ccatcggtga cgtgtgcaaa tcatcgagcc tgggtctgca catggatggc   600
tctcgttttg ctaatgcgct ggtgtccctg gctgttcac  cggcagaaat gacctggaaa   660
gccggtgttg acgcactgag tttggtgcg  acgaaaaacg cgttctggc  ggccgaagca   720 attgtcctgt tcaatacctc gctggctacg gaaatgagct atcgtcgcaa acgtgccggc   780
cacctgacca gtaaaatgcg ctttctgagc gctcagatcg atgcgtacct gaccgatgac   840
ctgtggctgc gtaacgcccg caaagcaaat gcagctgcgc agcgtctggc caaggtctg    900 gaaggcctgg gcggtgttga agtcctgggc ggtaccgaag caaacattct gttctgtcgc   960
ctggattctg ccatgatcga cgcactgctg aaagctggcc ttggttccta tcatgatcgt  1020
tggggtccga cgtggttcg  ctttgttacc agcttcgcta ccacggcgga agatgtggac  1080
cacctgctga atcaggttcg cctggccgca gaccgtacgc aagaacgc              1128

<210> SEQ ID NO 36
<211> LENGTH: 376
<212> TYPE: PRT
<213> ORGANISM: Artificial sequence
<220> FEATURE:
<223> OTHER INFORMATION: Engineered sequence

<400> SEQUENCE: 36

Met Asn Gly Glu Thr Ser Arg Pro Pro Ala Leu Gly Phe Ser Ser Asp
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
```

```
            50                  55                  60
Thr Ala Gln Val Lys Arg Lys Phe Cys Glu Ile Phe Glu Arg Asp Val
 65                  70                  75                  80

Glu Val Phe Leu Val Pro Thr Gly Thr Ala Asn Ala Leu Cys Leu
                 85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
            130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
            195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Met Arg Phe Leu Ser Ala Gln
            260                 265                 270

Ile Asp Ala Tyr Leu Thr Asp Asp Leu Trp Leu Arg Asn Ala Arg Lys
            275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
            355                 360                 365

Ala Ala Asp Arg Thr Gln Glu Arg
            370                 375

<210> SEQ ID NO 37
<211> LENGTH: 1128
<212> TYPE: DNA
<213> ORGANISM: Artificial sequence
<220> FEATURE:
<223> OTHER INFORMATION: Engineered sequence

<400> SEQUENCE: 37
atgaacggtg aaacctcgcg tccgccggcg ctgggtttta gctctgataa tattgctggt        60
gcaagcccgg aagtcgcaca ggcactcgtt aagcacagtt cgggccaggc gggtccctat       120
ggcaccgacg agttgacggc acaggtcaag catagctccg ccaagctgg accttatggt        180 acagatgaac tgactgctca agttaaacgt aaatttgcg aaatcttcga acgcgacgtc        240
```

```
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg cgttctggc ggccgaagca     720 attgtcctgt tcaataccte gctggctacg gaaatgagct atcgtcgcaa acgtgccggc    780
cacctgtcta gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgt gcatgatcgt   1020
tggggtccga acgtggttcg cttttgttacc agcttcgcta ccacggcgga agatgtggac   1080
cacctgctga atcaggttcg cctggccgca gaccgtacgc aagaacgc                1128

<210> SEQ ID NO 38
<211> LENGTH: 376
<212> TYPE: PRT
<213> ORGANISM: Artificial sequence
<220> FEATURE:
<223> OTHER INFORMATION: Engineered sequence

<400> SEQUENCE: 38

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205
```

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Val His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 39
<211> LENGTH: 1128
<212> TYPE: DNA
<213> ORGANISM: Artificial sequence
<220> FEATURE:
<223> OTHER INFORMATION: Engineered sequence

<400> SEQUENCE: 39
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta tacctggat     540 gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa acgtgccggc     780
cacctgtcta gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tggtttcgg gcatgatcgt    1020 tggggtccga acgtggttcg ctttgttacc agcttcgcta ccacggcgga agatgtggac    1080
cacctgctga atcaggttcg cctggccgca gaccgtacgc aagaacgc          1128

<210> SEQ ID NO 40
<211> LENGTH: 376
<212> TYPE: PRT
<213> ORGANISM: Artificial sequence
<220> FEATURE:
<223> OTHER INFORMATION: Engineered sequence

<400> SEQUENCE: 40

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 41
<211> LENGTH: 1128
<212> TYPE: DNA
<213> ORGANISM: Artificial sequence
<220> FEATURE:
<223> OTHER INFORMATION: Engineered sequence

<400> SEQUENCE: 41

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg gccaagctgg accttatggt   180
acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaataccct cgctggctac gaaatgagct atcgtcgcaa acgtgccggc   780
cacctgtcta gtaaaatgcg cttttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct tggtttcat tcatgatcgt  1020
tggggtccga acgtggttcg cttttgttacc agcttcgcta ccacggcgga agatgtggac  1080
cacctgctga atcaggttcg cctggccgca gaccgtacgc aagaacgc            1128
```

<210> SEQ ID NO 42
<211> LENGTH: 376
<212> TYPE: PRT
<213> ORGANISM: Artificial sequence
<220> FEATURE:
<223> OTHER INFORMATION: Engineered sequence

<400> SEQUENCE: 42

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Gly Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

```
Glu Val Phe Leu Val Pro Thr Gly Thr Ala Ala Asn Ala Leu Cys Leu
                 85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Ile His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375
```

<210> SEQ ID NO 43
<211> LENGTH: 1128
<212> TYPE: DNA
<213> ORGANISM: Artificial sequence
<220> FEATURE:
<223> OTHER INFORMATION: Engineered sequence

<400> SEQUENCE: 43

| | | | | | |
|---|---|---|---|---|---|
| atgaacggtg | aaacctcgcg | tccgccggcg | ctgggtttta | gctctgataa | tattgctggt | 60 |
| gcaagcccgg | aagtcgcaca | ggcactcgtt | aagcacagtt | cgggccaggc | gggtccctat | 120 |
| ggcaccgacg | agttgacggc | acaggtcaag | catagctccg | gccaagctgg | accttatggt | 180 |
| acagatgaac | tgactgctca | agttaaacgt | aaattttgcg | aaatcttcga | acgcgacgtc | 240 |
| gaagtgttcc | tggttccgac | cggtacggca | gcaaacgcac | tgtgtctgtc | cgcaatgacc | 300 |
| ccgccgtggg | gtaatattta | ctgccatccg | gcgtcccaca | tcaacaatga | tgaatgtggt | 360 |

```
gcgccggaat ttttctcaaa cggcgccaaa ctgatgaccg ttgatggtcc ggcagctaaa      420
ctggacattg tccgtctgcg cgaacgtacg cgcgaaaaag tgggtgatgt tcataccacg      480
cagccggcat gcgtctctat tacccaagct acggaagtgg gcagtatcta taccctggat      540
gaaattgaag ccatcggtga cgtgtgcaaa tcatcgagcc tgggtctgca catggatggc      600
tctcgttttg ctaatgcgct ggtgtccctg ggctgttcac cggcagaaat gacctggaaa      660
gccggtgttg acgcactgag ttttggtgcg acgaaaaacg gcgttctggc ggccgaagca      720
attgtcctgt caataccctc gctggctacg gaaatgagct atcgtcgcaa acgtgccggc      780
cacctgtcta gtaaatatcg ctttctgagc gctcagatcg atgcgtacct gaccgatgac      840
ctgtggctgc gtaacgcccg caaagcaaat gcagctgcgc agcgtctggc ccaaggtctg      900
gaaggcctgg gcggtgttga agtcctgggc ggtaccgaag caaacattct gttctgtcgc      960
ctggattctg ccatgatcga cgcactgctg aaagctggct ttggtttcta tcatgatcgt     1020
tggggtccga acgtggttcg ctttgttacc agcttcgcta ccacggcgga agatgtggac     1080
cacctgctga atcaggttcg cctggccgca gaccgtacgc aagaacgc                  1128
```

<210> SEQ ID NO 44
<211> LENGTH: 376
<212> TYPE: PRT
<213> ORGANISM: Artificial sequence
<220> FEATURE:
<223> OTHER INFORMATION: Engineered sequence

<400> SEQUENCE: 44

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
```

```
            225                 230                 235                 240
Ile Val Leu Phe Asn Thr Ser Leu Ala Thr Glu Met Ser Tyr Arg Arg
                245                 250                 255

Lys Arg Ala Gly His Leu Ser Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Tyr His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
            355                 360                 365

Ala Ala Asp Arg Thr Gln Glu Arg
            370                 375

<210> SEQ ID NO 45
<211> LENGTH: 1128
<212> TYPE: DNA
<213> ORGANISM: Artificial sequence
<220> FEATURE:
<223> OTHER INFORMATION: Engineered sequence

<400> SEQUENCE: 45
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga tccttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta ccctggat      540 gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg cgttctggc ggccgaagca      720 attgtcctgt caataccctc gctggctacg gaaatgagct atcgtcgcaa acgtgccggc     780
cacctgacca gtaaatatcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg catcgtcgt    1020 tggggtccga acgtggttcg ctttgttacc agcttcgcta ccacggcgga agatgtggac    1080
cacctgctga atcaggttcg cctggccgca gaccgtacgc aagaacgc               1128

<210> SEQ ID NO 46
```

```
<211> LENGTH: 376
<212> TYPE: PRT
<213> ORGANISM: Artificial sequence
<220> FEATURE:
<223> OTHER INFORMATION: Engineered sequence

<400> SEQUENCE: 46

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Arg Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375
```

<210> SEQ ID NO 47
<211> LENGTH: 1128
<212> TYPE: DNA
<213> ORGANISM: Artificial sequence
<220> FEATURE:
<223> OTHER INFORMATION: Engineered sequence

<400> SEQUENCE: 47

| | | |
|---|---|---|
| atgaacggtg aaacctcgcg tccgccggcg ctgggtttta gctctgataa tattgctggt | 60 |
| gcaagcccgg aagtcgcaca ggcactcgtt aagcacagtt cgggccaggc gggtccctat | 120 |
| ggcaccgacg agttgacggc acaggtcaag catagctccg gccaagctga tccttatggt | 180 |
| aacgatgaac tgactgctca agttaaacgt aaattttgcg aaatcttcga acgcgacgtc | 240 |
| gaagtgttcc tggttccgac cggtacggca gcaaacgcac tgtgtctgtc cgcaatgacc | 300 |
| ccgccgtggg gtaatattta ctgccatccg gcgtcccaca tcaacaatga tgaatgtggt | 360 |
| gcgccggaat ttttctcaaa cggcgccaaa ctgatgaccg ttgatggtcc ggcagctaaa | 420 |
| ctggacattg tccgtctgcg cgaacgtacg cgcgaaaaag tgggtgatgt tcataccacg | 480 |
| cagccggcat gcgtctctat tacccaagct acggaagtgg gcagtatcta taccctggat | 540 |
| gaaattgaag ccatcggtga cgtgtgcaaa tcatcgagcc tgggtctgca catggatggc | 600 |
| tctcgttttg ctaatgcgct ggtgtccctg ggctgttcac cggcagaaat gacctggaaa | 660 |
| gccggtgttg acgcactgag ttttggtgcg acgaaaaacg gcgttctggc ggccgaagca | 720 |
| attgtcctgt tcaataccac gctggctacg gaaatgagct atcgtcgcaa acgtgccggc | 780 |
| cacctgacca gtaaatatcg ctttctgagc gctcagatcg atgcgtacct gaccgatgac | 840 |
| ctgtggctgc gtaacgcccg caaagcaaat gcagctgcgc agcgtctggc ccaaggtctg | 900 |
| gaaggcctgg gcggtgttga agtcctgggc ggtaccgaag caaacattct gttctgtcgc | 960 |
| ctggattctg ccatgatcga cgcactgctg aaagctggct ttggtttcgg catcgtcgt | 1020 |
| tggggtccga acgtggttcg ctttgttacc agcttcgcta ccacggcgga agatgtggac | 1080 |
| cacctgctga atcaggttcg cctggccgca gaccgtacgc aagaacgc | 1128 |

<210> SEQ ID NO 48
<211> LENGTH: 376
<212> TYPE: PRT
<213> ORGANISM: Artificial sequence
<220> FEATURE:
<223> OTHER INFORMATION: Engineered sequence

<400> SEQUENCE: 48

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Asn Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
              115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Arg Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 49
<211> LENGTH: 1128
<212> TYPE: DNA
<213> ORGANISM: Artificial sequence
<220> FEATURE:
<223> OTHER INFORMATION: Engineered sequence

<400> SEQUENCE: 49
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctaa accttatggt      180 acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540

```
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcgcaa acgtgccggc     780
cacctgctga gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tggtttcgg gcataaacgt    1020 tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 50
<211> LENGTH: 376
<212> TYPE: PRT
<213> ORGANISM: Artificial sequence
<220> FEATURE:
<223> OTHER INFORMATION: Engineered sequence

<400> SEQUENCE: 50

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Lys Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255
```

```
Lys Arg Ala Gly His Leu Leu Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 51
<211> LENGTH: 1128
<212> TYPE: DNA
<213> ORGANISM: Artificial sequence
<220> FEATURE:
<223> OTHER INFORMATION: Engineered sequence

<400> SEQUENCE: 51
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctaa accttatggt     180 aacgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatttta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg cgttctggc ggccgaagca     720 attgtcctgt caataccctc gctggctacg gaaatgagct atcgtcgcaa acgtgccggc     780
cacctgacca gtaaaatgcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tggtttcgg cataaaacgt    1020 tggggtccga acgtggttcg ctttgttacc agcttcgcta ccacggcgga agatgtggac    1080
cacctgctga atcaggttcg cctggccgca gaccgtacgc aagaacgc               1128

<210> SEQ ID NO 52
<211> LENGTH: 376
<212> TYPE: PRT
<213> ORGANISM: Artificial sequence
<220> FEATURE:
<223> OTHER INFORMATION: Engineered sequence
```

<400> SEQUENCE: 52

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Lys Pro Tyr Gly Asn Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Met Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375
```

<210> SEQ ID NO 53
<211> LENGTH: 1128
<212> TYPE: DNA

<213> ORGANISM: Artificial sequence
<220> FEATURE:
<223> OTHER INFORMATION: Engineered sequence

<400> SEQUENCE: 53

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg gccaagctga tccttatggt   180
acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg cgttctggc ggccgaagca   720
attgtcctgt tcaataccta gctggctacg gaaatgagct atcgtcgcaa acgtgccggc   780
cacctgtcta gtaaaatgcg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg cataaacgt   1020
tggggtccga acgtggttcg ctttgttacc agcttcgcta ccacggcgga agatgtggac  1080
cacctgctga atcaggttcg cctggccgca gaccgtacgc aagaacgc               1128
```

<210> SEQ ID NO 54
<211> LENGTH: 376
<212> TYPE: PRT
<213> ORGANISM: Artificial sequence
<220> FEATURE:
<223> OTHER INFORMATION: Engineered sequence

<400> SEQUENCE: 54

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
```

```
                  130                 135                 140
Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
                260                 265                 270

Ile Asp Ala Tyr Leu Thr Asp Leu Trp Leu Arg Asn Ala Arg Lys
            275                 280                 285

Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
            355                 360                 365

Ala Ala Asp Arg Thr Gln Glu Arg
        370                 375

<210> SEQ ID NO 55
<211> LENGTH: 1128
<212> TYPE: DNA
<213> ORGANISM: Artificial sequence
<220> FEATURE:
<223> OTHER INFORMATION: Engineered sequence

<400> SEQUENCE: 55
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga tccttatggt      180 acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
```

```
gccggtgttg acgcactgag ttttggtgcg acgaaaaacg gcgttctggc ggccgaagca   720
attgtcctgt tcaataccct gctggctacg gaaatgagct atcgtcgcaa acgtgccggc   780
cacctgctga gtaaaatgcg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg cataaaacgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 56
<211> LENGTH: 376
<212> TYPE: PRT
<213> ORGANISM: Artificial sequence
<220> FEATURE:
<223> OTHER INFORMATION: Engineered sequence

<400> SEQUENCE: 56

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Leu Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285
```

```
Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 57
<211> LENGTH: 1128
<212> TYPE: DNA
<213> ORGANISM: Artificial sequence
<220> FEATURE:
<223> OTHER INFORMATION: Engineered sequence

<400> SEQUENCE: 57
atgaacggtg aaacctcgcg tccgccggcg ctgggttta gctctgataa tattgctggt      60
gcaagcccgg aagtcgcaca ggcactcgtt aagcacagtt cgggccaggc gggtccctat    120
ggcaccgacg agttgacggc acaggtcaag catagctccg ccaagctga tccttatggt     180 acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag tttggtgcg acgaaaaacg gcgttctggc ggccgaagca    720
attgtcctgt tcaatacctc gctggctacg gaaatgagct atcgtcgcaa cgtgccggc    780 cacctgacca gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg cataaaacgt   1020
tggggtccga acgtggttcg ctttgttacc agcttcgcta ccacggcgga agatgtggac   1080
cacctgctga atcaggttcg cctggccgca gaccgtacgc aagaacgc                1128

<210> SEQ ID NO 58
<211> LENGTH: 376
<212> TYPE: PRT
<213> ORGANISM: Artificial sequence
<220> FEATURE:
<223> OTHER INFORMATION: Engineered sequence

<400> SEQUENCE: 58

Met Asn Gly Glu Thr Ser Arg Pro Pro Ala Leu Gly Phe Ser Ser Asp
1               5                   10                  15
```

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 59
<211> LENGTH: 1128
<212> TYPE: DNA
<213> ORGANISM: Artificial sequence
<220> FEATURE:
<223> OTHER INFORMATION: Engineered sequence

<400> SEQUENCE: 59

```
atgaacggtg aaacctcgcg tccgccggcg ctgggtttta gctctgataa ttgggctggt    60
gcaagcccgg aagtcgcaca ggcactcgtt aagcacagtt cgggccaggc gggtccctat   120
ggcaccgacg agttgacggc acaggtcaag catagctccg gccaagctga tccttatggt   180
acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg cgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaatacctc gctggctacg gaaatgagct atcgtcgcaa cgtgccggc    780
cacctggtga gtaaaatgcg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg gcataaacgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 60
<211> LENGTH: 376
<212> TYPE: PRT
<213> ORGANISM: Artificial sequence
<220> FEATURE:
<223> OTHER INFORMATION: Engineered sequence

<400> SEQUENCE: 60

```
Met Asn Gly Glu Thr Ser Arg Pro Pro Ala Leu Gly Phe Ser Ser Asp
1               5                   10                  15

Asn Trp Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160
```

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Val Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 61
<211> LENGTH: 1128
<212> TYPE: DNA
<213> ORGANISM: Artificial sequence
<220> FEATURE:
<223> OTHER INFORMATION: Engineered sequence

<400> SEQUENCE: 61
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180 accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta ccctggat       540 gaaattgaag ccatcggtga cgtgtgcaaa tcatcgagcc tgggtctgca catggatggc     600
tctcgttttg ctaatgcgct ggtgtccctg gctgttcac cggcagaaat gacctggaaa      660
gccggtgttg acgcactgag ttttggtgcg acgaaaaacg gcgttctggc ggccgaagca     720
attgtcctgt tcaatacctc gctggctacg gaaatgagct atcgtcgcaa acgtgccggc     780
cacctgacga gtaaataccg ctttctgagc gctcagatcg atgcgtacct gaccgatgac     840

```
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg cataagcgt   1020 tggggtccga acgtgttcg ctttgttacc agcttcgcta ccacggcgga agatgtggac   1080
cacctgctga atcaggttcg cctggccgca gaccgtacgc aagaacgc               1128
```

```
<210> SEQ ID NO 62
<211> LENGTH: 376
<212> TYPE: PRT
<213> ORGANISM: Artificial sequence
<220> FEATURE:
<223> OTHER INFORMATION: Engineered sequence

<400> SEQUENCE: 62

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
```

```
                305                 310                 315                 320
Leu Asp Ser Ala Met Ile Asp Ala Leu Leu Lys Ala Gly Phe Gly Phe
                    325                 330                 335

Gly His Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
                370                 375

<210> SEQ ID NO 63
<211> LENGTH: 1128
<212> TYPE: DNA
<213> ORGANISM: Artificial sequence
<220> FEATURE:
<223> OTHER INFORMATION: Engineered sequence

<400> SEQUENCE: 63
atgaacggtg aaacctcgcg tccgccggcg ctgggttta gctctgataa tattgctggt      60
gcaagcccgg aagtcgcaca ggcactcgtt aagcacagtt cgggccaggc gggtccctat    120
ggcaccgacg agttgacggc acaggtcaag catagctccg ccaagctgg accttatggt     180 acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta tacccctggat   540 gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa cgtgccggc    780 cacctgtcta gtaaaatgcg cttttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtatgatcgt   1020
tggggtccga acgtggttcg ctttgttacc agcttcgcta ccacggcgga agatgtggac   1080
cacctgctga atcaggttcg cctggccgca gaccgtacgc aagaacgc               1128

<210> SEQ ID NO 64
<211> LENGTH: 376
<212> TYPE: PRT
<213> ORGANISM: Artificial sequence
<220> FEATURE:
<223> OTHER INFORMATION: Engineered sequence

<400> SEQUENCE: 64

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
```

```
            35                  40                  45
Val Lys His Ser Ser Gly Gln Ala Gly Pro Tyr Gly Thr Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Pro Thr Gly Thr Ala Asn Ala Leu Cys Leu
                 85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
                115                 120                 125

Ala Lys Leu Met Thr Val Asp Gly Pro Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Met Asp Gly Ser Arg Phe Ala Asn Ala Leu Val
                195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ser Ser Lys Met Arg Phe Leu Ser Ala Gln
                260                 265                 270

Ile Asp Ala Tyr Leu Thr Asp Asp Leu Trp Leu Arg Asn Ala Arg Lys
                275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Asp Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
370                 375

<210> SEQ ID NO 65
<211> LENGTH: 1128
<212> TYPE: DNA
<213> ORGANISM: Artificial sequence
<220> FEATURE:
<223> OTHER INFORMATION: Engineered sequence

<400> SEQUENCE: 65
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
```

```
ggcaccgacg agttgacggc acaggtcaag catagctccg gccaagctgg accttatggt    180
acagatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg cgttctggc ggccgaagca    720 attgtcctgt caataccctc gctggctacg gaaatgagct atcgtcgcaa acgtgccggc    780
cacctgacca gtaaaatgcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gcatgatcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 66
<211> LENGTH: 376
<212> TYPE: PRT
<213> ORGANISM: Artificial sequence
<220> FEATURE:
<223> OTHER INFORMATION: Engineered sequence

<400> SEQUENCE: 66

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190
```

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Met Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 67
<211> LENGTH: 1128
<212> TYPE: DNA
<213> ORGANISM: Artificial sequence
<220> FEATURE:
<223> OTHER INFORMATION: Engineered sequence

<400> SEQUENCE: 67
atgaacggtg aaacctcgcg tccgccggcg ctgggtttta gctctgataa tattgctggt        60
gcaagcccgg aagtcgcaca ggcactcgtt aagcacagtt cgggccaggc gggtccctat       120
ggcaccgacg agttgacggc acaggtcaag catagctccg ccaagctgg accttatggt        180 acagatgaac tgactgctca agttaaacgt aaattttgcg aaatcttcga acgcgacgtc       240
gaagtgttcc tggttccgac cggtacggca gcaaacgcac tgtgtctgtc cgcaatgacc       300
ccgccgtggg gtaatattta ctgccatccg cgtcccaca tcaacaatga tgaatgtggt        360
gcgccggaat ttttctcaaa cggcgccaaa ctgatgaccg ttgatggtcc ggcagctaaa       420
ctggacattg tccgtctgcg cgaacgtacg cgcgaaaaag tgggtgatgt tcataccacg       480
cagccggcat gcgtctctat tacccaagct acggaagtgg gcagtatcta ccctggat        540 gaaattgaag ccatcggtga cgtgtgcaaa tcatcgagcc tgggtctgca catggatggc       600
tctcgttttg ctaatgcgct ggtgtccctg gctgttcac cggcagaaat gacctggaaa       660
gccggtgttg acgcactgag ttttggtgcg acgaaaaacg gcgttctggc ggccgaagca       720
attgtcctgt tcaatacctc gctggctacg gaaatgagct atcgtcgcaa acgtgccggc       780
cacctgacca gtaaatatcg ctttctgagc gctcagatcg atgcgtacct gaccgatgac       840
ctgtggctgc gtaacgcccg caaagcaaat gcagctgcgc agcgtctggc ccaaggtctg       900
gaaggcctgg gcggtgttga agtcctgggc ggtaccgaag caaacattct gttctgtcgc       960

```
ctggattctg ccatgatcga cgcactgctg aaagctggct ttggtttcgg gcatcgtcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 68
<211> LENGTH: 376
<212> TYPE: PRT
<213> ORGANISM: Artificial sequence
<220> FEATURE:
<223> OTHER INFORMATION: Engineered sequence

<400> SEQUENCE: 68

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335
```

```
Gly His Arg Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 69
<211> LENGTH: 1128
<212> TYPE: DNA
<213> ORGANISM: Artificial sequence
<220> FEATURE:
<223> OTHER INFORMATION: Engineered sequence

<400> SEQUENCE: 69
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
acagatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc cggcgaagca     720
attgtcctgt tcaataccct cgctggctac gaaatgagct atcgtcgcaa acgtgccggc     780
cacctggtga gtaaatatcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg catgatcgt    1020
tggggtccga acgtggttcg cttttgttacc agcttcgcta ccacggcgga agatgtggac   1080
cacctgctga atcaggttcg cctggccgca gaccgtacgc aagaacgc               1128

<210> SEQ ID NO 70
<211> LENGTH: 376
<212> TYPE: PRT
<213> ORGANISM: Artificial sequence
<220> FEATURE:
<223> OTHER INFORMATION: Engineered sequence

<400> SEQUENCE: 70

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60
```

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Val Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Asp Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 71
<211> LENGTH: 1128
<212> TYPE: DNA
<213> ORGANISM: Artificial sequence
<220> FEATURE:
<223> OTHER INFORMATION: Engineered sequence

<400> SEQUENCE: 71
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctgga accttatggt     180
acagatgaac tgactgctca agttaaacgt aaatttgcg aaatcttcga acgcgacgtc     240
gaagtgttcc tggttccgac cggtacggca gcaaacgcac tgtgtctgtc cgcaatgacc     300

```
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acggaagtgg gcagtatcta tacccctggat   540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccctc gctggctacg gaaatgagct atcgtcgcaa acgtgccggc    780
cacctggtga gtaaatatcg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg cataaacgt     1020
tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 72
<211> LENGTH: 376
<212> TYPE: PRT
<213> ORGANISM: Artificial sequence
<220> FEATURE:
<223> OTHER INFORMATION: Engineered sequence

<400> SEQUENCE: 72

```
Met Asn Gly Glu Thr Ser Arg Pro Pro Ala Leu Gly Phe Ser Ser Asp
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
```

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
            245                 250                 255

Lys Arg Ala Gly His Leu Val Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 73
<211> LENGTH: 1128
<212> TYPE: DNA
<213> ORGANISM: Artificial sequence
<220> FEATURE:
<223> OTHER INFORMATION: Engineered sequence

<400> SEQUENCE: 73
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg ccaagctgg accttatggt   180 acagatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg cgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg gctgttcac cggcagaaat gacctggaaa   660
gccggtgttg acgcactgag ttttggtgcg acgaaaaacg cgttctggc ggccgaagca   720 attgtcctgt tcaataccct gctggctacg gaaatgagct atcgtcgcaa acgtgccggc   780
cacctgctga gtaaatatcg ctttctgagc gctcagatcg atgcgtacct gaccgatgac   840
ctgtggctgc gtaacgcccg caagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg cataaacgt  1020 tggggtccga acgtggttcg ctttgttacc agcttcgcta ccacggcgga agatgtggac  1080
cacctgctga atcaggttcg cctggccgca gaccgtacgc aagaacgc              1128

<210> SEQ ID NO 74
<211> LENGTH: 376
<212> TYPE: PRT
<213> ORGANISM: Artificial sequence
<220> FEATURE:
<223> OTHER INFORMATION: Engineered sequence

<400> SEQUENCE: 74

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Gly Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Leu Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365
```

```
Ala Ala Asp Arg Thr Gln Glu Arg
    370                 375

<210> SEQ ID NO 75
<211> LENGTH: 1128
<212> TYPE: DNA
<213> ORGANISM: Artificial sequence
<220> FEATURE:
<223> OTHER INFORMATION: Engineered sequence

<400> SEQUENCE: 75
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatgcg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatagcacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg cgttctggc ggccgaagca     720
attgtcctgt caataccctc gctggctacg gaaatgagct atcgtcgcaa cgtgccggc     780
cacctgacga gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg gaccaagcgt    1020
tggggtccga acgtggttcg ctttgttacc agcttcgcta ccacggcgga agatgtggac    1080
cacctgctga atcaggttcg cctggccgca gaccgtacgc aagaacgc                1128

<210> SEQ ID NO 76
<211> LENGTH: 376
<212> TYPE: PRT
<213> ORGANISM: Artificial sequence
<220> FEATURE:
<223> OTHER INFORMATION: Engineered sequence

<400> SEQUENCE: 76

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95
```

Ser Ala Met Thr Pro Pro Trp Gly Asn Ile Tyr Cys His Ala Ala Ser
            100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
            195                 200                 205

Ser Leu Gly Cys Ser Pro Ala Glu Met Thr Trp Lys Ala Gly Val Asp
            210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
            275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
            355                 360                 365

Ala Ala Asp Arg Thr Gln Glu Arg
370                 375

<210> SEQ ID NO 77
<211> LENGTH: 1128
<212> TYPE: DNA
<213> ORGANISM: Artificial sequence
<220> FEATURE:
<223> OTHER INFORMATION: Engineered sequence

<400> SEQUENCE: 77
atgaacggtg aaacctcgcg tccgccggcg ctgggttta gctctgataa tattgctggt      60
gcaagcccgg aagtcgcaca ggcactcgtt aagcacagtt cgggccaggc gggtccctat    120
ggcaccgacg agttgacggc acaggtcaag catagctccg ccaagctga cccttatggt     180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360
gcgccggaat ttttctcaaa cggcgccaaa ctgatgaccg ttgatggtcc ggcagctaaa    420

```
ctggacattg tccgtctgcg cgaacgtacg cgcgaaaaag tgggtgatgt tcataccacg      480
cagccggcat gcgtctctat tacccaagct acggaagtgg gcagtatcta taccctggat      540
gaaattgaag ccatcggtga cgtgtgcaaa tcatcgagcc tgggtctgca catggatggc      600
tctcgttttg ctaatgcgct ggtgtccctg ggctgttcac cggcagaaat gacctggaaa      660
gccggtgttg acgcactgag ttttggtgcg acgaaaaacg gcgttctggc ggccgaagca      720
attgtcctgt tcaataccct gctggctacg gaaatgagct atcgtcgcaa acgtgccggc      780
cacctgacga gtaaataccg ctttctgagc gctcagatcg atgcgtacct gaccgatgac      840
ctgtggctgc gtaacgcccg caaagcaaat gcagctgcgc agcgtctggc ccaaggtctg      900
gaaggcctgg gcggtgttga agtcctgggc ggtaccgaag caaacattct gttctgtcgc      960
ctggattctg ccatgatcga cgcactgctg aaagctggct ttggtttcgg gacgaagcgt     1020
tggggtccga acgtggttcg ctttgttacc agcttcgcta ccacggcgga agatgtggac     1080
cacctgctga atcaggttcg cctggccgca gaccgtacgc aagaacgc                 1128
```

<210> SEQ ID NO 78
<211> LENGTH: 376
<212> TYPE: PRT
<213> ORGANISM: Artificial sequence
<220> FEATURE:
<223> OTHER INFORMATION: Engineered sequence

<400> SEQUENCE: 78

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240
```

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
        260                 265                 270

Ile Asp Ala Tyr Leu Thr Asp Asp Leu Trp Leu Arg Asn Ala Arg Lys
    275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 79
<211> LENGTH: 1128
<212> TYPE: DNA
<213> ORGANISM: Artificial sequence
<220> FEATURE:
<223> OTHER INFORMATION: Engineered sequence

<400> SEQUENCE: 79
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180 accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt caataccctc gctggctacg gaaatgagct atcgtcgcaa cgtgccggc     780 cacctgacga gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tggtttcgg gtataagcgt    1020 tggggtccga acgtggttcg cttttgttacc agcttcgcta ccacggcgga agatgtggac    1080
cacctgctga atcaggttcg cctggccgca gaccgtacgc aagaacgc                1128

<210> SEQ ID NO 80
<211> LENGTH: 376
<212> TYPE: PRT

<213> ORGANISM: Artificial sequence
<220> FEATURE:
<223> OTHER INFORMATION: Engineered sequence

<400> SEQUENCE: 80

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375
```

-continued

<210> SEQ ID NO 81
<211> LENGTH: 1128
<212> TYPE: DNA
<213> ORGANISM: Artificial sequence
<220> FEATURE:
<223> OTHER INFORMATION: Engineered sequence

<400> SEQUENCE: 81

```
atgaacggtg aaacctcgcg tccgccggcg ctgggttttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg ccaagctga cccttatggt   180
accgatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatgcg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcatagcacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg cgttctggc ggccgaagca   720
attgtcctgt caataccctc gctggctacg gaaatgagct atcgtcgcaa acgtgccggc   780
cacctgacga gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg cataagcgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 82
<211> LENGTH: 376
<212> TYPE: PRT
<213> ORGANISM: Artificial sequence
<220> FEATURE:
<223> OTHER INFORMATION: Engineered sequence

<400> SEQUENCE: 82

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Ala Ala Ser
            100                 105                 110

His Ile Asn Asn Asp Glu Cys Gly Ala Pro Glu Phe Phe Ser Asn Gly

```
            115                 120                 125
Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 83
<211> LENGTH: 1128
<212> TYPE: DNA
<213> ORGANISM: Artificial sequence
<220> FEATURE:
<223> OTHER INFORMATION: Engineered sequence

<400> SEQUENCE: 83
atgaacggtg aaacctcgcg tccgccggcg ctgggtttta gctctgataa tattgctggt      60
gcaagcccgg aagtcgcaca ggcactcgtt aagcacagtt cgggccaggc gggtccctat    120
ggcaccgacg agttgacggc acaggtcaag catagctccg ccaagctga cccttatggt     180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg cgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcataccacg    480
cagccggcat gcgtctctat tacccaagct acgaagtgg gcagtatcta taccctggat     540
gaaattgaag ccatcggtga cgtgtgcaaa tcatcgagcc tgggtctgca catggatggc    600
```

```
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgatta gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcgtgttga agtcctgggc ggtaccgaag caaacattct gttctgtcgc    960
ctggattctg ccatgatcga cgcactgctg aaagctggct ttggtttcgg cataagcgt    1020 tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 84
<211> LENGTH: 376
<212> TYPE: PRT
<213> ORGANISM: Artificial sequence
<220> FEATURE:
<223> OTHER INFORMATION: Engineered sequence

<400> SEQUENCE: 84

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270
```

```
Ile Asp Ala Tyr Leu Thr Asp Leu Trp Leu Arg Asn Ala Arg Lys
    275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
                370                 375
```

<210> SEQ ID NO 85
<211> LENGTH: 1128
<212> TYPE: DNA
<213> ORGANISM: Artificial sequence
<220> FEATURE:
<223> OTHER INFORMATION: Engineered sequence

<400> SEQUENCE: 85

```
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg ccaagctga cccttatggt   180
accgatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta tacctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt caataccctc gctggctacg gaaatgagtc atcgtcgcaa acgtgccggc   780
cacctgacga gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg cataagcgt  1020
tggggtccga acgtggttcg cttttgttacc agcttcgcta ccacggcgga agatgtggac  1080
cacctgctga atcaggttcg cctggccgca gaccgtacgc aagaacgc            1128
```

<210> SEQ ID NO 86
<211> LENGTH: 376
<212> TYPE: PRT
<213> ORGANISM: Artificial sequence
<220> FEATURE:
<223> OTHER INFORMATION: Engineered sequence

<400> SEQUENCE: 86

Met Asn Gly Glu Thr Ser Arg Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65              70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly His Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 87
<211> LENGTH: 1128
<212> TYPE: DNA
<213> ORGANISM: Artificial sequence
<220> FEATURE:

<223> OTHER INFORMATION: Engineered sequence

<400> SEQUENCE: 87

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
gacaccgacg agttgacggc acaggtcaag catagctccg gccaagctga cccttatggt   180
accgatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaga ctgatgaccg ttgatggtcc ggcagctaaa   420
ctggacattg tccgtctgcg agaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tctcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaataccct gctggctacg gaaatgagct atcgtcgcaa cgtgccggc    780
cacctgacga gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttggtttcgg gacgaagcgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 88
<211> LENGTH: 376
<212> TYPE: PRT
<213> ORGANISM: Artificial sequence
<220> FEATURE:
<223> OTHER INFORMATION: Engineered sequence

<400> SEQUENCE: 88

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Asp Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Arg Leu Met Thr Val Asp Gly Pro Ala Ala Lys Leu Asp Ile Val
    130                 135                 140
```

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
            165                 170                 175

Tyr Thr Leu Asp Glu Ile Glu Ala Ile Gly Asp Val Cys Lys Ser Ser
        180                 185                 190

Ser Leu Gly Leu His Met Asp Gly Ser Arg Phe Ala Asn Ala Leu Val
    195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 89
<211> LENGTH: 1128
<212> TYPE: DNA
<213> ORGANISM: Artificial sequence
<220> FEATURE:
<223> OTHER INFORMATION: Engineered sequence

<400> SEQUENCE: 89
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggcaccgacg agttgacggc acaggtcaag catagctccg ccaagctga cccttatggt   180 accgatgaac tgactgctca agttaaacgt aaattttgcg aaatcttcga acgcgacgtc   240
gaagtgttcc tggttccgac cggtacggca gcaaacgcac tgtgtctgtc cgcaatgacc   300
ccgccgtggg gtaatattta ctgccatccg gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca cattgatggc   600
tctcgttttg ctaatgcgct ggtgtccctg ggctgttcac cggcagaaat gacctggaaa   660
gccggtgttg acgcgctgag ttttggtgcg acgaaaaacg gcgttctggc ggccgaagca   720

```
attgtcctgt caatacctc gctggttacg gaaatgagct atcgtcgcaa acgtgccggc    780
cacctgacga gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg cggtgttga agtcctgggc ggtaccgaag caaacattct gttctgtcgc    960
ctggattctg ccatgatcga cgcactgctg aaagctggct ttggtttcgg gacgaagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 90
<211> LENGTH: 376
<212> TYPE: PRT
<213> ORGANISM: Artificial sequence
<220> FEATURE:
<223> OTHER INFORMATION: Engineered sequence

<400> SEQUENCE: 90

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Ile Asp Gly Ser Arg Phe Ala Asn Ala Leu Val
            195                 200                 205

Ser Leu Gly Cys Ser Pro Ala Glu Met Thr Trp Lys Ala Gly Val Asp
        210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Val Thr Glu Met Ser Tyr Arg Arg
                245                 250                 255

Lys Arg Ala Gly His Leu Thr Ser Lys Tyr Arg Phe Leu Ser Ala Gln
                260                 265                 270

Ile Asp Ala Tyr Leu Thr Asp Asp Leu Trp Leu Arg Asn Ala Arg Lys
            275                 280                 285

Ala Asn Ala Ala Ala Gln Arg Leu Ala Gln Gly Leu Glu Gly Leu Gly
```

```
                290                 295                 300
Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 91
<211> LENGTH: 1128
<212> TYPE: DNA
<213> ORGANISM: Artificial sequence
<220> FEATURE:
<223> OTHER INFORMATION: Engineered sequence

<400> SEQUENCE: 91
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatacgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt caataccctc gctggctacg gaaatgagct atcgtcgcaa cgtgccggc     780 cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg tccgagcgt    1020 tggggtccga acgtggttcg ctttgttacc agcttcgcta ccacggcgga agatgtggac    1080
cacctgctga atcaggttcg cctggccgca gaccgtacgc aagaacgc                1128

<210> SEQ ID NO 92
<211> LENGTH: 376
<212> TYPE: PRT
<213> ORGANISM: Artificial sequence
<220> FEATURE:
<223> OTHER INFORMATION: Engineered sequence

<400> SEQUENCE: 92

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
```

```
                    20                  25                  30
        Ser Ser Gly Gln Ala Gly Pro Tyr Gly Thr Asp Glu Leu Thr Ala Gln
                    35                  40                  45

Val Lys His Ser Ser Gly Gln Ala Asp Pro Tyr Gly Thr Asp Glu Leu
                    50                  55                  60

Thr Ala Gln Val Lys Arg Lys Phe Cys Glu Ile Phe Glu Arg Asp Val
         65                  70                  75                  80

Glu Val Phe Leu Val Pro Thr Gly Thr Ala Ala Asn Ala Leu Cys Leu
                            85                  90                  95

Ser Ala Met Thr Pro Pro Trp Gly Asn Ile Tyr Cys His Pro Ala Ser
                        100                 105                 110

His Ile Asn Asn Asp Glu Cys Gly Ala Pro Glu Phe Phe Ser Asn Gly
                    115                 120                 125

Ala Lys Leu Met Thr Val Asp Gly Pro Ala Ala Lys Leu Asp Ile Val
                    130                 135                 140

Arg Leu Arg Glu Arg Thr Arg Glu Lys Val Gly Asp Val His Thr Thr
        145                 150                 155                 160

Gln Pro Ala Cys Val Ser Ile Thr Gln Ala Thr Glu Val Gly Ser Ile
                            165                 170                 175

Tyr Thr Leu Asp Glu Ile Glu Ala Ile Gly Asp Val Cys Lys Ser Ser
                        180                 185                 190

Ser Leu Gly Leu His Met Asp Gly Ser Arg Phe Ala Asn Ala Leu Val
                    195                 200                 205

Ser Leu Gly Cys Ser Pro Ala Glu Met Thr Trp Lys Ala Gly Val Asp
                    210                 215                 220

Ala Leu Ser Phe Gly Ala Thr Lys Asn Gly Val Leu Ala Ala Glu Ala
        225                 230                 235                 240

Ile Val Leu Phe Asn Thr Ser Leu Ala Thr Glu Met Ser Tyr Arg Arg
                            245                 250                 255

Lys Arg Ala Gly His Leu Ile Ser Lys Tyr Arg Phe Leu Ser Ala Gln
                        260                 265                 270

Ile Asp Ala Tyr Leu Thr Asp Asp Leu Trp Leu Arg Asn Ala Arg Lys
                    275                 280                 285

Ala Asn Ala Ala Ala Gln Arg Leu Ala Gln Gly Leu Glu Gly Leu Gly
                    290                 295                 300

Gly Val Glu Val Leu Gly Gly Thr Glu Ala Asn Ile Leu Phe Cys Arg
        305                 310                 315                 320

Leu Asp Ser Ala Met Ile Asp Ala Leu Leu Lys Ala Gly Phe Gly Phe
                            325                 330                 335

Gly Ser Glu Arg Trp Gly Pro Asn Val Val Arg Phe Val Thr Ser Phe
                        340                 345                 350

Ala Thr Thr Ala Glu Asp Val Asp His Leu Leu Asn Gln Val Arg Leu
                    355                 360                 365

Ala Ala Asp Arg Thr Gln Glu Arg
                    370                 375

<210> SEQ ID NO 93
<211> LENGTH: 1128
<212> TYPE: DNA
<213> ORGANISM: Artificial sequence
<220> FEATURE:
<223> OTHER INFORMATION: Engineered sequence

<400> SEQUENCE: 93
atgaacggtg aaacctcgcg tccgccggcg ctgggtttta gctctgataa tattgctggt      60
```

```
gcaagcccgg aagtcgcaca ggcactcgtt aagcacagtt cgggccaggc gggtccctat    120
ggcaccgacg agttgacggc acaggtcaag catagctccg gccaagctga cccttatggt    180
accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccc gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgctggaaag tgggtgatgt tcattcgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaatacctc gctggctacg gaaatgagct atcgtcgcaa cgtgccggc    780 cacctgacca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc                 1128
```

<210> SEQ ID NO 94
<211> LENGTH: 376
<212> TYPE: PRT
<213> ORGANISM: Artificial sequence
<220> FEATURE:
<223> OTHER INFORMATION: Engineered sequence

<400> SEQUENCE: 94

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
                100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Trp Lys Val Gly Asp Val His Ser Thr
145                 150                 155                 160

Gln Pro Ala Cys Val Ser Ile Thr Gln Ala Thr Glu Val Gly Ser Ile
                165                 170                 175
```

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 95
<211> LENGTH: 1128
<212> TYPE: DNA
<213> ORGANISM: Artificial sequence
<220> FEATURE:
<223> OTHER INFORMATION: Engineered sequence

<400> SEQUENCE: 95
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180 accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatacgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900

```
gaaggcctgg gcggtgttga agtcctgggc ggtaccgaag caaacattct gttctgtcgc    960
ctggattctg ccatgatcga cgcactgctg aaagctggct ttggtttcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 96
<211> LENGTH: 376
<212> TYPE: PRT
<213> ORGANISM: Artificial sequence
<220> FEATURE:
<223> OTHER INFORMATION: Engineered sequence

<400> SEQUENCE: 96

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
    115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
    195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
    275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320
```

Leu Asp Ser Ala Met Ile Asp Ala Leu Leu Lys Ala Gly Phe Gly Phe
            325                 330                 335

Gly Tyr Lys Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
    355                 360                 365

Ala Ala Asp Arg Thr Gln Glu Arg
370                 375

<210> SEQ ID NO 97
<211> LENGTH: 1128
<212> TYPE: DNA
<213> ORGANISM: Artificial sequence
<220> FEATURE:
<223> OTHER INFORMATION: Engineered sequence

<400> SEQUENCE: 97

| | | | | | |
|---|---|---|---|---|---|
| atgaacggtg | aaacctcgcg | tccgccggcg | ctgggttta | gctctgataa | tattgctggt | 60 |
| gcaagcccgg | aagtcgcaca | ggcactcgtt | aagcacagtt | cgggccaggc | gggtccctat | 120 |
| ggcaccgacg | agttgacggc | acaggtcaag | catagctccg | gccaagctga | cccttatggt | 180 |
| accgatgaac | tgactgctca | agttaaacgt | aaattttgcg | aaatcttcga | acgcgacgtc | 240 |
| gaagtgttcc | tggttccgac | cggtacggca | gcaaacgcac | tgtgtctgtc | cgcaatgacc | 300 |
| ccgccgtggg | gtaatattta | ctgccatcgc | gcgtcccaca | tcaacaatga | tgaatgtggt | 360 |
| gcgccggaat | tttctcaaa | cggcgccaaa | ctgatgaccg | ttgatggtcc | ggcagctaaa | 420 |
| ctggacattg | tccgtctgcg | cgaacgtacg | cgcgaaaaag | tgggtgatgt | tcattcgacg | 480 |
| cagccggcat | gcgtctctat | tacccaagct | acggaagtgg | gcagtatcta | taccctggat | 540 |
| gaaattgaag | ccatcggtga | cgtgtgcaaa | tcatcgagcc | tgggtctgca | catggatggc | 600 |
| tctcgttttg | ctaatgcgct | ggtgtccctg | ggctgttcac | cggcagaaat | gacctggaaa | 660 |
| gccggtgttg | acgcactgag | ttttggtgcg | acgaaaaacg | gcgttctggc | ggccgaagca | 720 |
| attgtcctgt | tcaataccct | gctggctacg | gaaatgagct | atcgtcgcaa | acgtgccggc | 780 |
| cacctgatca | gtaaataccg | ctttctgagc | gctcagatcg | atgcgtacct | gaccgatgac | 840 |
| ctgtggctgc | gtaacgcccg | caaagcaaat | gcagctgcgc | agcgtctggc | ccaaggtctg | 900 |
| gaaggcctgg | gcggtgttga | agtcctgggc | ggtaccgaag | caaacattct | gttctgtcgc | 960 |
| ctggattctg | ccatgatcga | cgcactgctg | aaagctggct | ttggtttcgg | gtacgagcgt | 1020 |
| tggggtccga | acgtggttcg | ctttgttacc | agcttcgcta | ccacggcgga | agatgtggac | 1080 |
| cacctgctga | atcaggttcg | cctggccgca | gaccgtacgc | aagaacgc | | 1128 |

<210> SEQ ID NO 98
<211> LENGTH: 376
<212> TYPE: PRT
<213> ORGANISM: Artificial sequence
<220> FEATURE:
<223> OTHER INFORMATION: Engineered sequence

<400> SEQUENCE: 98

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Pro Thr Gly Thr Ala Ala Asn Ala Leu Cys Leu
                 85                  90                  95

Ser Ala Met Thr Pro Pro Trp Gly Asn Ile Tyr Cys His Arg Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Met Asp Gly Ser Arg Phe Ala Asn Ala Leu Val
            195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
                260                 265                 270

Ile Asp Ala Tyr Leu Thr Asp Leu Trp Leu Arg Asn Ala Arg Lys
            275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Glu Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
            355                 360                 365

Ala Ala Asp Arg Thr Gln Glu Arg
    370                 375

<210> SEQ ID NO 99
<211> LENGTH: 1128
<212> TYPE: DNA
<213> ORGANISM: Artificial sequence
<220> FEATURE:
<223> OTHER INFORMATION: Engineered sequence

<400> SEQUENCE: 99
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180

-continued

```
accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatcgc gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 100
<211> LENGTH: 376
<212> TYPE: PRT
<213> ORGANISM: Artificial sequence
<220> FEATURE:
<223> OTHER INFORMATION: Engineered sequence

<400> SEQUENCE: 100

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Arg Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
```

```
                195                 200                 205
Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 101
<211> LENGTH: 1128
<212> TYPE: DNA
<213> ORGANISM: Artificial sequence
<220> FEATURE:
<223> OTHER INFORMATION: Engineered sequence

<400> SEQUENCE: 101
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt catacgacg      480 cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg gaacaagcgt    1020
```

```
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 102
<211> LENGTH: 376
<212> TYPE: PRT
<213> ORGANISM: Artificial sequence
<220> FEATURE:
<223> OTHER INFORMATION: Engineered sequence

<400> SEQUENCE: 102

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Asn Lys Arg Trp Gly Pro Asn Val Val Arg Phe Val Thr Ser Phe
            340                 345                 350
```

```
Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 103
<211> LENGTH: 1128
<212> TYPE: DNA
<213> ORGANISM: Artificial sequence
<220> FEATURE:
<223> OTHER INFORMATION: Engineered sequence

<400> SEQUENCE: 103
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaataatta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg aaggaaaaag tgggtgatgt tcataccacg     480
cagccggcat gcgtctctat tacccaagct acggaagtgg gcagtatcta tacctggat     540 gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt caataccctc gctggctacg gaaatgagct atcgtcgcaa acgtgccggc     780
cacctgacga gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttggtttcgg acgaagcgt    1020 tggggtccga acgtggttcg ctttgttacc agcttcgcta ccacggcgga agatgtggac    1080
cacctgctga atcaggttcg cctggccgca gaccgtacgc aagaacgc                1128

<210> SEQ ID NO 104
<211> LENGTH: 376
<212> TYPE: PRT
<213> ORGANISM: Artificial sequence
<220> FEATURE:
<223> OTHER INFORMATION: Engineered sequence

<400> SEQUENCE: 104

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80
```

Glu Val Phe Leu Val Pro Thr Gly Thr Ala Ala Asn Ala Leu Cys Leu
                    85                  90                  95

Ser Ala Met Thr Pro Pro Trp Gly Asn Asn Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Lys Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 105
<211> LENGTH: 1128
<212> TYPE: DNA
<213> ORGANISM: Artificial sequence
<220> FEATURE:
<223> OTHER INFORMATION: Engineered sequence

<400> SEQUENCE: 105
atgaacggtg aaacctcgcg tccgccggcg ctgggttttta gctctgataa tattgctggt     60
gcaagcccgg aagtcgcaca ggcactcgtt aagcacagtt cgggccaggc gggtccctat    120
ggcaccgacg agttgacggc acaggtcaag catagctccg ccaagctga ccctatggt     180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatccg gcgtcccaca tcaacaatga tgaatgtggt    360

```
gcgccggaat ttttctcaaa cggcgccaaa ctgatgaccg ttgatggtcc ggcagctaaa    420
ctggacattg tccgtctgcg cgaacgtacg agtgaaaaag tgggtgatgt tcataccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt caatacctc gctggctacg gaaatgagct atcgtcgcaa acgtgccggc    780
cacctgacga gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gacgaagcgt   1020
tggggtccga acgtggttcg ctttgttacc agcttcgcta ccacggcgga agatgtggac   1080
cacctgctga atcaggttcg cctggccgca gaccgtacgc aagaacgc               1128

<210> SEQ ID NO 106
<211> LENGTH: 376
<212> TYPE: PRT
<213> ORGANISM: Artificial sequence
<220> FEATURE:
<223> OTHER INFORMATION: Engineered sequence

<400> SEQUENCE: 106

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220
```

```
Ala Leu Ser Phe Gly Ala Thr Lys Asn Gly Val Leu Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 107
<211> LENGTH: 1128
<212> TYPE: DNA
<213> ORGANISM: Artificial sequence
<220> FEATURE:
<223> OTHER INFORMATION: Engineered sequence

<400> SEQUENCE: 107
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcgcaa acgtgccggc     780
cacctgacga gtaaatatcg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tacgttcgg dacgaagcgt    1020
tggggtccga cgtggttcg ctttgttacc agcttcgcta ccacggcgga agatgtggac    1080
cacctgctga atcaggttcg cctggccgca gaccgtacgc aagaacgc                1128
```

```
<210> SEQ ID NO 108
<211> LENGTH: 376
<212> TYPE: PRT
<213> ORGANISM: Artificial sequence
<220> FEATURE:
<223> OTHER INFORMATION: Engineered sequence

<400> SEQUENCE: 108

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Thr Phe
                325                 330                 335

Gly Thr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
```

<210> SEQ ID NO 109
<211> LENGTH: 1128
<212> TYPE: DNA
<213> ORGANISM: Artificial sequence
<220> FEATURE:
<223> OTHER INFORMATION: Engineered sequence

<400> SEQUENCE: 109

```
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatccg gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt caataccctc gctggctacg gaaatgagct atcgtcgcaa acgtgccggc     780
cacctgacga gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaagttcgg acgaagcgt     1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 110
<211> LENGTH: 376
<212> TYPE: PRT
<213> ORGANISM: Artificial sequence
<220> FEATURE:
<223> OTHER INFORMATION: Engineered sequence

<400> SEQUENCE: 110

```
Met Asn Gly Glu Thr Ser Arg Pro Pro Ala Leu Gly Phe Ser Ser Asp
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His Pro Ala Ser
```

100                 105                 110
His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
        180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
        210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Thr Ser Lys Tyr Arg Phe Leu Ser Ala Gln
        260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Thr Lys Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 111
<211> LENGTH: 1128
<212> TYPE: DNA
<213> ORGANISM: Artificial sequence
<220> FEATURE:
<223> OTHER INFORMATION: Engineered sequence

<400> SEQUENCE: 111
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
ggcaccgacg agttgacggc acaggtcaag catagctccg ccaagctga ccctattggt      180 accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatacgacg     480

```
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgctttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtacgggcgt   1020
tggggtccga acgtggttcg ctttgttacc agcttcgcta ccacggcgga agatgtggac   1080
cacctgctga atcaggttcg cctggccgca gaccgtacgc aagaacgc                 1128

<210> SEQ ID NO 112
<211> LENGTH: 376
<212> TYPE: PRT
<213> ORGANISM: Artificial sequence
<220> FEATURE:
<223> OTHER INFORMATION: Engineered sequence

<400> SEQUENCE: 112

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255
```

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Gly Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 113
<211> LENGTH: 1128
<212> TYPE: DNA
<213> ORGANISM: Artificial sequence
<220> FEATURE:
<223> OTHER INFORMATION: Engineered sequence

<400> SEQUENCE: 113
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat    120
ggcaccgacg agttgacggc acaggtcaag catagctccg ccaagctgac ccttatggt     180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatatttta ctgccatcac gcgtcccaca tcaacaatga tgaatgtggt   360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta tacccttggat   540 gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg cgttctggc ggccgaagca     720 attgtcctgt tcaataccct gctggctacg gaaatgagct atcgtcgcaa cgtgccggc     780 cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtacaagcgt   1020
tggggtccga acgtgtgtcg ctttgttacc agcttcgcta ccacggcgga agatgtggac   1080
cacctgctga atcaggttcg cctggccgca gaccgtacgc aagaacgc                1128

<210> SEQ ID NO 114
<211> LENGTH: 376
<212> TYPE: PRT
<213> ORGANISM: Artificial sequence
<220> FEATURE:

<223> OTHER INFORMATION: Engineered sequence

<400> SEQUENCE: 114

| | | | | | | | | | | | | | | |
|---|---|---|---|---|---|---|---|---|---|---|---|---|---|---|
| Met | Asn | Gly | Glu | Thr | Ser | Arg | Pro | Pro | Ala | Leu | Gly | Phe | Ser | Ser | Glu |
| 1 | | | | 5 | | | | | 10 | | | | | 15 | |
| Asn | Ile | Ala | Gly | Ala | Ser | Pro | Glu | Val | Ala | Gln | Ala | Leu | Val | Lys | His |
| | | | 20 | | | | | 25 | | | | | 30 | | |
| Ser | Ser | Gly | Gln | Ala | Gly | Pro | Tyr | Gly | Thr | Asp | Glu | Leu | Thr | Ala | Gln |
| | | | 35 | | | | | 40 | | | | | 45 | | |
| Val | Lys | His | Ser | Ser | Gly | Gln | Ala | Asp | Pro | Tyr | Gly | Thr | Asp | Glu | Leu |
| | 50 | | | | | 55 | | | | | 60 | | | | |
| Thr | Ala | Gln | Val | Lys | Arg | Lys | Phe | Cys | Glu | Ile | Phe | Glu | Arg | Asp | Val |
| 65 | | | | | 70 | | | | | 75 | | | | | 80 |
| Glu | Val | Phe | Leu | Val | Pro | Thr | Gly | Thr | Ala | Ala | Asn | Ala | Leu | Cys | Leu |
| | | | | 85 | | | | | 90 | | | | | 95 | |
| Ser | Ala | Met | Thr | Pro | Pro | Trp | Gly | Asn | Ile | Tyr | Cys | His | His | Ala | Ser |
| | | | 100 | | | | | 105 | | | | | 110 | | |
| His | Ile | Asn | Asn | Asp | Glu | Cys | Gly | Ala | Pro | Glu | Phe | Phe | Ser | Asn | Gly |
| | | | | 115 | | | | | 120 | | | | | 125 | |
| Ala | Lys | Leu | Met | Thr | Val | Asp | Gly | Pro | Ala | Ala | Lys | Leu | Asp | Ile | Val |
| | 130 | | | | | 135 | | | | | 140 | | | | |
| Arg | Leu | Arg | Glu | Arg | Thr | Arg | Glu | Lys | Val | Gly | Asp | Val | His | Thr | Thr |
| 145 | | | | | 150 | | | | | 155 | | | | | 160 |
| Gln | Pro | Ala | Cys | Val | Ser | Ile | Thr | Gln | Ala | Thr | Glu | Val | Gly | Ser | Ile |
| | | | | 165 | | | | | 170 | | | | | 175 | |
| Tyr | Thr | Leu | Asp | Glu | Ile | Glu | Ala | Ile | Gly | Asp | Val | Cys | Lys | Ser | Ser |
| | | | 180 | | | | | 185 | | | | | 190 | | |
| Ser | Leu | Gly | Leu | His | Met | Asp | Gly | Ser | Arg | Phe | Ala | Asn | Ala | Leu | Val |
| | | | | 195 | | | | | 200 | | | | | 205 | |
| Ser | Leu | Gly | Cys | Ser | Pro | Ala | Glu | Met | Thr | Trp | Lys | Ala | Gly | Val | Asp |
| | 210 | | | | | 215 | | | | | 220 | | | | |
| Ala | Leu | Ser | Phe | Gly | Ala | Thr | Lys | Asn | Gly | Val | Leu | Ala | Ala | Glu | Ala |
| 225 | | | | | 230 | | | | | 235 | | | | | 240 |
| Ile | Val | Leu | Phe | Asn | Thr | Ser | Leu | Ala | Thr | Glu | Met | Ser | Tyr | Arg | Arg |
| | | | | 245 | | | | | 250 | | | | | 255 | |
| Lys | Arg | Ala | Gly | His | Leu | Ile | Ser | Lys | Tyr | Arg | Phe | Leu | Ser | Ala | Gln |
| | | | 260 | | | | | 265 | | | | | 270 | | |
| Ile | Asp | Ala | Tyr | Leu | Thr | Asp | Leu | Trp | Leu | Arg | Asn | Ala | Arg | Lys |
| | | | 275 | | | | | 280 | | | | | 285 | | |
| Ala | Asn | Ala | Ala | Ala | Gln | Arg | Leu | Ala | Gln | Gly | Leu | Glu | Gly | Leu | Gly |
| | | | 290 | | | | | 295 | | | | | 300 | | |
| Gly | Val | Glu | Val | Leu | Gly | Gly | Thr | Glu | Ala | Asn | Ile | Leu | Phe | Cys | Arg |
| 305 | | | | | 310 | | | | | 315 | | | | | 320 |
| Leu | Asp | Ser | Ala | Met | Ile | Asp | Ala | Leu | Leu | Lys | Ala | Gly | Phe | Gly | Phe |
| | | | | 325 | | | | | 330 | | | | | 335 | |
| Gly | Tyr | Lys | Arg | Trp | Gly | Pro | Asn | Val | Cys | Arg | Phe | Val | Thr | Ser | Phe |
| | | | 340 | | | | | 345 | | | | | 350 | | |
| Ala | Thr | Thr | Ala | Glu | Asp | Val | Asp | His | Leu | Leu | Asn | Gln | Val | Arg | Leu |
| | | | | 355 | | | | | 360 | | | | | 365 | |
| Ala | Ala | Asp | Arg | Thr | Gln | Glu | Arg |
| | 370 | | | | | 375 | |

<210> SEQ ID NO 115
<211> LENGTH: 1128

<212> TYPE: DNA
<213> ORGANISM: Artificial sequence
<220> FEATURE:
<223> OTHER INFORMATION: Engineered sequence

<400> SEQUENCE: 115

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg aaggaaaaag tgggtgatgt tcattcgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa cgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttcgcttcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 116
<211> LENGTH: 376
<212> TYPE: PRT
<213> ORGANISM: Artificial sequence
<220> FEATURE:
<223> OTHER INFORMATION: Engineered sequence

<400> SEQUENCE: 116

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125
```

Ala Lys Leu Met Thr Val Asp Gly Pro Ala Ala Lys Leu Asp Ile Val
    130                 135                 140

Arg Leu Arg Glu Arg Thr Lys Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Arg Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 117
<211> LENGTH: 1128
<212> TYPE: DNA
<213> ORGANISM: Artificial sequence
<220> FEATURE:
<223> OTHER INFORMATION: Engineered sequence

<400> SEQUENCE: 117
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660

```
gccggtgttg acgcactgag ttttggtgcg acgaaaaacg gcgttctggc ggccgaagca    720
attgtcctgt tcaataccct gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttggtttcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 118
<211> LENGTH: 376
<212> TYPE: PRT
<213> ORGANISM: Artificial sequence
<220> FEATURE:
<223> OTHER INFORMATION: Engineered sequence

<400> SEQUENCE: 118

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
```

```
                   275                 280                 285
Ala Asn Ala Ala Ala Gln Arg Leu Ala Gln Gly Leu Glu Gly Leu Gly
        290                 295                 300
Gly Val Glu Val Leu Gly Gly Thr Glu Ala Asn Ile Leu Phe Cys Arg
305                 310                 315                 320
Leu Asp Ser Ala Met Ile Asp Ala Leu Leu Lys Ala Gly Phe Gly Phe
                325                 330                 335
Gly Tyr Lys Arg Trp Gly Pro Asn Val Val Arg Phe Val Thr Ser Phe
                340                 345                 350
Ala Thr Thr Ala Glu Asp Val Asp His Leu Leu Asn Gln Val Arg Leu
                355                 360                 365
Ala Ala Asp Arg Thr Gln Glu Arg
        370                 375

<210> SEQ ID NO 119
<211> LENGTH: 1128
<212> TYPE: DNA
<213> ORGANISM: Artificial sequence
<220> FEATURE:
<223> OTHER INFORMATION: Engineered sequence

<400> SEQUENCE: 119
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt    180
accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg tccgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg gcctgttcac cggcagaaat gacctggaaa    660
gccggtgttg acgcactgag ttttggtgcg acgaaaaacg cgttctggc ggccgaagca    720
attgtcctgt tcaataccctc gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct taaattcgg gtacaagcgt   1020
tggggtccga cgtggttcg ctttgttacc agcttcgcta ccacggcgga agatgtggac   1080
cacctgctga atcaggttcg cctggccgca gaccgtacgc aagaacgc              1128

<210> SEQ ID NO 120
<211> LENGTH: 376
<212> TYPE: PRT
<213> ORGANISM: Artificial sequence
<220> FEATURE:
<223> OTHER INFORMATION: Engineered sequence

<400> SEQUENCE: 120

Met Asn Gly Glu Thr Ser Arg Pro Pro Ala Leu Gly Phe Ser Ser Glu
```

```
1               5                   10                  15
Asn Ile Ala Gly Ala Ser Pro Glu Val Ala Gln Ala Leu Val Lys His
            20                  25                  30
Ser Ser Gly Gln Ala Gly Pro Tyr Gly Thr Asp Glu Leu Thr Ala Gln
            35                  40                  45
Val Lys His Ser Ser Gly Gln Ala Asp Pro Tyr Gly Thr Asp Glu Leu
    50                  55                  60
Thr Ala Gln Val Lys Arg Lys Phe Cys Glu Ile Phe Glu Arg Asp Val
65                  70                  75                  80
Glu Val Phe Leu Val Pro Thr Gly Thr Ala Ala Asn Ala Leu Cys Leu
                85                  90                  95
Ser Ala Met Thr Pro Pro Trp Gly Asn Ile Tyr Cys His His Ala Ser
            100                 105                 110
His Ile Asn Asn Asp Glu Cys Gly Ala Pro Glu Phe Ser Asn Gly
            115                 120                 125
Ala Lys Leu Met Thr Val Asp Gly Pro Ala Ala Lys Leu Asp Ile Val
        130                 135                 140
Arg Leu Arg Glu Arg Thr Ser Glu Lys Val Gly Asp Val His Thr Thr
145                 150                 155                 160
Gln Pro Ala Cys Val Ser Ile Thr Gln Ala Thr Glu Val Gly Ser Ile
                165                 170                 175
Tyr Thr Leu Asp Glu Ile Glu Ala Ile Gly Asp Val Cys Lys Ser Ser
            180                 185                 190
Ser Leu Gly Leu His Met Asp Gly Ser Arg Phe Ala Asn Ala Leu Val
        195                 200                 205
Ser Leu Gly Cys Ser Pro Ala Glu Met Thr Trp Lys Ala Gly Val Asp
    210                 215                 220
Ala Leu Ser Phe Gly Ala Thr Lys Asn Gly Val Leu Ala Ala Glu Ala
225                 230                 235                 240
Ile Val Leu Phe Asn Thr Ser Leu Ala Thr Glu Met Ser Tyr Arg Arg
                245                 250                 255
Lys Arg Ala Gly His Leu Ile Ser Lys Tyr Arg Phe Leu Ser Ala Gln
            260                 265                 270
Ile Asp Ala Tyr Leu Thr Asp Leu Trp Leu Arg Asn Ala Arg Lys
        275                 280                 285
Ala Asn Ala Ala Ala Gln Arg Leu Ala Gln Gly Leu Glu Gly Leu Gly
    290                 295                 300
Gly Val Glu Val Leu Gly Gly Thr Glu Ala Asn Ile Leu Phe Cys Arg
305                 310                 315                 320
Leu Asp Ser Ala Met Ile Asp Ala Leu Leu Lys Ala Gly Phe Lys Phe
                325                 330                 335
Gly Tyr Lys Arg Trp Gly Pro Asn Val Val Arg Phe Val Thr Ser Phe
            340                 345                 350
Ala Thr Thr Ala Glu Asp Val Asp His Leu Leu Asn Gln Val Arg Leu
        355                 360                 365
Ala Ala Asp Arg Thr Gln Glu Arg
    370                 375

<210> SEQ ID NO 121
<211> LENGTH: 1128
<212> TYPE: DNA
<213> ORGANISM: Artificial sequence
<220> FEATURE:
<223> OTHER INFORMATION: Engineered sequence
```

<400> SEQUENCE: 121

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg aacgaaaaag tgggtgatgt tcattcgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccte gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 122
<211> LENGTH: 376
<212> TYPE: PRT
<213> ORGANISM: Artificial sequence
<220> FEATURE:
<223> OTHER INFORMATION: Engineered sequence

<400> SEQUENCE: 122

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
        130                 135                 140

Arg Leu Arg Glu Arg Thr Asn Glu Lys Val Gly Asp Val His Ser Thr
145                 150                 155                 160
```

Gln Pro Ala Cys Val Ser Ile Thr Gln Ala Thr Glu Val Gly Ser Ile
            165                 170                 175

Tyr Thr Leu Asp Glu Ile Glu Ala Ile Gly Asp Val Cys Lys Ser Ser
        180                 185                 190

Ser Leu Gly Leu His Met Asp Gly Ser Arg Phe Ala Asn Ala Leu Val
    195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 123
<211> LENGTH: 1128
<212> TYPE: DNA
<213> ORGANISM: Artificial sequence
<220> FEATURE:
<223> OTHER INFORMATION: Engineered sequence

<400> SEQUENCE: 123
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt    180 ttcgatgaac tgactgctca agttaaacgt aaattttgcg aaatcttcga acgcgacgtc    240
gaagtgttcc tggttccaac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcattcgacg    480
cagccggcat gcgtctctat tacccaagct acggaagtgg gcagtatcta taccctggat    540
gaaattgaag ccatcggtga cgtgtgcaaa tcatcgagcc tggtctgca catggatggc    600 gcccgttttg ctaatgcgct ggtgtccctg gctgttcac cggcagaaat gacctggaaa    660
gccggtgttg acgcactgag ttttggtgcg acgaaaaacg gcgttctggc ggccgaagca    720
attgtcctgt tcaatacctc gctggctacg gaaatgagct atcgtcgcaa acgtgccggc    780

-continued

```
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 124
<211> LENGTH: 376
<212> TYPE: PRT
<213> ORGANISM: Artificial sequence
<220> FEATURE:
<223> OTHER INFORMATION: Engineered sequence

<400> SEQUENCE: 124

```
Met Asn Gly Glu Thr Ser Arg Pro Pro Ala Leu Gly Phe Ser Ser Glu
  1               5                  10                  15

Asn Ile Ala Gly Ala Ser Pro Glu Val Ala Gln Ala Leu Val Lys His
                 20                  25                  30

Ser Ser Gly Gln Ala Gly Pro Tyr Gly Thr Asp Glu Leu Thr Ala Gln
             35                  40                  45

Val Lys His Ser Ser Gly Gln Ala Asp Pro Tyr Gly Phe Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Pro Thr Gly Thr Ala Ala Asn Ala Leu Cys Leu
                 85                  90                  95

Ser Ala Met Thr Pro Pro Trp Gly Asn Ile Tyr Cys His His Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
            195                 200                 205

Ser Leu Gly Cys Ser Pro Ala Glu Met Thr Trp Lys Ala Gly Val Asp
        210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300
```

```
Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
            325                 330                 335

Gly Tyr Lys Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
    355                 360                 365

Ala Ala Asp Arg Thr Gln Glu Arg
    370                 375

<210> SEQ ID NO 125
<211> LENGTH: 1128
<212> TYPE: DNA
<213> ORGANISM: Artificial sequence
<220> FEATURE:
<223> OTHER INFORMATION: Engineered sequence

<400> SEQUENCE: 125
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt    180
ttcgatgaac tgactgctca agttaaacgt aaattttgcg aaatcttcga acgcgacgtc    240
gaagtgttcc tggttggaac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta tacccctggat   540
gaaattgaag ccatcggtga cgtgtgcaaa tcatcgagcc tgggtctgca catggatggc    600
gcccgttttg ctaatgcgct ggtgtccctg ggctgttcac cggcagaaat gacctggaaa    660
gccggtgttg acgcactgag ttttggtgcg acgaaaaacg cgttctggc ggccgaagca     720
attgtcctgt tcaataccct gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct taaaattcgg gtacaagcgt   1020
tggggtccga cgtggttcg ctttgttacc agcttcgcta ccacggcgga agatgtggac   1080
cacctgctga atcaggttcg cctggccgca gaccgtacgc aagaacgc               1128

<210> SEQ ID NO 126
<211> LENGTH: 376
<212> TYPE: PRT
<213> ORGANISM: Artificial sequence
<220> FEATURE:
<223> OTHER INFORMATION: Engineered sequence

<400> SEQUENCE: 126

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30
```

```
Ser Ser Gly Gln Ala Gly Pro Tyr Gly Thr Asp Glu Leu Thr Ala Gln
         35                  40                  45

Val Lys His Ser Ser Gly Gln Ala Asp Pro Tyr Gly Phe Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Gly Thr Gly Thr Ala Ala Asn Ala Leu Cys Leu
                 85                  90                  95

Ser Ala Met Thr Pro Pro Trp Gly Asn Ile Tyr Cys His His Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Met Asp Gly Ala Arg Phe Ala Asn Ala Leu Val
                195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
                260                 265                 270

Ile Asp Ala Tyr Leu Thr Asp Asp Leu Trp Leu Arg Asn Ala Arg Lys
                275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
370                 375

<210> SEQ ID NO 127
<211> LENGTH: 1128
<212> TYPE: DNA
<213> ORGANISM: Artificial sequence
<220> FEATURE:
<223> OTHER INFORMATION: Engineered sequence

<400> SEQUENCE: 127
atgaacggtg aaacctcgcg tccgccggcg ctgggttttta gctctgaaaa tattgctggt      60
gcaagcccgg aagtcgcaca ggcactcgtt aagcacagtt cgggccaggc gggtccctat     120
```

```
ggcaccgacg agttgacggc acaggtcaag catagctccg gccaagctga cccttatggt    180
ttcgatgaac tgactgctca agttaaacgt aaattttgcg aaatcttcga acgcgacgtc    240
gaagtgttcc tggttgccac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta tacctggat    540 gaaattgaag ccatcggtga cgtgtgcaaa tcatcgagcc tgggtctgca catggatggc    600
gcccgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt caataccctc gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacgagcgt   1020
tggggtccga acgtggttcg ctttgttacc agcttcgcta ccacggcgga agatgtggac   1080
cacctgctga atcaggttcg cctggccgca gaccgtacgc aagaacgc                1128

<210> SEQ ID NO 128
<211> LENGTH: 376
<212> TYPE: PRT
<213> ORGANISM: Artificial sequence
<220> FEATURE:
<223> OTHER INFORMATION: Engineered sequence

<400> SEQUENCE: 128

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Phe Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
```

```
            180                 185                 190
Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Glu Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 129
<211> LENGTH: 1128
<212> TYPE: DNA
<213> ORGANISM: Artificial sequence
<220> FEATURE:
<223> OTHER INFORMATION: Engineered sequence

<400> SEQUENCE: 129
atgaacggtg aaacctcgcg tccgccggcg ctgggttta gctctgaaaa tattgctggt      60
gcaagcccgg aagtcgcaca ggcactcgtt aagcacagtt cgggccaggc gggtccctat    120
ggcaccgacg agttgacggc acaggtcaag catagctccg ccaagctga cccttatggt    180 accgatgaac tgactgctca agttaaacgt aaattttgcg aaatcttcga acgcgacgtc    240
gaagtgttcc tggttgccac cggtacggca gcaaacgcac tgtgtctgtc cgcaatgacc    300
ccgccgtggg gtaatatttta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
gcccgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccct gctggctacg gaaatgagct atcgtcgcaa acgtgccggc    780
cacctgatca gtaaatacccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
```

```
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 130
<211> LENGTH: 376
<212> TYPE: PRT
<213> ORGANISM: Artificial sequence
<220> FEATURE:
<223> OTHER INFORMATION: Engineered sequence

<400> SEQUENCE: 130

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335
```

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 131
<211> LENGTH: 1128
<212> TYPE: DNA
<213> ORGANISM: Artificial sequence
<220> FEATURE:
<223> OTHER INFORMATION: Engineered sequence

<400> SEQUENCE: 131

```
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg gccaagctga cccttatggt   180
accgatgaac tgactgctca agttaaacgt aaattttgcg aaatcttcga acgcgacgtc   240
gaagtgttcc tggttgccac cggtacggca gcaaacgcac tgtgtctgtc cgcaatgacc   300
ccgccgtggg gtaatattta ctgccatcac gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt catacgacg    480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
gcccgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaataccct gctggctacg gaaatgagct atcgtcgcaa acgtgccggc   780
cacctgatca gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttcgcttcgg gtacaagcgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 132
<211> LENGTH: 376
<212> TYPE: PRT
<213> ORGANISM: Artificial sequence
<220> FEATURE:
<223> OTHER INFORMATION: Engineered sequence

<400> SEQUENCE: 132

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

```
Thr Ala Gln Val Lys Arg Lys Phe Cys Glu Ile Phe Glu Arg Asp Val
 65                  70                  75                  80

Glu Val Phe Leu Val Ala Thr Gly Thr Ala Asn Ala Leu Cys Leu
                 85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Arg Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 133
<211> LENGTH: 1128
<212> TYPE: DNA
<213> ORGANISM: Artificial sequence
<220> FEATURE:
<223> OTHER INFORMATION: Engineered sequence

<400> SEQUENCE: 133
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt    180 accgatgaac tgactgctca gttaaacgt aaattttgcg aaatcttcga acgcgacgtc    240
```

```
gaagtgttcc tggttgccac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
gcccgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt caataccctc gctggctacg gaaatgagct atcgtcacaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 134
<211> LENGTH: 376
<212> TYPE: PRT
<213> ORGANISM: Artificial sequence
<220> FEATURE:
<223> OTHER INFORMATION: Engineered sequence

<400> SEQUENCE: 134

```
Met Asn Gly Glu Thr Ser Arg Pro Pro Ala Leu Gly Phe Ser Ser Glu
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205
```

```
Ser Leu Gly Cys Ser Pro Ala Glu Met Thr Trp Lys Ala Gly Val Asp
    210                 215                 220
Ala Leu Ser Phe Gly Ala Thr Lys Asn Gly Val Leu Ala Ala Glu Ala
225                 230                 235                 240
Ile Val Leu Phe Asn Thr Ser Leu Ala Thr Glu Met Ser Tyr Arg His
                245                 250                 255
Lys Arg Ala Gly His Leu Ile Ser Lys Tyr Arg Phe Leu Ser Ala Gln
                260                 265                 270
Ile Asp Ala Tyr Leu Thr Asp Asp Leu Trp Leu Arg Asn Ala Arg Lys
                275                 280                 285
Ala Asn Ala Ala Ala Gln Arg Leu Ala Gln Gly Leu Glu Gly Leu Gly
290                 295                 300
Gly Val Glu Val Leu Gly Gly Thr Glu Ala Asn Ile Leu Phe Cys Arg
305                 310                 315                 320
Leu Asp Ser Ala Met Ile Asp Ala Leu Leu Lys Ala Gly Phe Lys Phe
                325                 330                 335
Gly Tyr Lys Arg Trp Gly Pro Asn Val Val Arg Phe Val Thr Ser Phe
                340                 345                 350
Ala Thr Thr Ala Glu Asp Val Asp His Leu Leu Asn Gln Val Arg Leu
                355                 360                 365
Ala Ala Asp Arg Thr Gln Glu Arg
370                 375
```

<210> SEQ ID NO 135
<211> LENGTH: 1128
<212> TYPE: DNA
<213> ORGANISM: Artificial sequence
<220> FEATURE:
<223> OTHER INFORMATION: Engineered sequence

<400> SEQUENCE: 135

```
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg ccaagctgac cccttatggt   180
accgatgaac tgactgctca agttaaacgt aaattttgcg aaatcttcga acgcgacgtc   240
gaagtgttcc tggttccaac cggtacggca gcaaacgcac tgtgtctgtc cgcaatgacc   300
ccgccgtggg gtaatatttt actgccatca cgcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg cgcgaaaaag tgggtgatgt tcatacgacg   480
cagccggcat gcgtctctat tacccaagct acggaagtgg gcagtatcta tacctggat    540
gaaattgaag ccatcggtga cgtgtgcaaa tcatcgagcc tgggtctgca catggatggc   600
tcacgttttg ctaatgcgct ggtgtccctg gctgttcac cggcagaaat gacctggaaa   660
gccggtgttg acgcactgag ttttggtgcg acgaaaaacg cgttctggc ggccgaagca   720
attgtcctgt tcaatacctc gctggctacg gaaatgagct atcgtcgcaa cgtgccggc    780
cacctgatca gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttaaattcgg gtacaagcgt  1020
tggggtccga acgtggttcg ctttgttacc agcttcgcta ccacggcgga agatgtggac  1080
```
cacctgctga atcaggttcg cctggccgca gaccgtacgc aagaacgc    1128

<210> SEQ ID NO 136
<211> LENGTH: 376
<212> TYPE: PRT
<213> ORGANISM: Artificial sequence
<220> FEATURE:
<223> OTHER INFORMATION: Engineered sequence

<400> SEQUENCE: 136

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu

Ala Ala Asp Arg Thr Gln Glu Arg
    370             375

<210> SEQ ID NO 137
<211> LENGTH: 1128
<212> TYPE: DNA
<213> ORGANISM: Artificial sequence
<220> FEATURE:
<223> OTHER INFORMATION: Engineered sequence

<400> SEQUENCE: 137

| | |
|---|---|
| atgaacggtg aaacctcgcg tccgccggcg ctgggttta gctctgaaaa tattgctggt | 60 |
| gcaagcccgg aagtcgcaca ggcactcgtt aagcacagtt cgggccaggc gggtccctat | 120 |
| ggcaccgacg agttgacggc acaggtcaag catagctccg gccaagctga cccttatggt | 180 |
| accgatgaac tgactgctca agttaaacgt aaattttgcg aaatcttcga acgcgacgtc | 240 |
| gaagtgttcc tggttgccac cggtacggca gcaaacgcac tgtgtctgtc cgcaatgacc | 300 |
| ccgccgtggg gtaatattta ctgccatcac gcgtcccaca tcaacaatga tgaatgtggt | 360 |
| gcgccggaat ttttctcaaa cggcgccaaa ctgatgaccg ttgatggtcc ggcagctaaa | 420 |
| ctggacattg tccgtctgcg cgaacgtacg cgcgaaaaag tgggtgatgt tcatacgacg | 480 |
| cagccggcat gcgtctctat tacccaagct acggaagtgg gcagtatcta taccctggat | 540 |
| gaaattgaag ccatcggtga cgtgtgcaaa tcatcgagcc tgggtctgca catggatggc | 600 |
| tcacgttttg ctaatgcgct ggtgtccctg ggctgttcac cggcagaaat gacctggaaa | 660 |
| gccggtgttg acgcactgag ttttggtgcg acgaaaaacg gcgttctggc ggccgaagca | 720 |
| attgtcctgt caataccctc gctggctacg gaaatgagct atcgtcgcaa acgtgccggc | 780 |
| cacctgatca gtaaataccg ctttctgagc gctcagatcg atgcgtacct gaccgatgac | 840 |
| ctgtggctgc gtaacgcccg caaagcaaat gcagctgcgc agcgtctggc ccaaggtctg | 900 |
| gaaggcctgg gcggtgttga gtcctgggc ggtaccgaag caaacattct gttctgtcgc | 960 |
| ctggattctg ccatgatcga cgcactgctg aaagctggct ttaaattcgg gtacaagcgt | 1020 |
| tggggtccga acgtggttcg ctttgttacc agcttcgcta ccacggcgga agatgtggac | 1080 |
| cacctgctga atcaggttcg cctggccgca gaccgtacgc aagaacgc | 1128 |

<210> SEQ ID NO 138
<211> LENGTH: 376
<212> TYPE: PRT
<213> ORGANISM: Artificial sequence
<220> FEATURE:
<223> OTHER INFORMATION: Engineered sequence

<400> SEQUENCE: 138

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu

```
                    85                  90                  95
Ser Ala Met Thr Pro Pro Trp Gly Asn Ile Tyr Cys His His Ala Ser
                100                 105                 110

His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 139
<211> LENGTH: 1128
<212> TYPE: DNA
<213> ORGANISM: Artificial sequence
<220> FEATURE:
<223> OTHER INFORMATION: Engineered sequence

<400> SEQUENCE: 139
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat    120
ggcaccgacg agttgacggc acaggtcaag catagctccg ccaagctga ccettatggt    180 accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatcac gcgtcccaca tcaacaatga tgaatgtggt    360
gcgccggaat tttctcaaa cggcgccaaa ctgatgaccg ttgatggtcc ggcagctaaa    420
```

```
ctggacattg tccgtctgcg cgaacgtacg aaggaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccctc gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 140  
<211> LENGTH: 376  
<212> TYPE: PRT  
<213> ORGANISM: Artificial sequence  
<220> FEATURE:  
<223> OTHER INFORMATION: Engineered sequence

<400> SEQUENCE: 140

```
Met Asn Gly Glu Thr Ser Arg Pro Pro Ala Leu Gly Phe Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Lys Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240
```

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 141
<211> LENGTH: 1128
<212> TYPE: DNA
<213> ORGANISM: Artificial sequence
<220> FEATURE:
<223> OTHER INFORMATION: Engineered sequence

<400> SEQUENCE: 141

```
atgaacggtg aaacctcgcg tccgccggcg ctgggtttta gctctgaaaa tattgttggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg tccgaaaaag tgggtgatgt tcatacgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt caataccctc gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tcgcttcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 142
<211> LENGTH: 376

```
<212> TYPE: PRT
<213> ORGANISM: Artificial sequence
<220> FEATURE:
<223> OTHER INFORMATION: Engineered sequence

<400> SEQUENCE: 142
```

| | | | | | | | | | | | | | | | |
|---|---|---|---|---|---|---|---|---|---|---|---|---|---|---|---|
| Met | Asn | Gly | Glu | Thr | Ser | Arg | Pro | Pro | Ala | Leu | Gly | Phe | Ser | Ser | Glu |
| 1 | | | | 5 | | | | | 10 | | | | | 15 | |
| Asn | Ile | Val | Gly | Ala | Ser | Pro | Glu | Val | Ala | Gln | Ala | Leu | Val | Lys | His |
| | | | 20 | | | | | 25 | | | | | 30 | | |
| Ser | Ser | Gly | Gln | Ala | Gly | Pro | Tyr | Gly | Thr | Asp | Glu | Leu | Thr | Ala | Gln |
| | | | 35 | | | | | 40 | | | | | 45 | | |
| Val | Lys | His | Ser | Ser | Gly | Gln | Ala | Asp | Pro | Tyr | Gly | Thr | Asp | Glu | Leu |
| | | | 50 | | | | | 55 | | | | | 60 | | |
| Thr | Ala | Gln | Val | Lys | Arg | Lys | Phe | Cys | Glu | Ile | Phe | Glu | Arg | Asp | Val |
| 65 | | | | | 70 | | | | | 75 | | | | | 80 |
| Glu | Val | Phe | Leu | Val | Pro | Thr | Gly | Thr | Ala | Ala | Asn | Ala | Leu | Cys | Leu |
| | | | | 85 | | | | | 90 | | | | | 95 | |
| Ser | Ala | Met | Thr | Pro | Pro | Trp | Gly | Asn | Ile | Tyr | Cys | His | His | Ala | Ser |
| | | | | 100 | | | | | 105 | | | | | 110 | |
| His | Ile | Asn | Asn | Asp | Glu | Cys | Gly | Ala | Pro | Glu | Phe | Phe | Ser | Asn | Gly |
| | | | | 115 | | | | | 120 | | | | | 125 | |
| Ala | Lys | Leu | Met | Thr | Val | Asp | Gly | Pro | Ala | Ala | Lys | Leu | Asp | Ile | Val |
| | | | 130 | | | | | 135 | | | | | 140 | | |
| Arg | Leu | Arg | Glu | Arg | Thr | Ser | Glu | Lys | Val | Gly | Asp | Val | His | Thr | Thr |
| 145 | | | | | 150 | | | | | 155 | | | | | 160 |
| Gln | Pro | Ala | Cys | Val | Ser | Ile | Thr | Gln | Ala | Thr | Glu | Val | Gly | Ser | Ile |
| | | | | 165 | | | | | 170 | | | | | 175 | |
| Tyr | Thr | Leu | Asp | Glu | Ile | Glu | Ala | Ile | Gly | Asp | Val | Cys | Lys | Ser | Ser |
| | | | 180 | | | | | 185 | | | | | 190 | | |
| Ser | Leu | Gly | Leu | His | Met | Asp | Gly | Ser | Arg | Phe | Ala | Asn | Ala | Leu | Val |
| | | | 195 | | | | | 200 | | | | | 205 | | |
| Ser | Leu | Gly | Cys | Ser | Pro | Ala | Glu | Met | Thr | Trp | Lys | Ala | Gly | Val | Asp |
| | | | 210 | | | | | 215 | | | | | 220 | | |
| Ala | Leu | Ser | Phe | Gly | Ala | Thr | Lys | Asn | Gly | Val | Leu | Ala | Ala | Glu | Ala |
| 225 | | | | | 230 | | | | | 235 | | | | | 240 |
| Ile | Val | Leu | Phe | Asn | Thr | Ser | Leu | Ala | Thr | Glu | Met | Ser | Tyr | Arg | Arg |
| | | | | 245 | | | | | 250 | | | | | 255 | |
| Lys | Arg | Ala | Gly | His | Leu | Ile | Ser | Lys | Tyr | Arg | Phe | Leu | Ser | Ala | Gln |
| | | | 260 | | | | | 265 | | | | | 270 | | |
| Ile | Asp | Ala | Tyr | Leu | Thr | Asp | Leu | Trp | Leu | Arg | Asn | Ala | Arg | Lys | |
| | | | 275 | | | | | 280 | | | | | 285 | | |
| Ala | Asn | Ala | Ala | Ala | Gln | Arg | Leu | Ala | Gln | Gly | Leu | Glu | Gly | Leu | Gly |
| | | | 290 | | | | | 295 | | | | | 300 | | |
| Gly | Val | Glu | Val | Leu | Gly | Gly | Thr | Glu | Ala | Asn | Ile | Leu | Phe | Cys | Arg |
| 305 | | | | | 310 | | | | | 315 | | | | | 320 |
| Leu | Asp | Ser | Ala | Met | Ile | Asp | Ala | Leu | Leu | Lys | Ala | Gly | Phe | Arg | Phe |
| | | | | 325 | | | | | 330 | | | | | 335 | |
| Gly | Tyr | Lys | Arg | Trp | Gly | Pro | Asn | Val | Val | Arg | Phe | Val | Thr | Ser | Phe |
| | | | 340 | | | | | 345 | | | | | 350 | | |
| Ala | Thr | Thr | Ala | Glu | Asp | Val | Asp | His | Leu | Leu | Asn | Gln | Val | Arg | Leu |
| | | | 355 | | | | | 360 | | | | | 365 | | |
| Ala | Ala | Asp | Arg | Thr | Gln | Glu | Arg | | | | | | | | |
| | | | 370 | | | | | 375 | | | | | | | |

<210> SEQ ID NO 143
<211> LENGTH: 1128
<212> TYPE: DNA
<213> ORGANISM: Artificial sequence
<220> FEATURE:
<223> OTHER INFORMATION: Engineered sequence

<400> SEQUENCE: 143

```
atgaacggtg aaacctcgcg tccgccggcg ctgggttta gctctgaaaa tattgctggt      60
gcaagcccgg aagtcgcaca ggcactcgtt aagcacagtt cgggccaggc gggtccctat    120
ggcaccgacg agttgacggc acaggtcaag catagctccg gccaagctga cccttatggt    180
accgatgaac tgactgctca agttaaacgt aaattttgcg aaatcttcga acgcgacgtc    240
gaagtgttcc tggttccgac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg tccgaaaaag tgggtgatgt cattcgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
tctcgttttg ctaatgcgct ggtgtccctg gctgttcac cggcagaaat gacctggaaa    660
gccggtgttg acgcactgag ttttggtgcg acgaaaacg cgttctggc ggccgaagca    720
attgtcctgt caataccctc gctggctacg gaaatgagct atcgtcgcaa cgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacaagcgt   1020
tgggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 144
<211> LENGTH: 376
<212> TYPE: PRT
<213> ORGANISM: Artificial sequence
<220> FEATURE:
<223> OTHER INFORMATION: Engineered sequence

<400> SEQUENCE: 144

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
                100                 105                 110

```
His Ile Asn Asn Asp Glu Cys Gly Ala Pro Glu Phe Phe Ser Asn Gly
            115                 120                 125

Ala Lys Leu Met Thr Val Asp Gly Pro Ala Ala Lys Leu Asp Ile Val
130                 135                 140

Arg Leu Arg Glu Arg Thr Ser Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375
```

<210> SEQ ID NO 145
<211> LENGTH: 1128
<212> TYPE: DNA
<213> ORGANISM: Artificial sequence
<220> FEATURE:
<223> OTHER INFORMATION: Engineered sequence

<400> SEQUENCE: 145

| | | | | | |
|---|---|---|---|---|---|
| atgaacggtg | aaacctcgcg | tccgccggcg | ctgggtttta | gctctgaaaa | tattgctggt | 60 |
| gcaagcccgg | aagtcgcaca | ggcactcgtt | aagcacagtt | cgggccaggc | gggtccctat | 120 |
| ggcaccgacg | agttgacggc | acaggtcaag | catagctccg | ccaagctga | cccttatggt | 180 |
| accgatgaac | tgactgctca | agttaaacgt | aaattttgcg | aaatcttcga | acgcgacgtc | 240 |
| gaagtgttcc | tggttccgac | cggtacggca | gcaaacgcac | tgtgtctgtc | cgcaatgacc | 300 |
| ccgccgtggg | gtaatattta | ctgccatcac | gcgtcccaca | tcaacaatga | tgaatgtggt | 360 |
| gcgccggaat | ttttctcaaa | cggcgccaaa | ctgatgaccg | ttgatggtcc | ggcagctaaa | 420 |
| ctggacattg | tccgtctgcg | cgaacgtacg | aaggaaaaag | tgggtgatgt | tcattcgacg | 480 |
| cagccggcat | gcgtctctat | tacccaagct | acggaagtgg | gcagtatcta | taccctggat | 540 |

```
gaaattgaag ccatcggtga cgtgtgcaaa tcatcgagcc tgggtctgca catggatggc    600
tctcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccte gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaaattcg gtacgagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 146
<211> LENGTH: 376
<212> TYPE: PRT
<213> ORGANISM: Artificial sequence
<220> FEATURE:
<223> OTHER INFORMATION: Engineered sequence

<400> SEQUENCE: 146

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Lys Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
```

```
                260                 265                 270
Ile Asp Ala Tyr Leu Thr Asp Asp Leu Trp Leu Arg Asn Ala Arg Lys
            275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Glu Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
            355                 360                 365

Ala Ala Asp Arg Thr Gln Glu Arg
            370                 375

<210> SEQ ID NO 147
<211> LENGTH: 1128
<212> TYPE: DNA
<213> ORGANISM: Artificial sequence
<220> FEATURE:
<223> OTHER INFORMATION: Engineered sequence

<400> SEQUENCE: 147
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg tccgaaaaag tgggtgatgt tcattcgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg gctgttcac cggcagaaat gacctggaaa      660
gccggtgttg acgcactgag ttttggtgcg acgaaaaacg gcgttctggc ggccgaagca     720
attgtcctgt tcaataccct gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct tactttcgg gtacaagcgt    1020 tggggtccga acgtggttcg ctttgttacc agcttcgcta ccacggcgga agatgtggac    1080
cacctgctga atcaggttcg cctggccgca gaccgtacgc aagaacgc               1128

<210> SEQ ID NO 148
<211> LENGTH: 376
<212> TYPE: PRT
<213> ORGANISM: Artificial sequence
<220> FEATURE:
<223> OTHER INFORMATION: Engineered sequence
```

<400> SEQUENCE: 148

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Thr Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375
```

<210> SEQ ID NO 149
<211> LENGTH: 1128
<212> TYPE: DNA
<213> ORGANISM: Artificial sequence
<220> FEATURE:
<223> OTHER INFORMATION: Engineered sequence

<400> SEQUENCE: 149

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180
accgatgaac tgactgctca agttaaacgt aaatttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg agagaaaaag tgggtgatgt tcattcgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc              1128
```

<210> SEQ ID NO 150
<211> LENGTH: 376
<212> TYPE: PRT
<213> ORGANISM: Artificial sequence
<220> FEATURE:
<223> OTHER INFORMATION: Engineered sequence

<400> SEQUENCE: 150

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140
```

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
            165                 170                 175

Tyr Thr Leu Asp Glu Ile Glu Ala Ile Gly Asp Val Cys Lys Ser Ser
        180                 185                 190

Ser Leu Gly Leu His Met Asp Gly Ser Arg Phe Ala Asn Ala Leu Val
    195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 151
<211> LENGTH: 1128
<212> TYPE: DNA
<213> ORGANISM: Artificial sequence
<220> FEATURE:
<223> OTHER INFORMATION: Engineered sequence

<400> SEQUENCE: 151
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt     180 accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg agagaaaaag tgggtgatgt tcattcgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720

```
attgtcctgt tcaataccto gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacgagcgt   1020
tggggtccga acgtggttcg ctttgttacc agcttcgcta ccacggcgga agatgtggac   1080
cacctgctga atcaggttcg cctggccgca gaccgtacgc aagaacgc              1128
```

<210> SEQ ID NO 152
<211> LENGTH: 376
<212> TYPE: PRT
<213> ORGANISM: Artificial sequence
<220> FEATURE:
<223> OTHER INFORMATION: Engineered sequence

<400> SEQUENCE: 152

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285
```

Ala Asn Ala Ala Ala Gln Arg Leu Ala Gln Gly Leu Glu Gly Leu Gly
        290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Glu Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 153
<211> LENGTH: 1128
<212> TYPE: DNA
<213> ORGANISM: Artificial sequence
<220> FEATURE:
<223> OTHER INFORMATION: Engineered sequence

<400> SEQUENCE: 153
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctgaa cccttatggt     180
accgatgaac tgactgctca agttaaacgt aaattttgcg aaatcttcga acgcgacgtc     240
gaagtgttcc tggttccgac cggtacggca gcaaacgcac tgtgtctgtc cgcaatgacc     300
ccgccgtggg gtaatatttt actgccatca cgcgtcccac atcaacaatga tgaatgtggt     360 gcgccggaat ttttctcaaa cggcgccaaa ctgatgaccg ttgatggtcc ggcagctaaa     420
ctggacattg tccgtctgcg cgaacgtacg aaggaaaaag tgggtgatgt tcattcgacg     480
cagccggcat gcgtctctat tacccaagct acggaagtgg gcagtatcta tacctggat     540 gaaattgaag ccatcggtga cgtgtgcaaa tcatcgagcc tgggtctgca catggatggc     600
tctcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccct cgctggctac gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga gtcctgggc ggtaccgaag caaacattct gttctgtcgc     960
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc              1128

<210> SEQ ID NO 154
<211> LENGTH: 376
<212> TYPE: PRT
<213> ORGANISM: Artificial sequence
<220> FEATURE:
<223> OTHER INFORMATION: Engineered sequence

<400> SEQUENCE: 154

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Lys Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 155
<211> LENGTH: 1128
<212> TYPE: DNA
<213> ORGANISM: Artificial sequence
<220> FEATURE:
<223> OTHER INFORMATION: Engineered sequence

<400> SEQUENCE: 155

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttccaac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt catacgacg      480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
gcccgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaataccte gctggctacg gaaatgagct atcgtcgcaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacaagcgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 156
<211> LENGTH: 376
<212> TYPE: PRT
<213> ORGANISM: Artificial sequence
<220> FEATURE:
<223> OTHER INFORMATION: Engineered sequence

<400> SEQUENCE: 156

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
```

```
                    165                 170                 175
Tyr Thr Leu Asp Glu Ile Glu Ala Ile Gly Asp Val Cys Lys Ser Ser
                180                 185                 190

Ser Leu Gly Leu His Met Asp Gly Ala Arg Phe Ala Asn Ala Leu Val
            195                 200                 205

Ser Leu Gly Cys Ser Pro Ala Glu Met Thr Trp Lys Ala Gly Val Asp
        210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 157
<211> LENGTH: 1128
<212> TYPE: DNA
<213> ORGANISM: Artificial sequence
<220> FEATURE:
<223> OTHER INFORMATION: Engineered sequence

<400> SEQUENCE: 157
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180
accgatgaac tgactgctca agttaaacgt aaattttgcg aaatcttcga acgcgacgtc     240
gaagtgttcc tggttccaac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatacgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
gcccgttttg ctaatgcgct ggtgtccctg gctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcgcaa acgtgccggc     780
cacctgatca gtaaataccg ctttctgagc gctcagatcg atgcgtacct gaccgatgac     840
```

```
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacgagcgt   1020
tggggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 158
<211> LENGTH: 376
<212> TYPE: PRT
<213> ORGANISM: Artificial sequence
<220> FEATURE:
<223> OTHER INFORMATION: Engineered sequence

<400> SEQUENCE: 158

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320
```

Leu Asp Ser Ala Met Ile Asp Ala Leu Leu Lys Ala Gly Phe Lys Phe
            325                 330                 335

Gly Tyr Glu Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 159
<211> LENGTH: 1128
<212> TYPE: DNA
<213> ORGANISM: Artificial sequence
<220> FEATURE:
<223> OTHER INFORMATION: Engineered sequence

<400> SEQUENCE: 159

```
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt     180
ttcgatgaac tgactgctca agttaaacgt aaattttgcg aaatcttcga acgcgacgtc    240
gaagtgttcc tggttgccac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcatacgacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
gcccgttttg ctaatgcgct ggtgtccctg ggctgttcac cggcagaaat gacctggaaa    660
gccggtgttg acgcactgag ttttggtgcg acgaaaaacg cgttctggc ggccgaagca    720
attgtcctgt caataccctc gctggctacg gaaatgagct atcgtcgcaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttcgtcgc    960
ctggattctg ccatgatcga cgcactgctg aaagctggct ttggcttcgg gtacaagcgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 160
<211> LENGTH: 376
<212> TYPE: PRT
<213> ORGANISM: Artificial sequence
<220> FEATURE:
<223> OTHER INFORMATION: Engineered sequence

<400> SEQUENCE: 160

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Phe Asp Glu Leu
 50                  55                  60

Thr Ala Gln Val Lys Arg Lys Phe Cys Glu Ile Phe Glu Arg Asp Val
 65                  70                  75                  80

Glu Val Phe Leu Val Ala Thr Gly Thr Ala Ala Asn Ala Leu Cys Leu
                 85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
370                 375

<210> SEQ ID NO 161
<211> LENGTH: 1128
<212> TYPE: DNA
<213> ORGANISM: Artificial sequence
<220> FEATURE:
<223> OTHER INFORMATION: Engineered sequence

<400> SEQUENCE: 161
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg ccaagctga cccttatggt   180

```
accgatgaac tgactgctca agttaaacgt aaattttgcg aaatcttcga acgcgacgtc      240
gaagtgttcc tggttccaac cggtacggca gcaaacgcac tgtgtctgtc cgcaatgacc      300
ccgccgtggg gtaatattta ctgccatcac gcgtcccaca tcaacaatga tgaatgtggt      360
gcgccggaat ttttctcaaa cggcgccaaa ctgatgaccg ttgatggtcc ggcagctaaa      420
ctggacattg tccgtctgcg cgaacgtacg cgcgaaaaag tgggtgatgt tcatacgacg      480
cagccggcat gcgtctctat tacccaagct acggaagtgg gcagtatcta taccctggat      540
gaaattgaag ccatcggtga cgtgtgcaaa tcatcgagcc tgggtctgca catggatggc      600
gcccgttttg ctaatgcgct ggtgtccctg ggctgttcac cggcagaaat gacctggaaa      660
gccggtgttg acgcactgag ttttggtgcg acgaaaaacg gcgttctggc ggccgaagca      720
attgtcctgt tcaataccct gctggctacg gaaatgagct atcgtcgcaa acgtgccggc      780
cacctgatca gtaaataccg ctttctgagc gctcagatcg atgcgtacct gaccgatgac      840
ctgtggctgc gtaacgcccg caaagcaaat gcagctgcgc agcgtctggc ccaaggtctg      900
gaaggcctgg gcggtgttga agtcctgggc ggtaccgaag caaacattct gttctgtcgc      960
ctggattctg ccatgatcga cgcactgctg aaagctggct ttggcttcgg gtacaagcgt     1020
tggggtccga acgtggttcg ctttgttacc agcttcgcta ccacggcgga agatgtggac     1080
cacctgctga atcaggttcg cctggccgca gaccgtacgc aagaacgc                  1128
```

<210> SEQ ID NO 162
<211> LENGTH: 376
<212> TYPE: PRT
<213> ORGANISM: Artificial sequence
<220> FEATURE:
<223> OTHER INFORMATION: Engineered sequence

<400> SEQUENCE: 162

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190
```

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Gly Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 163
<211> LENGTH: 1128
<212> TYPE: DNA
<213> ORGANISM: Artificial sequence
<220> FEATURE:
<223> OTHER INFORMATION: Engineered sequence

<400> SEQUENCE: 163
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180 accgatgaac tgactgctca agttaaacgt aaattttgcg aaatcttcga acgcgacgtc     240
gaagtgttcc tggttccaac cggtacggca gcaaacgcac tgtgtctgtc cgcaatgacc     300
ccgccgtggg gtaatatttt actgccatca cgcgtcccac atcaacaatga tgaatgtggt   360 gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcattcgacg    480
cagccggcat gcgtctctat tacccaagct acggaagtgg gcagtatcta taccctggat    540
gaaattgaag ccatcggtga cgtgtgcaaa tcatcgagcc tggtctgca catggatggc    600 gcccgttttg ctaatgcgct ggtgtccctg gctgttcac cggcagaaat gacctggaaa    660
gccggtgttg acgcactgag ttttggtgcg acgaaaaacg gcgttctggc ggccgaagca    720
attgtcctgt tcaatacctc gctggctacg gaaatgagct atcgtcgcaa acgtgccggc    780
cacctgatca gtaaataccg cttttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct ttaaattcgg gtacaagcgt   1020

```
tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 164
<211> LENGTH: 376
<212> TYPE: PRT
<213> ORGANISM: Artificial sequence
<220> FEATURE:
<223> OTHER INFORMATION: Engineered sequence

<400> SEQUENCE: 164

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
```

```
              340                 345                 350
Ala Thr Thr Ala Glu Asp Val Asp His Leu Leu Asn Gln Val Arg Leu
        355                 360                 365

Ala Ala Asp Arg Thr Gln Glu Arg
        370                 375

<210> SEQ ID NO 165
<211> LENGTH: 1128
<212> TYPE: DNA
<213> ORGANISM: Artificial sequence
<220> FEATURE:
<223> OTHER INFORMATION: Engineered sequence

<400> SEQUENCE: 165
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttgccac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg cgcgaaaaag tgggtgatgt tcatacgacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
gcccgttttg ctaatgcgct ggtgtccctg ggctgttcac cggcagaaat gacctggaaa     660
gccggtgttg acgcactgag ttttggtgcg acgaaaaacg cgttctggc ggccgaagca     720 attgtcctgt caataccctc gctggctacg gaaatgagct atcgtcgcaa cgtgccggc     780 cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacgagcgt    1020
tggggtccga acgtggttcg ctttgttacc agcttcgcta ccacggcgga agatgtggac    1080
cacctgctga atcaggttcg cctggccgca gaccgtacgc aagaacgc                 1128

<210> SEQ ID NO 166
<211> LENGTH: 376
<212> TYPE: PRT
<213> ORGANISM: Artificial sequence
<220> FEATURE:
<223> OTHER INFORMATION: Engineered sequence

<400> SEQUENCE: 166

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
```

```
                65                  70                  75                  80
Glu Val Phe Leu Val Ala Thr Gly Thr Ala Ala Asn Ala Leu Cys Leu
                    85                  90                  95

Ser Ala Met Thr Pro Pro Trp Gly Asn Ile Tyr Cys His His Ala Ser
                100                 105                 110

His Ile Asn Asn Asp Glu Cys Gly Ala Pro Glu Phe Phe Ser Asn Gly
                115                 120                 125

Ala Lys Leu Met Thr Val Asp Gly Pro Ala Ala Lys Leu Asp Ile Val
            130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
                180                 185                 190

Ser Leu Gly Leu His Met Asp Gly Ala Arg Phe Ala Asn Ala Leu Val
                195                 200                 205

Ser Leu Gly Cys Ser Pro Ala Glu Met Thr Trp Lys Ala Gly Val Asp
            210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
                260                 265                 270

Ile Asp Ala Tyr Leu Thr Asp Asp Leu Trp Leu Arg Asn Ala Arg Lys
                275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Glu Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
            355                 360                 365

Ala Ala Asp Arg Thr Gln Glu Arg
370                 375

<210> SEQ ID NO 167
<211> LENGTH: 1128
<212> TYPE: DNA
<213> ORGANISM: Artificial sequence
<220> FEATURE:
<223> OTHER INFORMATION: Engineered sequence

<400> SEQUENCE: 167
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg ccaagctga cccttatggt    180 accgatgaac tgactgctca agttaaacgt aaattttgcg aaatcttcga acgcgacgtc   240
gaagtgttcc tggttgccac cggtacggca gcaaacgcac tgtgtctgtc cgcaatgacc   300
```

-continued

```
ccgccgtggg gtaatattta ctgccatcac gcgtcccaca tcaacaatga tgaatgtggt      360
gcgccggaat ttttctcaaa cggcgccaaa ctgatgaccg ttgatggtcc ggcagctaaa      420
ctggacattg tccgtctgcg cgaacgtacg cgcgaaaaag tgggtgatgt tcattcgacg      480
cagccggcat gcgtctctat tacccaagct acggaagtgg gcagtatcta taccctggat      540
gaaattgaag ccatcggtga cgtgtgcaaa tcatcgagcc tgggtctgca catggatggc      600
gcccgttttg ctaatgcgct ggtgtccctg ggctgttcac cggcagaaat gacctggaaa      660
gccggtgttg acgcactgag ttttggtgcg acgaaaaacg gcgttctggc ggccgaagca      720
attgtcctgt tcaataccctc gctggctacg gaaatgagct atcgtcgcaa acgtgccggc      780
cacctgatca gtaaataccg ctttctgagc gctcagatcg atgcgtacct gaccgatgac      840
ctgtggctgc gtaacgcccg caaagcaaat gcagctgcgc agcgtctggc ccaaggtctg      900
gaaggcctgg gcggtgttga agtcctgggc ggtaccgaag caaacattct gttctgtcgc      960
ctggattctg ccatgatcga cgcactgctg aaagctggct ttaaattcgg gtacaagcgt     1020
tggggtccga acgtggttcg ctttgttacc agcttcgcta ccacggcgga agatgtggac     1080
cacctgctga atcaggttcg cctggccgca gaccgtacgc aagaacgc                  1128
```

<210> SEQ ID NO 168
<211> LENGTH: 376
<212> TYPE: PRT
<213> ORGANISM: Artificial sequence
<220> FEATURE:
<223> OTHER INFORMATION: Engineered sequence

<400> SEQUENCE: 168

```
Met Asn Gly Glu Thr Ser Arg Pro Pro Ala Leu Gly Phe Ser Ser Glu
1               5                  10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220
```

```
Ala Leu Ser Phe Gly Ala Thr Lys Asn Gly Val Leu Ala Glu Ala
225                 230                 235                 240

Ile Val Leu Phe Asn Thr Ser Leu Ala Thr Glu Met Ser Tyr Arg Arg
            245                 250                 255

Lys Arg Ala Gly His Leu Ile Ser Lys Tyr Arg Phe Leu Ser Ala Gln
        260                 265                 270

Ile Asp Ala Tyr Leu Thr Asp Asp Leu Trp Leu Arg Asn Ala Arg Lys
    275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
            325                 330                 335

Gly Tyr Lys Arg Trp Gly Pro Asn Val Val Arg Phe Val Thr Ser Phe
        340                 345                 350

Ala Thr Thr Ala Glu Asp Val Asp His Leu Leu Asn Gln Val Arg Leu
    355                 360                 365

Ala Ala Asp Arg Thr Gln Glu Arg
370                 375

<210> SEQ ID NO 169
<211> LENGTH: 1128
<212> TYPE: DNA
<213> ORGANISM: Artificial sequence
<220> FEATURE:
<223> OTHER INFORMATION: Engineered sequence

<400> SEQUENCE: 169
atgaacggtg aaacctcgcg tccgccggcg ctgggtttta gctctgaaaa tattgctggt        60
gcaagcccgg aagtcgcaca ggcactcgtt aagcacagtt cgggccaggc gggtccctat       120
ggcaccgacg agttgacggc acaggtcaag catagctccg ccaagctga cccttatggt       180 accgatgaac tgactgctca agttaaacgt aaattttgcg aaatcttcga acgcgacgtc       240
gaagtgttcc tggttgccac cggtacggca gcaaacgcac tgtgtctgtc cgcaatgacc       300
ccgccgtggg gtaatattta ctgccatcac gcgtcccaca tcaacaatga tgaatgtggt       360
gcgccggaat ttttctcaaa cggcgccaaa ctgatgaccg ttgatggtcc ggcagctaaa       420
ctggacattg tccgtctgcg cgaacgtacg cgcgaaaaag tgggtgatgt tcatacgacg       480
cagccggcat gcgtctctat tacccaagct acggaagtgg gcagtatcta taccctggat       540
gaaattgaag ccatcggtga cgtgtgcaaa tcatcgagcc tgggtctgca catggatggc       600
tcacgttttg ctaatgcgct ggtgtccctg ggctgttcac cggcagaaat gacctggaaa       660
gccggtgttg acgcactgag ttttggtgcg acgaaaaacg gcgttctggc ggccgaagca       720
attgtcctgt tcaataccte gctggctacg gaaatgagct atcgtcgcaa acgtgccggc       780
cacctgatca gtaaataccg ctttctgagc gctcagatcg atgcgtacct gaccgatgac       840
ctgtggctgc gtaacgcccg caaagcaaat gcagctgcgc agcgtctggc ccaaggtctg       900
gaaggcctgg gcggtgttga agtcctgggc ggtaccgaag caaacattct gttctgtcgc       960
ctggattctg ccatgatcga cgcactgctg aaagctggct ttaaattcgg gtacgagcgt      1020
tggggtccga acgtggttcg ctttgttacc agcttcgcta ccacggcgga agatgtggac      1080
cacctgctga atcaggttcg cctggccgca gaccgtacgc aagaacgc                   1128
```

<210> SEQ ID NO 170
<211> LENGTH: 376
<212> TYPE: PRT
<213> ORGANISM: Artificial sequence
<220> FEATURE:
<223> OTHER INFORMATION: Engineered sequence

<400> SEQUENCE: 170

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Glu Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365
```

Ala Ala Asp Arg Thr Gln Glu Arg
        370                 375

<210> SEQ ID NO 171
<211> LENGTH: 1128
<212> TYPE: DNA
<213> ORGANISM: Artificial sequence
<220> FEATURE:
<223> OTHER INFORMATION: Engineered sequence

<400> SEQUENCE: 171

| | | | | | |
|---|---|---|---|---|---|
| atgaacggtg | aaacctcgcg | tccgccggcg | ctgggtttta | gctctgaaaa | tattgctggt | 60 |
| gcaagcccgg | aagtcgcaca | ggcactcgtt | aagcacagtt | cgggccaggc | gggtccctat | 120 |
| ggcaccgacg | agttgacggc | acaggtcaag | catagctccg | gccaagctga | cccttatggt | 180 |
| accgatgaac | tgactgctca | agttaaacgt | aaattttgcg | aaatcttcga | acgcgacgtc | 240 |
| gaagtgttcc | tggttccaac | cggtacggca | gcaaacgcac | tgtgtctgtc | cgcaatgacc | 300 |
| ccgccgtggg | gtaatattta | ctgccatcac | gcgtcccaca | tcaacaatga | tgaatgtggt | 360 |
| gcgccggaat | ttttctcaaa | cggcgccaaa | ctgatgaccg | ttgatggtcc | ggcagctaaa | 420 |
| ctggacattg | tccgtctgcg | cgaacgtacg | cgcgaaaaag | tgggtgatgt | tcatacgacg | 480 |
| cagccggcat | gcgtctctat | tacccaagct | acggaagtgg | gcagtatcta | taccctggat | 540 |
| gaaattgaag | ccatcggtga | cgtgtgcaaa | tcatcgagcc | tgggtctgca | catggatggc | 600 |
| gcccgttttg | ctaatgcgct | ggtgtccctg | ggctgttcac | cggcagaaat | gacctggaaa | 660 |
| gccggtgttg | acgcactgag | ttttggtgcg | acgaaaaacg | gcgttctggc | ggccgaagca | 720 |
| attgtcctgt | tcaataccctc | gctggctacg | gaaatgagct | atcgtcgcaa | acgtgccggc | 780 |
| cacctgatca | gtaaataccg | ctttctgagc | gctcagatcg | atgcgtacct | gaccgatgac | 840 |
| ctgtggctgc | gtaacgcccg | caaagcaaat | gcagctgcgc | agcgtctggc | ccaaggtctg | 900 |
| gaaggcctgg | gcggtgttga | agtcctgggc | ggtaccgaag | caaacattct | gttctgtcgc | 960 |
| ctggattctg | ccatgatcga | cgcactgctg | aaagctggct | ttcgcttcgg | gtacaagcgt | 1020 |
| tggggtccga | acgtggttcg | ctttgttacc | agcttcgcta | ccacggcgga | agatgtggac | 1080 |
| cacctgctga | atcaggttcg | cctggccgca | gaccgtacgc | aagaacgc | | 1128 |

<210> SEQ ID NO 172
<211> LENGTH: 376
<212> TYPE: PRT
<213> ORGANISM: Artificial sequence
<220> FEATURE:
<223> OTHER INFORMATION: Engineered sequence

<400> SEQUENCE: 172

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

```
Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Arg Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 173
<211> LENGTH: 1128
<212> TYPE: DNA
<213> ORGANISM: Artificial sequence
<220> FEATURE:
<223> OTHER INFORMATION: Engineered sequence

<400> SEQUENCE: 173
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggcaccgacg agttgacggc acaggtcaag catagctccg ccaagctga cccttatggt     180 accgatgaac tgactgctca agttaaacgt aaattttgcg aaatcttcga acgcgacgtc    240
gaagtgttcc tggttggaac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg cgcgaaaaag tgggtgatgt tcattcgacg    480
```

```
cagccggcat gcgtctctat tacccaagct acggaagtgg gcagtatcta taccctggat   540
gaaattgaag ccatcggtga cgtgtgcaaa tcatcgagcc tgggtctgca catggatggc   600
tcacgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaataccct gctggctacg gaaatgagct atcgtcgcaa acgtgccggc   780
cacctgatca gtaaataccg ctttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttcgcttcgg gtacaagcgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 174
<211> LENGTH: 376
<212> TYPE: PRT
<213> ORGANISM: Artificial sequence
<220> FEATURE:
<223> OTHER INFORMATION: Engineered sequence

<400> SEQUENCE: 174

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Gly Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Arg Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
```

```
                245                 250                 255
Lys Arg Ala Gly His Leu Ile Ser Lys Tyr Arg Phe Leu Ser Ala Gln
            260                 265                 270

Ile Asp Ala Tyr Leu Thr Asp Leu Trp Leu Arg Asn Ala Arg Lys
            275                 280                 285

Ala Asn Ala Ala Ala Gln Arg Leu Ala Gln Gly Leu Glu Gly Leu Gly
            290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Arg Phe
                325                 330                 335

Gly Tyr Lys Arg Trp Gly Pro Asn Val Val Arg Phe Val Thr Ser Phe
                340                 345                 350

Ala Thr Thr Ala Glu Asp Val Asp His Leu Leu Asn Gln Val Arg Leu
                355                 360                 365

Ala Ala Asp Arg Thr Gln Glu Arg
                370                 375
```

<210> SEQ ID NO 175
<211> LENGTH: 1128
<212> TYPE: DNA
<213> ORGANISM: Artificial sequence
<220> FEATURE:
<223> OTHER INFORMATION: Engineered sequence

<400> SEQUENCE: 175

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctgac ccttatggt     180
accgatgaac tgactgctca agttaaacgt aaattttgcg aaatcttcga acgcgacgtc     240
gaagtgttcc tggttgcaac cggtacggca gcaaacgcac tgtgtctgtc cgcaatgacc     300
ccgccgtggg gtaatatttt actgccatca cgcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg tccgaaaaag tgggtgatgt tcattccacg     480
cagccggcat gcgtctctat taccccaagct acggaagtgg gcagtatcta taccctggat     540
gaaattgaag ccatcggtga cgtgtgcaaa tcatcgagcc tgggtctgca catggatggc     600
agccgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcacaa acgtgccggc     780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacaaacgt    1020
tggggtccga acgtggttcg ctttgttacc agcttcgcta ccacggcgga agatgtggac    1080
cacctgctga atcaggttcg cctggccgca gaccgtacgc aagaacgc                 1128
```

<210> SEQ ID NO 176
<211> LENGTH: 376
<212> TYPE: PRT
<213> ORGANISM: Artificial sequence
<220> FEATURE:
<223> OTHER INFORMATION: Engineered sequence

<400> SEQUENCE: 176

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Ser Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ser Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg His
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 177

<211> LENGTH: 1128
<212> TYPE: DNA
<213> ORGANISM: Artificial sequence
<220> FEATURE:
<223> OTHER INFORMATION: Engineered sequence

<400> SEQUENCE: 177

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg gccaagctga cccttatggt     180
accgatgaac tgactgctca agttaaacgt aaattttgcg aaatcttcga acgcgacgtc     240
gaagtgttcc tggttgcaac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg tccgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
gcgcgttttg ctaatgcgct ggtgtccctg ggctgttcac cggcagaaat gacctggaaa     660
gccggtgttg acgcactgag ttttggtgcg acgaaaaacg gcgttctggc ggccgaagca     720
attgtcctgt tcaatacctc gctggctacg gaaatgagct atcgtcgtaa cgtgccggc      780
cacctgatca gtaaataccg ctttctgagc gctcagatcg atgcgtacct gaccgatgac     840
ctgtggctgc gtaacgcccg caaagcaaat gcagctgcgc agcgtctggc ccaaggtctg     900
gaaggcctgg gcggtgttga agtcctgggc ggtaccgaag caaacattct gttctgtcgc     960
ctggattctg ccatgatcga cgcactgctg aaagctggct ttaaattcgg gtacaaacgt    1020
tggggtccga acgtggttcg ctttgttacc agcttcgcta ccacggcgga agatgtggac    1080
cacctgctga atcaggttcg cctggccgca gaccgtacgc aagaacgc                1128
```

<210> SEQ ID NO 178
<211> LENGTH: 376
<212> TYPE: PRT
<213> ORGANISM: Artificial sequence
<220> FEATURE:
<223> OTHER INFORMATION: Engineered sequence

<400> SEQUENCE: 178

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Ala Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125
```

```
Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 179
<211> LENGTH: 1128
<212> TYPE: DNA
<213> ORGANISM: Artificial sequence
<220> FEATURE:
<223> OTHER INFORMATION: Engineered sequence

<400> SEQUENCE: 179
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat     120
ggcaccgacg agttgacggc acaggtcaag catagctccg ccaagctga cccttatggt      180 accgatgaac tgactgctca agttaaacgt aaattttgcg aaatcttcga acgcgacgtc     240
gaagtgttcc tggttcctac cggtacggca gcaaacgcac tgtgtctgtc cgcaatgacc     300
ccgccgtggg gtaatattta ctgccatcac gcgtcccaca tcaacaatga tgaatgtggt     360
gcgccggaat ttttctcaaa cggcgccaaa ctgatgaccg ttgatggtcc ggcagctaaa     420
ctggacattg tccgtctgcg cgaacgtacg tccgaaaaag tgggtgatgt tcataccacg     480
cagccggcat gcgtctctat tacccaagct acggaagtgg gcagtatcta taccctggat     540
gaaattgaag ccatcggtga cgtgtgcaaa tcatcgagcc tgggtctgca catggatggc     600
```

```
gcgcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccct gctggctacg gaaatgagct atcgtcacaa acgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct taaaattcgg gtacaaacgt   1020
tggggtccga acgtggttcg ctttgttacc agcttcgcta ccacggcgga agatgtggac   1080
cacctgctga atcaggttcg cctggccgca gaccgtacgc aagaacgc               1128
```

<210> SEQ ID NO 180
<211> LENGTH: 376
<212> TYPE: PRT
<213> ORGANISM: Artificial sequence
<220> FEATURE:
<223> OTHER INFORMATION: Engineered sequence

<400> SEQUENCE: 180

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys His Ser Ser Gly Gln Ala Asp Pro Tyr Gly Thr Asp Glu Leu
    50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Thr Thr
145                 150                 155                 160

Gln Pro Ala Cys Val Ser Ile Thr Gln Ala Thr Glu Val Gly Ser Ile
                165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg His
                245                 250                 255

Lys Arg Ala Gly His Leu Ile Ser Lys Tyr Arg Phe Leu Ser Ala Gln
            260                 265                 270
```

```
Ile Asp Ala Tyr Leu Thr Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375
```

<210> SEQ ID NO 181
<211> LENGTH: 1128
<212> TYPE: DNA
<213> ORGANISM: Artificial sequence
<220> FEATURE:
<223> OTHER INFORMATION: Engineered sequence

<400> SEQUENCE: 181

```
atgaacggtg aaacctcgcg tccgccggcg ctgggtttta gctctgaaaa tattgctggt      60
gcaagcccgg aagtcgcaca ggcactcgtt aagcacagtt cgggccaggc gggtccctat    120
ggcaccgacg agttgacggc acaggtcaag catagctccg ccaagctga cccttatggt     180
accgatgaac tgactgctca agttaaacgt aaattttgcg aaatcttcga acgcgacgtc    240
gaagtgttcc tggttgcaac cggtacggca gcaaacgcac tgtgtctgtc cgcaatgacc    300
ccgccgtggg gtaatattta ctgccatcac gcgtcccaca tcaacaatga tgaatgtggt    360
gcgccggaat ttttctcaaa cggcgccaaa ctgatgaccg ttgatggtcc ggcagctaaa    420
ctggacattg tccgtctgcg cgaacgtacg tccgaaaaag tgggtgatgt tcattccacg    480
cagccggcat gcgtctctat tacccaagct acggaagtgg gcagtatcta taccctggat    540
gaaattgaag ccatcggtga cgtgtgcaaa tcatcgagcc tgggtctgca catggatggc    600
gcgcgttttg ctaatgcgct ggtgtccctg ggctgttcac cggcagaaat gacctggaaa    660
gccggtgttg acgcactgag ttttggtgcg acgaaaaacg gcgttctggc ggccgaagca    720
attgtcctgt tcaataccct gctggctacg gaaatgagct atcgtcacaa cgtgccggc    780
cacctgatca gtaaataccg ctttctgagc gctcagatcg atgcgtacct gaccgatgac    840
ctgtggctgc gtaacgcccg caaagcaaat gcagctgcgc agcgtctggc ccaaggtctg    900
gaaggcctgg gcggtgttga agtcctgggc ggtaccgaag caaacattct gttctgtcgc    960
ctggattctg ccatgatcga cgcactgctg aaagctggct taaaattcgg gtacaaacgt   1020
tggggtccga acgtggttcg ctttgttacc agcttcgcta ccacggcgga agatgtggac   1080
cacctgctga atcaggttcg cctggccgca gaccgtacgc aagaacgc                1128
```

<210> SEQ ID NO 182
<211> LENGTH: 376
<212> TYPE: PRT
<213> ORGANISM: Artificial sequence
<220> FEATURE:
<223> OTHER INFORMATION: Engineered sequence

<400> SEQUENCE: 182

```
Met Asn Gly Glu Thr Ser Arg Pro Pro Ala Leu Gly Phe Ser Ser Glu
 1               5                  10                  15
Asn Ile Ala Gly Ala Ser Pro Glu Val Ala Gln Ala Leu Val Lys His
                20                  25                  30
Ser Ser Gly Gln Ala Gly Pro Tyr Gly Thr Asp Glu Leu Thr Ala Gln
            35                  40                  45
Val Lys His Ser Ser Gly Gln Ala Asp Pro Tyr Gly Thr Asp Glu Leu
 50                  55                  60
Thr Ala Gln Val Lys Arg Lys Phe Cys Glu Ile Phe Glu Arg Asp Val
 65                  70                  75                  80
Glu Val Phe Leu Val Ala Thr Gly Thr Ala Ala Asn Ala Leu Cys Leu
                85                  90                  95
Ser Ala Met Thr Pro Pro Trp Gly Asn Ile Tyr Cys His His Ala Ser
            100                 105                 110
His Ile Asn Asn Asp Glu Cys Gly Ala Pro Glu Phe Phe Ser Asn Gly
            115                 120                 125
Ala Lys Leu Met Thr Val Asp Gly Pro Ala Ala Lys Leu Asp Ile Val
 130                 135                 140
Arg Leu Arg Glu Arg Thr Ser Glu Lys Val Gly Asp Val His Ser Thr
145                 150                 155                 160
Gln Pro Ala Cys Val Ser Ile Thr Gln Ala Thr Glu Val Gly Ser Ile
                165                 170                 175
Tyr Thr Leu Asp Glu Ile Glu Ala Ile Gly Asp Val Cys Lys Ser Ser
            180                 185                 190
Ser Leu Gly Leu His Met Asp Gly Ala Arg Phe Ala Asn Ala Leu Val
            195                 200                 205
Ser Leu Gly Cys Ser Pro Ala Glu Met Thr Trp Lys Ala Gly Val Asp
 210                 215                 220
Ala Leu Ser Phe Gly Ala Thr Lys Asn Gly Val Leu Ala Ala Glu Ala
 225                 230                 235                 240
Ile Val Leu Phe Asn Thr Ser Leu Ala Thr Glu Met Ser Tyr Arg His
                245                 250                 255
Lys Arg Ala Gly His Leu Ile Ser Lys Tyr Arg Phe Leu Ser Ala Gln
                260                 265                 270
Ile Asp Ala Tyr Leu Thr Asp Asp Leu Trp Leu Arg Asn Ala Arg Lys
            275                 280                 285
Ala Asn Ala Ala Ala Gln Arg Leu Ala Gln Gly Leu Glu Gly Leu Gly
 290                 295                 300
Gly Val Glu Val Leu Gly Gly Thr Glu Ala Asn Ile Leu Phe Cys Arg
305                 310                 315                 320
Leu Asp Ser Ala Met Ile Asp Ala Leu Leu Lys Ala Gly Phe Lys Phe
                325                 330                 335
Gly Tyr Lys Arg Trp Gly Pro Asn Val Val Arg Phe Val Thr Ser Phe
                340                 345                 350
Ala Thr Thr Ala Glu Asp Val Asp His Leu Leu Asn Gln Val Arg Leu
            355                 360                 365
Ala Ala Asp Arg Thr Gln Glu Arg
 370                 375

<210> SEQ ID NO 183
<211> LENGTH: 1128
<212> TYPE: DNA
<213> ORGANISM: Artificial sequence
<220> FEATURE:
<223> OTHER INFORMATION: Engineered sequence
```

<400> SEQUENCE: 183

```
atgaacggtg aaacctcgcg tccgccggcg ctgggtttta gctctgaaaa tattgctggt    60
gcaagcccgg aagtcgcaca ggcactcgtt aagcacagtt cgggccaggc gggtccctat   120
ggcaccgacg agttgacggc acaggtcaag catagctccg gccaagctga cccttatggt   180
accgatgaac tgactgctca agttaaacgt aaattttgcg aaatcttcga acgcgacgtc   240
gaagtgttcc tggttcctac cggtacggca gcaaacgcac tgtgtctgtc cgcaatgacc   300
ccgccgtggg gtaatattta ctgccatcac gcgtcccaca tcaacaatga tgaatgtggt   360
gcgccggaat ttttctcaaa cggcgccaaa ctgatgaccg ttgatggtcc ggcagctaaa   420
ctggacattg tccgtctgcg cgaacgtacg tccgaaaaag tgggtgatgt tcataccacg   480
cagccggcat gcgtctctat tacccaagct acggaagtgg gcagtatcta taccctggat   540
gaaattgaag ccatcggtga cgtgtgcaaa tcatcgagcc tgggtctgca catggatggc   600
gcgcgttttg ctaatgcgct ggtgtccctg ggctgttcac cggcagaaat gacctggaaa   660
gccggtgttg acgcactgag ttttggtgcg acgaaaaacg gcgttctggc ggccgaagca   720
attgtcctgt tcaatacctc gctggctacg gaaatgagct atcgtcgtaa acgtgccggc   780
cacctgatca gtaaataccg cttttctgagc gctcagatcg atgcgtacct gaccgatgac   840
ctgtggctgc gtaacgcccg caaagcaaat gcagctgcgc agcgtctggc ccaaggtctg   900
gaaggcctgg gcggtgttga agtcctgggc ggtaccgaag caaacattct gttctgtcgc   960
ctggattctg ccatgatcga cgcactgctg aaagctggct ttaaattcgg gtacaaacgt  1020
tggggtccga acgtggttcg ctttgttacc agcttcgcta ccacggcgga agatgtggac  1080
cacctgctga atcaggttcg cctggccgca gaccgtacgc aagaacgc              1128
```

<210> SEQ ID NO 184
<211> LENGTH: 376
<212> TYPE: PRT
<213> ORGANISM: Artificial sequence
<220> FEATURE:
<223> OTHER INFORMATION: Engineered sequence

<400> SEQUENCE: 184

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
                20                  25                  30

Ser Ser Gly Gln Ala Gly Pro Tyr Gly Thr Asp Glu Leu Thr Ala Gln
            35                  40                  45

Val Lys His Ser Ser Gly Gln Ala Asp Pro Tyr Gly Thr Asp Glu Leu
        50                  55                  60

Thr Ala Gln Val Lys Arg Lys Phe Cys Glu Ile Phe Glu Arg Asp Val
65                  70                  75                  80

Glu Val Phe Leu Val Pro Thr Gly Thr Ala Ala Asn Ala Leu Cys Leu
                85                  90                  95

Ser Ala Met Thr Pro Pro Trp Gly Asn Ile Tyr Cys His His Ala Ser
            100                 105                 110

His Ile Asn Asn Asp Glu Cys Gly Ala Pro Glu Phe Phe Ser Asn Gly
        115                 120                 125

Ala Lys Leu Met Thr Val Asp Gly Pro Ala Ala Lys Leu Asp Ile Val
    130                 135                 140

Arg Leu Arg Glu Arg Thr Ser Glu Lys Val Gly Asp Val His Thr Thr
```

```
                145                 150                 155                 160
Gln Pro Ala Cys Val Ser Ile Thr Gln Ala Thr Glu Val Gly Ser Ile
                    165                 170                 175

Tyr Thr Leu Asp Glu Ile Glu Ala Ile Gly Asp Val Cys Lys Ser Ser
            180                 185                 190

Ser Leu Gly Leu His Met Asp Gly Ala Arg Phe Ala Asn Ala Leu Val
        195                 200                 205

Ser Leu Gly Cys Ser Pro Ala Glu Met Thr Trp Lys Ala Gly Val Asp
    210                 215                 220

Ala Leu Ser Phe Gly Ala Thr Lys Asn Gly Val Leu Ala Ala Glu Ala
225                 230                 235                 240

Ile Val Leu Phe Asn Thr Ser Leu Ala Thr Glu Met Ser Tyr Arg Arg
                245                 250                 255

Lys Arg Ala Gly His Leu Ile Ser Lys Tyr Arg Phe Leu Ser Ala Gln
            260                 265                 270

Ile Asp Ala Tyr Leu Thr Asp Asp Leu Trp Leu Arg Asn Ala Arg Lys
        275                 280                 285

Ala Asn Ala Ala Ala Gln Arg Leu Ala Gln Gly Leu Glu Gly Leu Gly
    290                 295                 300

Gly Val Glu Val Leu Gly Gly Thr Glu Ala Asn Ile Leu Phe Cys Arg
305                 310                 315                 320

Leu Asp Ser Ala Met Ile Asp Ala Leu Leu Lys Ala Gly Phe Lys Phe
                325                 330                 335

Gly Tyr Lys Arg Trp Gly Pro Asn Val Val Arg Phe Val Thr Ser Phe
            340                 345                 350

Ala Thr Thr Ala Glu Asp Val Asp His Leu Leu Asn Gln Val Arg Leu
        355                 360                 365

Ala Ala Asp Arg Thr Gln Glu Arg
    370                 375

<210> SEQ ID NO 185
<211> LENGTH: 1071
<212> TYPE: DNA
<213> ORGANISM: Artificial sequence
<220> FEATURE:
<223> OTHER INFORMATION: Engineered sequence

<400> SEQUENCE: 185
atgaacggtg aaacctcgcg tccgccggcg ctgggtttta gctctgataa tattgctggt       60
gcaagcccgg aagtcgcaca ggcactcgtt aagcacagtt cgggccaggc gggtccctat      120
tttaccgacg agttgacggc acaggtcaag cgtaaatttt gcgaaatctt cgaacgcgac      180
gtcgaagtgt tcctggttcc gaccggtacg gcagcaaacg cactgtgtct gtccgcaatg      240
accccgccgt ggggtaatat ttactgccat ccggcgtccc acatcaacaa tgatgaatgt      300
ggtgcgccgg aatttttctc aaacggcgcc aaactgatga ccgttgatgg tccggcagct      360
aaactggaca ttgtccgtct gcgcgaacgt acgcgcgaaa aagtgggtga tgttcatacc      420
acgcagccgg catgcgtctc tattacccaa gctacggaag tgggcagtat ctataccctg      480
gatgaaattg aagccatcgg tgacgtgtgc aaatcatcga gcctgggtct gcacatggat      540
ggctctcgtt ttgctaatgc gctggtgtcc ctgggctgtt caccggcaga aatgacctgg      600
aaagccggtg ttgacgcact gagttttggt gcgacgaaaa acggcgttct ggcggccgaa      660
gcaattgtcc tgttcaatac ctcgctggct acggaaatga gctatcgtcg caaacgtgcc      720
ggccacctgt ctagtaaaat cgcctttctg agcgctcaga tcgatgcgta cctgaccgat      780
```

```
gacctgtggc tgcgtaacgc ccgcaaagca aatgcagctg cgcagcgtct ggcccaaggt    840
ctggaaggcc tgggcggtgt tgaagtcctg ggcggtaccg aagcaaacat tctgttctgt    900
cgcctggatt ctgccatgat cgacgcactg ctgaaagctg gctttggttt ctatcatgat    960
cgttggggtc cgaacgtggt tcgctttgtt accagcttcg ctaccacggc ggaagatgtg   1020
gaccacctgc tgaatcaggt tcgcctggcc gcagaccgta cgcaagaacg c            1071
```

<210> SEQ ID NO 186
<211> LENGTH: 357
<212> TYPE: PRT
<213> ORGANISM: Artificial sequence
<220> FEATURE:
<223> OTHER INFORMATION: Engineered sequence

<400> SEQUENCE: 186

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Phe Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
```

```
305                 310                 315                 320
Arg Trp Gly Pro Asn Val Val Arg Phe Val Thr Ser Phe Ala Thr Thr
                325                 330                 335
Ala Glu Asp Val Asp His Leu Leu Asn Gln Val Arg Leu Ala Ala Asp
                340                 345                 350
Arg Thr Gln Glu Arg
        355
```

<210> SEQ ID NO 187
<211> LENGTH: 1071
<212> TYPE: DNA
<213> ORGANISM: Artificial sequence
<220> FEATURE:
<223> OTHER INFORMATION: Engineered sequence

<400> SEQUENCE: 187

```
atgaacggtg aaacctcgcg tccgccggcg ctgggttta gctctgataa tattgctggt      60
gcaagcccgg aagtcgcaca ggcactcgtt aagcacagtt cgggccaggc gggtccctat    120
cagaccgacg agttgacggc acaggtcaag cgtaaatttt gcgaaatctt cgaacgcgac    180
gtcgaagtgt tcctggttcc gaccggtacg gcagcaaacg cactgtgtct gtccgcaatg    240
accccgccgt ggggtaatat ttactgccat ccggcgtccc acatcaacaa tgatgaatgt    300
ggtgcgccgg aatttttctc aaacggcgcc aaactgatga ccgttgatgg tccggcagct    360
aaactggaca ttgtccgtct gcgcgaacgt acgcgcgaaa agtgggtga tgttcatacc     420
acgcagccgg catgcgtctc tattacccaa gctacggaag tgggcagtat ctataccctg    480
gatgaaattg aagccatcgg tgacgtgtgc aaatcatcga gcctgggtct gcacatggat    540
ggctctcgtt ttgctaatgc gctggtgtcc ctgggctgtt caccggcaga atgacctgg     600
aaagccggtg ttgacgcact gagttttggt gcgacgaaaa acggcgttct ggcggccgaa    660
gcaattgtcc tgttcaatac ctcgctggct acggaaatga gctatcgtcg caaacgtgcc    720
ggccacctgt ctagtaaaat gcgctttctg agcgctcaga tcgatgcgta cctgaccgat    780
gacctgtggc tgcgtaacgc ccgcaaagca aatgcagctg cgcagcgtct ggcccaaggt    840
ctggaaggcc tgggcggtgt tgaagtcctg ggcggtaccg aagcaaacat tctgttctgt    900
cgcctggatt ctgccatgat cgacgcactg ctgaaagctg ctttggttt ctatcatgat    960
cgttggggtc cgaacgtggt tcgctttgtt accagcttcg ctaccacggc ggaagatgtg   1020
gaccacctgc tgaatcaggt tcgcctggcc gcagaccgta cgcaagaacg c            1071
```

<210> SEQ ID NO 188
<211> LENGTH: 357
<212> TYPE: PRT
<213> ORGANISM: Artificial sequence
<220> FEATURE:
<223> OTHER INFORMATION: Engineered sequence

<400> SEQUENCE: 188

```
Met Asn Gly Glu Thr Ser Arg Pro Pro Ala Leu Gly Phe Ser Ser Asp
1               5                  10                  15
Asn Ile Ala Gly Ala Ser Pro Glu Val Ala Gln Ala Leu Val Lys His
            20                  25                  30
Ser Ser Gly Gln Ala Gly Pro Tyr Gln Thr Asp Glu Leu Thr Ala Gln
        35                  40                  45
Val Lys Arg Lys Phe Cys Glu Ile Phe Glu Arg Asp Val Glu Val Phe
    50                  55                  60
```

Leu Val Pro Thr Gly Thr Ala Ala Asn Ala Leu Cys Leu Ser Ala Met
 65                  70                  75                  80

Thr Pro Pro Trp Gly Asn Ile Tyr Cys His Pro Ala Ser His Ile Asn
                 85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Leu Gly
                165                 170                 175

Leu His Met Asp Gly Ser Arg Phe Ala Asn Ala Leu Val Ser Leu Gly
                180                 185                 190

Cys Ser Pro Ala Glu Met Thr Trp Lys Ala Gly Val Asp Ala Leu Ser
            195                 200                 205

Phe Gly Ala Thr Lys Asn Gly Val Leu Ala Ala Glu Ala Ile Val Leu
210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
                260                 265                 270

Ala Ala Gln Arg Leu Ala Gln Gly Leu Glu Gly Leu Gly Gly Val Glu
            275                 280                 285

Val Leu Gly Gly Thr Glu Ala Asn Ile Leu Phe Cys Arg Leu Asp Ser
        290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 189
<211> LENGTH: 1071
<212> TYPE: DNA
<213> ORGANISM: Artificial sequence
<220> FEATURE:
<223> OTHER INFORMATION: Engineered sequence

<400> SEQUENCE: 189
atgaacggtg aaacctcgcg tccgccggcg ctgggtttta gctctgataa tattgctggt      60
gcaagcccgg aagtcgcaca ggcactcgtt aagcacagtt cgggccaggc gggtccctat     120
cataccgacg agttgacggc acaggtcaag cgtaaatttt gcgaaatctt cgaacgcgac     180
gtcgaagtgt tcctggttcc gaccggtacg gcagcaaacg cactgtgtct gtccgcaatg     240
accccgccgt ggggtaatat ttactgccat ccggcgtccc acatcaacaa tgatgaatgt     300
ggtgcgccgg aatttttctc aaacggcgcc aaactgatga ccgttgatgg tccggcagct     360

```
aaactggaca ttgtccgtct gcgcgaacgt acgcgcgaaa aagtgggtga tgttcatacc    420
acgcagccgg catgcgtctc tattacccaa gctacggaag tgggcagtat ctatacccctg   480
gatgaaattg aagccatcgg tgacgtgtgc aaatcatcga gcctgggtct gcacatggat    540
ggctctcgtt ttgctaatgc gctggtgtcc ctgggctgtt caccggcaga atgacctgg     600
aaagccggtg ttgacgcact gagttttggt gcgacgaaaa acggcgttct ggcggccgaa    660
gcaattgtcc tgttcaatac ctcgctggct acggaaatga gctatcgtcg caaacgtgcc    720
ggccacctgt ctagtaaaat gcgctttctg agcgctcaga tcgatgcgta cctgaccgat    780
gacctgtggc tgcgtaacgc ccgcaaagca aatgcagctg cgcagcgtct ggcccaaggt    840
ctggaaggcc tgggcggtgt tgaagtcctg ggcggtaccg aagcaaacat tctgttctgt    900
cgcctggatt ctgccatgat cgacgcactg ctgaaagctg gctttggttt ctatcatgat    960
cgttggggtc cgaacgtggt tcgctttgtt accagcttcg ctaccacggc ggaagatgtg   1020
gaccacctgc tgaatcaggt tcgcctggcc gcagaccgta cgcaagaacg c            1071
```

<210> SEQ ID NO 190  
<211> LENGTH: 357  
<212> TYPE: PRT  
<213> ORGANISM: Artificial sequence  
<220> FEATURE:  
<223> OTHER INFORMATION: Engineered sequence

<400> SEQUENCE: 190

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr His Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240
```

```
Gly His Leu Ser Ser Lys Met Arg Phe Leu Ser Ala Gln Ile Asp Ala
            245                 250                 255

Tyr Leu Thr Asp Asp Leu Trp Leu Arg Asn Ala Arg Lys Ala Asn Ala
        260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
        290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 191
<211> LENGTH: 1071
<212> TYPE: DNA
<213> ORGANISM: Artificial sequence
<220> FEATURE:
<223> OTHER INFORMATION: Engineered sequence

<400> SEQUENCE: 191
atgaacggtg aaacctcgcg tccgccggcg ctgggttta gctctgataa tattgctggt    60
gcaagcccgg aagtcgcaca ggcactcgtt aagcacagtt cgggccaggc gggtccttat   120
ggtaccgatg acctgactgc tcaagttaaa cgtaaatttt gcgaaatctt cgaacgcgac   180
gtcgaagtgt tcctggttcc gaccggtacg gcagcaaacg cactgtgtct gtccgcaatg   240
accccgccgt ggggtaatat ttactgccat ccggcgtccc acatcaacaa tgatgaatgt   300
ggtgcgccga aattttctc aaacggcgcc aaactgatga ccgttgatgg tccggcagct   360
aaactggaca ttgtccgtct gcgcgaacgt acgcgcgaaa agtgggtga tgttcatacc   420 acgcagccgg catgcgtctc tattacccaa gctacggaag tgggcagtat ctataccctg   480
gatgaaattg aagccatcgg tgacgtgtgc aaatcatcga gcctgggtct gcacatggat   540
ggctctcgtt ttgctaatgc gctggtgtcc ctgggctgtt caccggcaga atgacctgg   600 aaagccggtg ttgacgcact gagttttggt gcgacgaaaa acggcgttct ggcggccgaa   660
gcaattgtcc tgttcaatac ctcgctggct acggaaatga gctatcgtcg caaacgtgcc   720
ggccacctga cgagtaaata ccgctttctg agcgctcaga tcgatgcgta cctgaccgat   780
gacctgtggc tgcgtaacgc ccgcaaagca aatgcagctg cgcagcgtct ggcccaaggt   840
ctggaaggcc tgggcggtgt tgaagtcctg ggcggtaccg aagcaaacat tctgttctgt   900
cgcctggatt ctgccatgat cgacgcactg ctgaaagctg ctttggttt cgggacgaag   960 cgttggggtc cgaacgtggt tcgctttgtt accagcttcg ctaccacggc ggaagatgtg  1020
gaccacctgc tgaatcaggt tcgcctggcc gcagaccgta cgcaagaacg c            1071

<210> SEQ ID NO 192
<211> LENGTH: 357
<212> TYPE: PRT
<213> ORGANISM: Artificial sequence
<220> FEATURE:
<223> OTHER INFORMATION: Engineered sequence

<400> SEQUENCE: 192
```

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Asp Leu Thr Ala Gln
            35                  40                  45

Val Lys Arg Lys Phe Cys Glu Ile Phe Glu Arg Asp Val Glu Val Phe
50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
            85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
            115                 120                 125

Glu Arg Thr Arg Glu Lys Val Gly Asp Val His Thr Thr Gln Pro Ala
            130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
            165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
            195                 200                 205

Phe Gly Ala Thr Lys Asn Gly Val Leu Ala Ala Glu Ala Ile Val Leu
            210                 215                 220

Phe Asn Thr Ser Leu Ala Thr Glu Met Ser Tyr Arg Arg Lys Arg Ala
225                 230                 235                 240

Gly His Leu Thr Ser Lys Tyr Arg Phe Leu Ser Ala Gln Ile Asp Ala
            245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
            275                 280                 285

Val Leu Gly Gly Thr Glu Ala Asn Ile Leu Phe Cys Arg Leu Asp Ser
            290                 295                 300

Ala Met Ile Asp Ala Leu Leu Lys Ala Gly Phe Gly Phe Gly Thr Lys
305                 310                 315                 320

Arg Trp Gly Pro Asn Val Val Arg Phe Val Thr Ser Phe Ala Thr Thr
            325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 193
<211> LENGTH: 1071
<212> TYPE: DNA
<213> ORGANISM: Artificial sequence
<220> FEATURE:
<223> OTHER INFORMATION: Engineered sequence

<400> SEQUENCE: 193

```
atgaacggtg aaacctcgcg tccgccggcg ctgggtttta gctctgataa tattgctggt    60
gcaagcccgg aagtcgcaca ggcactcgtt aagcacagtt cgggccaggc gggtccctat   120
ggtaccgatg aattcactgc tcaagttaaa cgtaaatttt gcgaaatctt cgaacgcgac   180
gtcgaagtgt tcctggttcc gaccggtacg gcagcaaacg cactgtgtct gtccgcaatg   240
accccgccgt ggggtaatat ttactgccat ccggcgtccc acatcaacaa tgatgaatgt   300
ggtgcgccga attttttctc aaacggcgcc aaactgatga ccgttgatgg tccggcagct   360
aaactggaca ttgtccgtct gcgcgaacgt acgcgcgaaa aagtgggtga tgttcatacc   420
acgcagccgg catgcgtctc tattacccaa gctacggaag tgggcagtat ctataccctg   480
gatgaaattg aagccatcgg tgacgtgtgc aaatcatcga gcctgggtct gcacatggat   540
ggctctcgtt ttgctaatgc gctggtgtcc ctgggctgtt caccggcaga aatgacctgg   600
aaagccggtg ttgacgcact gagttttggt gcgacgaaaa acggcgttct ggcggccgaa   660
gcaattgtcc tgttcaatac ctcgctggct acggaaatga gctatcgtcg caaacgtgcc   720
ggccacctga cgagtaaata ccgctttctg agcgctcaga tcgatgcgta cctgaccgat   780
gacctgtggc tgcgtaacgc ccgcaaagca aatgcagctg cgcagcgtct ggcccaaggt   840
ctggaaggcc tgggcggtgt tgaagtcctg ggcggtaccg aagcaaacat tctgttctgt   900
cgcctggatt ctgccatgat cgacgcactg ctgaaagctg gctttggttt cgggacgaag   960
cgttggggtc cgaacgtggt tcgctttgtt accagcttcg ctaccacggc ggaagatgtg  1020
gaccacctgc tgaatcaggt tcgcctggcc gcagaccgta cgcaagaacg c           1071
```

<210> SEQ ID NO 194
<211> LENGTH: 357
<212> TYPE: PRT
<213> ORGANISM: Artificial sequence
<220> FEATURE:
<223> OTHER INFORMATION: Engineered sequence

<400> SEQUENCE: 194

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Phe Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175
```

```
Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Thr Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Gly Thr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 195
<211> LENGTH: 1095
<212> TYPE: DNA
<213> ORGANISM: Artificial sequence
<220> FEATURE:
<223> OTHER INFORMATION: Engineered sequence

<400> SEQUENCE: 195
atgaatggtg aaaccagtcg tccgccggca ctgggtttta gcagcgaaaa cattgcaggc    60
gcaagtccgg aagttgcgca agcactggtt aaacatagct ctggtcaagc agatccgcat   120
agcagcggtc aagctggtcc gtatggtatg gatgaaatta ccgcgcaggt taaacgtaaa   180
ttctgcgaga tcttcgagcg cgacgttgaa gtttttctgg ttccgaccgg taccgctgct   240
aacgcactgt gtctgtctgc aatgacccct ccgtggggta atatttattg ccaccatgca   300
agccatatta taacgacga gtgcggcgca ccggaatttt tcagcaacgg cgccaaactg   360
atgaccgttg acggtccggc agcaaaactg gatattgtac gtctgcgcga acgtaccagc   420
gaaaaagttg cgacgttca taccacccaa ccggcttgcg ttagtattac ccaggcaacc   480
gaagttggta gcatctatac cctggacgaa atcgaagcga ttgcgacgt ctgcaaaagt   540 agtagtctgg gcctgcatat ggacggtagt cgttttgcga acgcactggt tagtctgggt   600
tgttctccgg cagaaatgac ctggaaagca ggtgttgacg cactgagttt tggcgcaacc   660
aaaaacggcg ttctggctgc agaagcaatt gttctgttta caccagcct ggccaccgaa   720 atgagctatc gtcgtaaacg cgcaggtcat ctgattagca acatcgtttt cctgagcgca   780
cagattgacg catatctgac cgacgatctg tggctgcgta acgcacgtaa agcaaacgca   840
gcagcacaac gtctggcaca aggtctggaa ggtctgggcg gcgttgaagt tctgggcggt   900
accgaagcaa acattctgtt ctgccgtatg gactctccga tgattgacgc actgctgaaa   960
```

```
gcgggcttta aatttggcta tgaacgctgg ggtccgaacg ttgttcgttt tgtcaccagc    1020
tttgcaacca ccgcagaaga cgttgatcat ctgctgaacc aagttcgtct ggcagcagat    1080
cgtacccaag aacgt                                                     1095
```

<210> SEQ ID NO 196
<211> LENGTH: 365
<212> TYPE: PRT
<213> ORGANISM: Artificial sequence
<220> FEATURE:
<223> OTHER INFORMATION: Engineered sequence

<400> SEQUENCE: 196

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Asp Pro His Ser Ser Gly Gln Ala Gly Pro Tyr
        35                  40                  45

Gly Met Asp Glu Ile Thr Ala Gln Val Lys Arg Lys Phe Cys Glu Ile
    50                  55                  60

Phe Glu Arg Asp Val Glu Val Phe Leu Val Pro Thr Gly Thr Ala Ala
65                  70                  75                  80

Asn Ala Leu Cys Leu Ser Ala Met Thr Pro Pro Trp Gly Asn Ile Tyr
                85                  90                  95

Cys His His Ala Ser His Ile Asn Asn Asp Glu Cys Gly Ala Pro Glu
            100                 105                 110

Phe Phe Ser Asn Gly Ala Lys Leu Met Thr Val Asp Gly Pro Ala Ala
        115                 120                 125

Lys Leu Asp Ile Val Arg Leu Arg Glu Arg Thr Ser Glu Lys Val Gly
    130                 135                 140

Asp Val His Thr Thr Gln Pro Ala Cys Val Ser Ile Thr Gln Ala Thr
145                 150                 155                 160

Glu Val Gly Ser Ile Tyr Thr Leu Asp Glu Ile Glu Ala Ile Gly Asp
                165                 170                 175

Val Cys Lys Ser Ser Ser Leu Gly Leu His Met Asp Gly Ser Arg Phe
            180                 185                 190

Ala Asn Ala Leu Val Ser Leu Gly Cys Ser Pro Ala Glu Met Thr Trp
        195                 200                 205

Lys Ala Gly Val Asp Ala Leu Ser Phe Gly Ala Thr Lys Asn Gly Val
    210                 215                 220

Leu Ala Ala Glu Ala Ile Val Leu Phe Asn Thr Ser Leu Ala Thr Glu
225                 230                 235                 240

Met Ser Tyr Arg Arg Lys Arg Ala Gly His Leu Ile Ser Lys His Arg
                245                 250                 255

Phe Leu Ser Ala Gln Ile Asp Ala Tyr Leu Thr Asp Asp Leu Trp Leu
            260                 265                 270

Arg Asn Ala Arg Lys Ala Asn Ala Ala Gln Arg Leu Ala Gln Gly
        275                 280                 285

Leu Glu Gly Leu Gly Gly Val Glu Val Leu Gly Thr Glu Ala Asn
    290                 295                 300

Ile Leu Phe Cys Arg Met Asp Ser Pro Met Ile Asp Ala Leu Leu Lys
305                 310                 315                 320

Ala Gly Phe Lys Phe Gly Tyr Glu Arg Trp Gly Pro Asn Val Val Arg
                325                 330                 335
```

Phe Val Thr Ser Phe Ala Thr Thr Ala Glu Asp Val Asp His Leu Leu
                340                 345                 350

Asn Gln Val Arg Leu Ala Ala Asp Arg Thr Gln Glu Arg
        355                 360                 365

<210> SEQ ID NO 197
<211> LENGTH: 1101
<212> TYPE: DNA
<213> ORGANISM: Artificial sequence
<220> FEATURE:
<223> OTHER INFORMATION: Engineered sequence

<400> SEQUENCE: 197

```
atgaatggtg aaaccagtcg tccgccggca ctgggtttta gcagcgaaaa cattgcaggc    60
gcaagtccgg aagttgcgca agcactggtt aaacatagct ctggtcaagc agatccgtat   120
ggtcatagca gcggtcaagc tggtccgtat ggtatggatg aaattaccgc gcaggttaaa   180
cgtaaattct gcgagatctt cgagcgcgac gttgaagttt ttctggttcc gaccggtacc   240
gctgctaacg cactgtgtct gtctgcaatg accccgccgt ggggtaatat ttattgccac   300
catgcaagcc atattaataa cgacgagtgc ggcgcaccgg aattttttcag caacggcgcc   360 aaactgatga ccgttgacgg tccggcagca aaactggata ttgtacgtct gcgcgaacgt   420
accagcgaaa agttggcga cgttcatacc acccaaccgg cttgcgttag tattacccag   480
gcaaccgaag ttggtagcat ctatacctg acgaaatcg aagcgattgg cgacgtctgc   540
aaaagtagta gtctgggcct gcatatggac ggtagtcgtt ttgcgaacgc actggttagt   600
ctgggttgtt ctccggcaga aatgacctgg aaagcaggtg ttgacgcact gagttttggc   660
gcaaccaaaa acggcgttct ggctgcagaa gcaattgttc tgtttaacac cagcctggcc   720
accgaaatga gctatcgtcg taaacgcgca ggtcatctga ttagcaaaca tcgtttcctg   780
agcgcacaga ttgacgcata tctgaccgac gatctgtggc tgcgtaacgc acgtaaagca   840
aacgcagcag cacaacgtct ggcacaaggt ctggaaggtc tgggcggcgt tgaagttctg   900
ggcggtaccg aagcaaacat tctgttctgc cgtatggact ctccgatgat gacgcactg    960 ctgaaagcgg ctttaaaatt tggctatgaa cgctggggtc cgaacgttgt tcgttttgtc  1020
accagctttg caaccaccgc agaagacgtt gatcatctgc tgaaccaagt tcgtctggca  1080
gcagatcgta cccaagaacg t                                            1101
```

<210> SEQ ID NO 198
<211> LENGTH: 367
<212> TYPE: PRT
<213> ORGANISM: Artificial sequence
<220> FEATURE:
<223> OTHER INFORMATION: Engineered sequence

<400> SEQUENCE: 198

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Asp Pro Tyr Gly His Ser Ser Gly Gln Ala Gly
        35                  40                  45

Pro Tyr Gly Met Asp Glu Ile Thr Ala Gln Val Lys Arg Lys Phe Cys
    50                  55                  60

Glu Ile Phe Glu Arg Asp Val Glu Val Phe Leu Val Pro Thr Gly Thr
65                  70                  75                  80

Ala Ala Asn Ala Leu Cys Leu Ser Ala Met Thr Pro Pro Trp Gly Asn
                85                  90                  95
Ile Tyr Cys His His Ala Ser His Ile Asn Asn Asp Glu Cys Gly Ala
            100                 105                 110
Pro Glu Phe Phe Ser Asn Gly Ala Lys Leu Met Thr Val Asp Gly Pro
        115                 120                 125
Ala Ala Lys Leu Asp Ile Val Arg Leu Arg Glu Arg Thr Ser Glu Lys
    130                 135                 140
Val Gly Asp Val His Thr Thr Gln Pro Ala Cys Val Ser Ile Thr Gln
145                 150                 155                 160
Ala Thr Glu Val Gly Ser Ile Tyr Thr Leu Asp Glu Ile Glu Ala Ile
                165                 170                 175
Gly Asp Val Cys Lys Ser Ser Ser Leu Gly Leu His Met Asp Gly Ser
            180                 185                 190
Arg Phe Ala Asn Ala Leu Val Ser Leu Gly Cys Ser Pro Ala Glu Met
        195                 200                 205
Thr Trp Lys Ala Gly Val Asp Ala Leu Ser Phe Gly Ala Thr Lys Asn
    210                 215                 220
Gly Val Leu Ala Ala Glu Ala Ile Val Leu Phe Asn Thr Ser Leu Ala
225                 230                 235                 240
Thr Glu Met Ser Tyr Arg Arg Lys Arg Ala Gly His Leu Ile Ser Lys
                245                 250                 255
His Arg Phe Leu Ser Ala Gln Ile Asp Ala Tyr Leu Thr Asp Asp Leu
            260                 265                 270
Trp Leu Arg Asn Ala Arg Lys Ala Asn Ala Ala Gln Arg Leu Ala
        275                 280                 285
Gln Gly Leu Glu Gly Leu Gly Gly Val Glu Val Leu Gly Gly Thr Glu
    290                 295                 300
Ala Asn Ile Leu Phe Cys Arg Met Asp Ser Pro Met Ile Asp Ala Leu
305                 310                 315                 320
Leu Lys Ala Gly Phe Lys Phe Gly Tyr Glu Arg Trp Gly Pro Asn Val
                325                 330                 335
Val Arg Phe Val Thr Ser Phe Ala Thr Thr Ala Glu Asp Val Asp His
            340                 345                 350
Leu Leu Asn Gln Val Arg Leu Ala Ala Asp Arg Thr Gln Glu Arg
        355                 360                 365

<210> SEQ ID NO 199
<211> LENGTH: 1107
<212> TYPE: DNA
<213> ORGANISM: Artificial sequence
<220> FEATURE:
<223> OTHER INFORMATION: Engineered sequence

<400> SEQUENCE: 199
atgaatggtg aaaccagtcg tccgccggca ctgggtttta gcagcgaaaa cattgcaggc    60
gcaagtccgg aagttgcgca agcactggtt aaacatagct ctggtcaagc agatccgtat   120
ggtaccgacc atagcagcgg tcaagctggt ccgtatggta tggatgaaat accgcgcag    180 gttaaacgta aattctgcga gatcttcgag cgcgacgttg aagttttctct ggttccgacc   240 ggtaccgctg ctaacgcact gtgtctgtct gcaatgaccc cgccgtgggg taatatttat   300
tgccaccatg caagccatat taataacgac gagtgcggcg caccggaatt tttcagcaac   360
ggcgccaaac tgatgaccgt tgacggtccg gcagcaaaac tggatattgt acgtctgcgc   420
gaacgtacca gcgaaaaagt tggcgacgtt cataccaccc aaccggcttg cgttagtatt   480

-continued

```
acccaggcaa ccgaagttgg tagcatctat accctggacg aaatcgaagc gattggcgac    540
gtctgcaaaa gtagtagtct gggcctgcat atggacggta gtcgttttgc gaacgcactg    600
gttagtctgg gttgttctcc ggcagaaatg acctggaaag caggtgttga cgcactgagt    660
tttggcgcaa ccaaaaacgg cgttctggct gcagaagcaa ttgttctgtt taacaccagc    720
ctggccaccg aaatgagcta tcgtcgtaaa cgcgcaggtc atctgattag caaacatcgt    780
ttcctgagcg cacagattga cgcatatctg accgacgatc tgtggctgcg taacgcacgt    840
aaagcaaacg cagcagcaca acgtctggca caaggtctgg aaggtctggg cggcgttgaa    900
gttctgggcg gtaccgaagc aaacattctg ttctgccgta tggactctcc gatgattgac    960
gcactgctga aagcgggctt taaatttggc tatgaacgct ggggtccgaa cgttgttcgt   1020
tttgtcacca gctttgcaac caccgcagaa gacgttgatc atctgctgaa ccaagttcgt   1080
ctggcagcag atcgtaccca agaacgt                                       1107
```

<210> SEQ ID NO 200
<211> LENGTH: 369
<212> TYPE: PRT
<213> ORGANISM: Artificial sequence
<220> FEATURE:
<223> OTHER INFORMATION: Engineered sequence

<400> SEQUENCE: 200

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
                20                  25                  30

Ser Ser Gly Gln Ala Asp Pro Tyr Gly Thr Asp His Ser Ser Gly Gln
        35                  40                  45

Ala Gly Pro Tyr Gly Met Asp Glu Ile Thr Ala Gln Val Lys Arg Lys
    50                  55                  60

Phe Cys Glu Ile Phe Glu Arg Asp Val Glu Val Phe Leu Val Pro Thr
65                  70                  75                  80

Gly Thr Ala Ala Asn Ala Leu Cys Leu Ser Ala Met Thr Pro Pro Trp
                85                  90                  95

Gly Asn Ile Tyr Cys His His Ala Ser His Ile Asn Asn Asp Glu Cys
            100                 105                 110

Gly Ala Pro Glu Phe Phe Ser Asn Gly Ala Lys Leu Met Thr Val Asp
        115                 120                 125

Gly Pro Ala Ala Lys Leu Asp Ile Val Arg Leu Arg Glu Arg Thr Ser
    130                 135                 140

Glu Lys Val Gly Asp Val His Thr Thr Gln Pro Ala Cys Val Ser Ile
145                 150                 155                 160

Thr Gln Ala Thr Glu Val Gly Ser Ile Tyr Thr Leu Asp Glu Ile Glu
                165                 170                 175

Ala Ile Gly Asp Val Cys Lys Ser Ser Leu Gly Leu His Met Asp
            180                 185                 190

Gly Ser Arg Phe Ala Asn Ala Leu Val Ser Leu Gly Cys Ser Pro Ala
        195                 200                 205

Glu Met Thr Trp Lys Ala Gly Val Asp Ala Leu Ser Phe Gly Ala Thr
    210                 215                 220

Lys Asn Gly Val Leu Ala Ala Glu Ala Ile Val Leu Phe Asn Thr Ser
225                 230                 235                 240

Leu Ala Thr Glu Met Ser Tyr Arg Arg Lys Arg Ala Gly His Leu Ile
```

```
                    245                 250                 255
Ser Lys His Arg Phe Leu Ser Ala Gln Ile Asp Ala Tyr Leu Thr Asp
        260                 265                 270

Asp Leu Trp Leu Arg Asn Ala Arg Lys Ala Asn Ala Ala Gln Arg
    275                 280                 285

Leu Ala Gln Gly Leu Glu Gly Leu Gly Gly Val Glu Val Leu Gly Gly
        290                 295                 300

Thr Glu Ala Asn Ile Leu Phe Cys Arg Met Asp Ser Pro Met Ile Asp
305                 310                 315                 320

Ala Leu Leu Lys Ala Gly Phe Lys Phe Gly Tyr Glu Arg Trp Gly Pro
                325                 330                 335

Asn Val Val Arg Phe Val Thr Ser Phe Ala Thr Thr Ala Glu Asp Val
                340                 345                 350

Asp His Leu Leu Asn Gln Val Arg Leu Ala Ala Asp Arg Thr Gln Glu
        355                 360                 365

Arg

<210> SEQ ID NO 201
<211> LENGTH: 1083
<212> TYPE: DNA
<213> ORGANISM: Artificial sequence
<220> FEATURE:
<223> OTHER INFORMATION: Engineered sequence

<400> SEQUENCE: 201
atgagtcgtc cgccggcact gggttttagc agcgaaaaca ttgcaggcgc aagtccggaa      60
gttgcgcaag cactggttaa acatagctct ggtcaagcag atccgcatag cagcggtcaa     120
gctggtccgt atggtatgga tgaaattacc gcgcaggtta acgtaaaatt ctgcgagatc     180
ttcgagcgcg acgttgaagt ttttctggtt ccgaccggta ccgctgctaa cgcactgtgt     240
ctgtctgcaa tgaccccgcc gtggggtaat atttattgcc accatgcaag ccatattaat     300
aacgacgagt gcggcgcacc ggaattttc agcaacggcg ccaaactgat gaccgttgac     360
ggtccggcag caaaactgga tattgtacgt ctgcgcgaac gtaccagcga aaaagttggc     420
gacgttcata ccacccaacc ggcttgcgtt agtattaccc aggcaaccga agttggtagc     480
atctatatcc cggacgaaat cgaagcgatt ggcgacgtct gcaaaagtag tagtctgggc     540
ctgcatatgg acggtagtcg ttttgcgaac gcactggtta gtctggggttg ttctccggca     600 gaaatgacct ggaaagcagg tgttgacgca ctgagttttg cgcaaccaa aaacggcgtt     660 ctggctgcag aagcaattgt tctgtttaac accagcctgg ccaccgaaat gagctatcgt     720
cgtaaacgcg caggtcatct gattagcaaa catcgtttcc tgagcgcaca gattgacgca     780
tatctgaccg acgatctgtg gctgcgtaac gcacgtaaag caaacgcagc agcacaacgt     840
ctggcacaag gtctggaagg tctgggcggc gttgaagttc tgggcggtac cgaagcaaac     900
attctgttct gccgtatgga ctctccgatg attgacgcac tgctgaaagc gggctttaaa     960
tttggctatg aacgctgggg tccgaacgtt gttcgttttg tcaccagctt tgcaaccacc    1020
gcagaagacg ttgatcatct gctgaaccaa gttcgtctgg cagcagatcg tacccaagaa    1080
cgt                                                                  1083

<210> SEQ ID NO 202
<211> LENGTH: 361
<212> TYPE: PRT
<213> ORGANISM: Artificial sequence
<220> FEATURE:
```

<223> OTHER INFORMATION: Engineered sequence

<400> SEQUENCE: 202

| Met | Ser | Arg | Pro | Pro | Ala | Leu | Gly | Phe | Ser | Ser | Glu | Asn | Ile | Ala | Gly |
|---|---|---|---|---|---|---|---|---|---|---|---|---|---|---|---|
| 1 | | | | 5 | | | | | 10 | | | | | 15 | |

Ala Ser Pro Glu Val Ala Gln Ala Leu Val Lys His Ser Ser Gly Gln
        20                  25                  30

Ala Asp Pro His Ser Ser Gly Gln Ala Gly Pro Tyr Gly Met Asp Glu
            35                  40                  45

Ile Thr Ala Gln Val Lys Arg Lys Phe Cys Glu Ile Phe Glu Arg Asp
50                  55                  60

Val Glu Val Phe Leu Val Pro Thr Gly Thr Ala Ala Asn Ala Leu Cys
65                  70                  75                  80

Leu Ser Ala Met Thr Pro Pro Trp Gly Asn Ile Tyr Cys His His Ala
                85                  90                  95

Ser His Ile Asn Asn Asp Glu Cys Gly Ala Pro Glu Phe Phe Ser Asn
                    100                 105                 110

Gly Ala Lys Leu Met Thr Val Asp Gly Pro Ala Ala Lys Leu Asp Ile
                115                 120                 125

Val Arg Leu Arg Glu Arg Thr Ser Glu Lys Val Gly Asp Val His Thr
130                 135                 140

Thr Gln Pro Ala Cys Val Ser Ile Thr Gln Ala Thr Glu Val Gly Ser
145                 150                 155                 160

Ile Tyr Thr Leu Asp Glu Ile Glu Ala Ile Gly Asp Val Cys Lys Ser
                165                 170                 175

Ser Ser Leu Gly Leu His Met Asp Gly Ser Arg Phe Ala Asn Ala Leu
                180                 185                 190

Val Ser Leu Gly Cys Ser Pro Ala Glu Met Thr Trp Lys Ala Gly Val
                195                 200                 205

Asp Ala Leu Ser Phe Gly Ala Thr Lys Asn Gly Val Leu Ala Ala Glu
                210                 215                 220

Ala Ile Val Leu Phe Asn Thr Ser Leu Ala Thr Glu Met Ser Tyr Arg
225                 230                 235                 240

Arg Lys Arg Ala Gly His Leu Ile Ser Lys His Arg Phe Leu Ser Ala
                245                 250                 255

Gln Ile Asp Ala Tyr Leu Thr Asp Asp Leu Trp Leu Arg Asn Ala Arg
                260                 265                 270

Lys Ala Asn Ala Ala Ala Gln Arg Leu Ala Gln Gly Leu Glu Gly Leu
                275                 280                 285

Gly Gly Val Glu Val Leu Gly Gly Thr Glu Ala Asn Ile Leu Phe Cys
                290                 295                 300

Arg Met Asp Ser Pro Met Ile Asp Ala Leu Leu Lys Ala Gly Phe Lys
305                 310                 315                 320

Phe Gly Tyr Glu Arg Trp Gly Pro Asn Val Val Arg Phe Val Thr Ser
                325                 330                 335

Phe Ala Thr Thr Ala Glu Asp Val Asp His Leu Leu Asn Gln Val Arg
                340                 345                 350

Leu Ala Ala Asp Arg Thr Gln Glu Arg
                355                 360

<210> SEQ ID NO 203
<211> LENGTH: 1080
<212> TYPE: DNA
<213> ORGANISM: Artificial sequence
<220> FEATURE:

<223> OTHER INFORMATION: Engineered sequence

<400> SEQUENCE: 203

```
atgcgtccgc cggcactggg ttttagcagc gaaaacattg caggcgcaag tccggaagtt      60
gcgcaagcac tggttaaaca tagctctggt caagcagatc cgcatagcag cggtcaagct     120
ggtccgtatg gtatggatga attaccgcg caggttaaac gtaaattctg cgagatcttc     180
gagcgcgacg ttgaagtttt tctggttccg accggtaccg ctgctaacgc actgtgtctg     240
tctgcaatga ccccgccgtg gggtaatatt tattgccacc atgcaagcca tattaataac     300
gacgagtgcg gcgcaccgga attttcagc aacggcgcca aactgatgac cgttgacggt     360
ccggcagcaa aactggatat tgtacgtctg cgcgaacgta ccagcgaaaa agttggcgac     420
gttcatacca cccaaccggc ttgcgttagt attacccagg caaccgaagt tggtagcatc     480
tatccctgg acgaaatcga agcgattggc gacgtctgca aaagtagtag tctgggcctg     540
catatggacg tagtcgttt tgcgaacgca ctggttagtc tgggttgttc tccggcagaa     600
atgacctgga aagcaggtgt tgacgcactg agttttggcg caaccaaaaa cggcgttctg     660
gctgcagaag caattgttct gtttaacacc agcctggcca ccgaaatgag ctatcgtcgt     720
aaacgcgcag gtcatctgat tagcaaacat cgtttcctga cgcacagat tgacgcatat     780
ctgaccgacg atctgtggct gcgtaacgca cgtaaagcaa acgcagcagc acaacgtctg     840
gcacaaggtc tggaaggtct gggcggcgtt gaagttctgg cggtaccga agcaaacatt     900
ctgttctgcc gtatggactc tccgatgatt gacgcactgc tgaaagcggg ctttaaattt     960
ggctatgaac gctgggtcc gaacgttgtt cgtttttgtca ccagctttgc aaccaccgca    1020
gaagacgttg atcatctgct gaaccaagtt cgtctggcag cagatcgtac ccaagaacgt    1080
```

<210> SEQ ID NO 204
<211> LENGTH: 360
<212> TYPE: PRT
<213> ORGANISM: Artificial sequence
<220> FEATURE:
<223> OTHER INFORMATION: Engineered sequence

<400> SEQUENCE: 204

```
Met Arg Pro Pro Ala Leu Gly Phe Ser Ser Glu Asn Ile Ala Gly Ala
1               5                   10                  15

Ser Pro Glu Val Ala Gln Ala Leu Val Lys His Ser Ser Gly Gln Ala
            20                  25                  30

Asp Pro His Ser Ser Gly Gln Ala Gly Pro Tyr Gly Met Asp Glu Ile
        35                  40                  45

Thr Ala Gln Val Lys Arg Lys Phe Cys Glu Ile Phe Glu Arg Asp Val
    50                  55                  60

Glu Val Phe Leu Val Pro Thr Gly Thr Ala Ala Asn Ala Leu Cys Leu
65                  70                  75                  80

Ser Ala Met Thr Pro Pro Trp Gly Asn Ile Tyr Cys His His Ala Ser
                85                  90                  95

His Ile Asn Asn Asp Glu Cys Gly Ala Pro Glu Phe Phe Ser Asn Gly
            100                 105                 110

Ala Lys Leu Met Thr Val Asp Gly Pro Ala Ala Lys Leu Asp Ile Val
        115                 120                 125

Arg Leu Arg Glu Arg Thr Ser Glu Lys Val Gly Asp Val His Thr Thr
    130                 135                 140

Gln Pro Ala Cys Val Ser Ile Thr Gln Ala Thr Glu Val Gly Ser Ile
145                 150                 155                 160
```

Tyr Thr Leu Asp Glu Ile Glu Ala Ile Gly Asp Val Cys Lys Ser Ser
            165                 170                 175

Ser Leu Gly Leu His Met Asp Gly Ser Arg Phe Ala Asn Ala Leu Val
        180                 185                 190

Ser Leu Gly Cys Ser Pro Ala Glu Met Thr Trp Lys Ala Gly Val Asp
        195                 200                 205

Ala Leu Ser Phe Gly Ala Thr Lys Asn Gly Val Leu Ala Ala Glu Ala
        210                 215                 220

Ile Val Leu Phe Asn Thr Ser Leu Ala Thr Glu Met Ser Tyr Arg Arg
225                 230                 235                 240

Lys Arg Ala Gly His Leu Ile Ser Lys His Arg Phe Leu Ser Ala Gln
                245                 250                 255

Ile Asp Ala Tyr Leu Thr Asp Asp Leu Trp Leu Arg Asn Ala Arg Lys
            260                 265                 270

Ala Asn Ala Ala Ala Gln Arg Leu Ala Gln Gly Leu Glu Gly Leu Gly
        275                 280                 285

Gly Val Glu Val Leu Gly Gly Thr Glu Ala Asn Ile Leu Phe Cys Arg
        290                 295                 300

Met Asp Ser Pro Met Ile Asp Ala Leu Leu Lys Ala Gly Phe Lys Phe
305                 310                 315                 320

Gly Tyr Glu Arg Trp Gly Pro Asn Val Val Arg Phe Val Thr Ser Phe
                325                 330                 335

Ala Thr Thr Ala Glu Asp Val Asp His Leu Leu Asn Gln Val Arg Leu
            340                 345                 350

Ala Ala Asp Arg Thr Gln Glu Arg
        355                 360

<210> SEQ ID NO 205
<211> LENGTH: 1074
<212> TYPE: DNA
<213> ORGANISM: Artificial sequence
<220> FEATURE:
<223> OTHER INFORMATION: Engineered sequence

<400> SEQUENCE: 205
atgccggcac tgggttttag cagcgaaaac attgcaggcg caagtccgga agttgcgcaa      60
gcactggtta acatagctc tggtcaagca gatccgcata gcagcggtca agctggtccg     120
tatggtatgg atgaaattac cgcgcaggtt aaacgtaaat ctgcgagat cttcgagcgc     180 gacgttgaag tttttctggt tccgaccggt accgctgcta acgcactgtg tctgtctgca     240
atgaccccgc cgtggggtaa tatttattgc caccatgcaa gccatattaa taacgacgag     300
tgcggcgcac cggaattttt cagcaacggc gccaaactga tgaccgttga cggtccggca     360
gcaaaactgg atattgtacg tctgcgcgaa cgtaccagcg aaaaagttgg cgacgttcat     420
accacccaac cggcttgcgt tagtattacc caggcaaccg aagttggtag catctatacc     480
ctggacgaaa tcgaagcgat ggcgacgtc tgcaaaagta gtagtctggg cctgcatatg     540
gacggtagtc gttttgcgaa cgcactggtt agtctgggtt gttctccggc agaaatgacc     600
tggaaagcag gtgttgacgc actgagtttt ggcgcaacca aaaacggcgt tctggctgca     660
gaagcaattg ttctgtttaa caccagcctg gccaccgaaa tgagctatcg tcgtaaacgc     720
gcaggtcatc tgattagcaa acatcgtttc ctgagcgcac agattgacgc atatctgacc     780
gacgatctgt ggctgcgtaa cgcacgtaaa gcaaacgcag cagcacaacg tctggcacaa     840
ggtctggaag gtctgggcgg cgttgaagtt ctgggcggta ccgaagcaaa cattctgttc     900

```
tgccgtatgg actctccgat gattgacgca ctgctgaaag cgggctttaa atttggctat        960
gaacgctggg gtccgaacgt tgttcgtttt gtcaccagct ttgcaaccac cgcagaagac       1020
gttgatcatc tgctgaacca agttcgtctg gcagcagatc gtacccaaga acgt            1074
```

<210> SEQ ID NO 206
<211> LENGTH: 358
<212> TYPE: PRT
<213> ORGANISM: Artificial sequence
<220> FEATURE:
<223> OTHER INFORMATION: Engineered sequence

<400> SEQUENCE: 206

```
Met Pro Ala Leu Gly Phe Ser Ser Glu Asn Ile Ala Gly Ala Ser Pro
1               5                   10                  15

Glu Val Ala Gln Ala Leu Val Lys His Ser Ser Gly Gln Ala Asp Pro
            20                  25                  30

His Ser Ser Gly Gln Ala Gly Pro Tyr Gly Met Asp Glu Ile Thr Ala
        35                  40                  45

Gln Val Lys Arg Lys Phe Cys Glu Ile Phe Glu Arg Asp Val Glu Val
    50                  55                  60

Phe Leu Val Pro Thr Gly Thr Ala Ala Asn Ala Leu Cys Leu Ser Ala
65                  70                  75                  80

Met Thr Pro Pro Trp Gly Asn Ile Tyr Cys His His Ala Ser His Ile
                85                  90                  95

Asn Asn Asp Glu Cys Gly Ala Pro Glu Phe Phe Ser Asn Gly Ala Lys
            100                 105                 110

Leu Met Thr Val Asp Gly Pro Ala Ala Lys Leu Asp Ile Val Arg Leu
        115                 120                 125

Arg Glu Arg Thr Ser Glu Lys Val Gly Asp Val His Thr Thr Gln Pro
    130                 135                 140

Ala Cys Val Ser Ile Thr Gln Ala Thr Glu Val Gly Ser Ile Tyr Thr
145                 150                 155                 160

Leu Asp Glu Ile Glu Ala Ile Gly Asp Val Cys Lys Ser Ser Ser Leu
                165                 170                 175

Gly Leu His Met Asp Gly Ser Arg Phe Ala Asn Ala Leu Val Ser Leu
            180                 185                 190

Gly Cys Ser Pro Ala Glu Met Thr Trp Lys Ala Gly Val Asp Ala Leu
        195                 200                 205

Ser Phe Gly Ala Thr Lys Asn Gly Val Leu Ala Ala Glu Ala Ile Val
    210                 215                 220

Leu Phe Asn Thr Ser Leu Ala Thr Glu Met Ser Tyr Arg Arg Lys Arg
225                 230                 235                 240

Ala Gly His Leu Ile Ser Lys His Arg Phe Leu Ser Ala Gln Ile Asp
                245                 250                 255

Ala Tyr Leu Thr Asp Asp Leu Trp Leu Arg Asn Ala Arg Lys Ala Asn
            260                 265                 270

Ala Ala Ala Gln Arg Leu Ala Gln Gly Leu Glu Gly Leu Gly Gly Val
        275                 280                 285

Glu Val Leu Gly Gly Thr Glu Ala Asn Ile Leu Phe Cys Arg Met Asp
    290                 295                 300

Ser Pro Met Ile Asp Ala Leu Leu Lys Ala Gly Phe Lys Phe Gly Tyr
305                 310                 315                 320

Glu Arg Trp Gly Pro Asn Val Val Arg Phe Val Thr Ser Phe Ala Thr
                325                 330                 335
```

```
Thr Ala Glu Asp Val Asp His Leu Leu Asn Gln Val Arg Leu Ala Ala
        340                 345                 350
Asp Arg Thr Gln Glu Arg
        355
```

<210> SEQ ID NO 207
<211> LENGTH: 1077
<212> TYPE: DNA
<213> ORGANISM: Artificial sequence
<220> FEATURE:
<223> OTHER INFORMATION: Engineered sequence

<400> SEQUENCE: 207

```
atgaatggtg aaaccagtcg tccgccggca ctgggtttta gcagcgaaaa cattgcaggc      60
gcaagtccgg aagttgcgca agcactggtt aaacatagca gcggtcaagc tggtccgtat     120
ggtatggatg aaattaccgc gcaggttaaa catagccgta aattctgcga gatcttcgag     180
cgcgacgttg aagttttctct ggttccgacc ggtaccgctg ctaacgcact gtgtctgtct     240
gcaatgaccc cgccgtgggg taatatttat tgccaccatg caagccatat aataacgac      300
gagtgcggcg caccggaatt tttcagcaac ggcgccaaac tgatgaccgt tgacggtccg     360
gcagcaaaac tggatattgt acgtctgcgc gaacgtacca gcgaaaaagt tggcgacgtt     420
cataccaccc aaccggcttg cgttagtatt acccaggcaa ccgaagttgg tagcatctat     480
accctggacg aaatcgaagc gattggcgac gtctgcaaaa gtagtagtct gggcctgcat     540
atggacggta gtcgttttgc gaacgcactg gttagtctgg ttgttctcc ggcagaaatg      600
acctggaaag caggtgttga cgcactgagt tttggcgcaa ccaaaaacgg cgttctggct     660
gcagaagcaa ttgttctgtt taacaccagc ctggccaccg aaatgagcta tcgtcgtaaa     720
cgcgcaggtc atctgattag caaacatcgt ttcctgagcg cacagattga cgcatatctg     780
accgacgatc tgtggctgcg taacgcacgt aaagcaaacg cagcagcaca acgtctggca     840
caaggtctgg aaggtctggg cggcgttgaa gttctgggcg gtaccgaagc aaacattctg     900
ttctgccgta tggactctcc gatgattgac gcactgctga agcgggcttt aaatttggc      960
tatgaacgct ggggtccgaa cgttgttcgt tttgtcacca gctttgcaac caccgcagaa    1020
gacgttgatc atctgctgaa ccaagttcgt ctggcagcag atcgtaccca agaacgt       1077
```

<210> SEQ ID NO 208
<211> LENGTH: 359
<212> TYPE: PRT
<213> ORGANISM: Artificial sequence
<220> FEATURE:
<223> OTHER INFORMATION: Engineered sequence

<400> SEQUENCE: 208

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys His Ser Arg Lys Phe Cys Glu Ile Phe Glu Arg Asp Val Glu
    50                  55                  60

Val Phe Leu Val Pro Thr Gly Thr Ala Ala Asn Ala Leu Cys Leu Ser
65                  70                  75                  80

Ala Met Thr Pro Pro Trp Gly Asn Ile Tyr Cys His His Ala Ser His
```

```
                85                  90                  95
Ile Asn Asn Asp Glu Cys Gly Ala Pro Glu Phe Phe Ser Asn Gly Ala
            100                 105                 110
Lys Leu Met Thr Val Asp Gly Pro Ala Ala Lys Leu Asp Ile Val Arg
        115                 120                 125
Leu Arg Glu Arg Thr Ser Glu Lys Val Gly Asp Val His Thr Thr Gln
    130                 135                 140
Pro Ala Cys Val Ser Ile Thr Gln Ala Thr Glu Val Gly Ser Ile Tyr
145                 150                 155                 160
Thr Leu Asp Glu Ile Glu Ala Ile Gly Asp Val Cys Lys Ser Ser Ser
                165                 170                 175
Leu Gly Leu His Met Asp Gly Ser Arg Phe Ala Asn Ala Leu Val Ser
            180                 185                 190
Leu Gly Cys Ser Pro Ala Glu Met Thr Trp Lys Ala Gly Val Asp Ala
        195                 200                 205
Leu Ser Phe Gly Ala Thr Lys Asn Gly Val Leu Ala Ala Glu Ala Ile
    210                 215                 220
Val Leu Phe Asn Thr Ser Leu Ala Thr Glu Met Ser Tyr Arg Arg Lys
225                 230                 235                 240
Arg Ala Gly His Leu Ile Ser Lys His Arg Phe Leu Ser Ala Gln Ile
                245                 250                 255
Asp Ala Tyr Leu Thr Asp Asp Leu Trp Leu Arg Asn Ala Arg Lys Ala
            260                 265                 270
Asn Ala Ala Ala Gln Arg Leu Ala Gln Gly Leu Glu Gly Leu Gly Gly
        275                 280                 285
Val Glu Val Leu Gly Gly Thr Glu Ala Asn Ile Leu Phe Cys Arg Met
    290                 295                 300
Asp Ser Pro Met Ile Asp Ala Leu Leu Lys Ala Gly Phe Lys Phe Gly
305                 310                 315                 320
Tyr Glu Arg Trp Gly Pro Asn Val Val Arg Phe Val Thr Ser Phe Ala
                325                 330                 335
Thr Thr Ala Glu Asp Val Asp His Leu Leu Asn Gln Val Arg Leu Ala
            340                 345                 350
Ala Asp Arg Thr Gln Glu Arg
        355

<210> SEQ ID NO 209
<211> LENGTH: 1077
<212> TYPE: DNA
<213> ORGANISM: Artificial sequence
<220> FEATURE:
<223> OTHER INFORMATION: Engineered sequence

<400> SEQUENCE: 209
atgaatggtg aaaccagtcg tccgccggca ctgggtttta gcagcgaaaa cattgcaggc      60
gcaagtccgg aagttgcgca agcactggtt aaacatagcc atagcagcgg tcaagctggt     120
ccgtatggta tggatgaaat taccgcgcag gttaaacgta aattctgcga gatcttcgag     180
cgcgacgttg aagtttttct ggttccgacc ggtaccgctg ctaacgcact gtgtctgtct     240
gcaatgaccc cgccgtgggg taatatttat tgccaccatg caagccatat taataacgac     300
gagtgcggcg caccggaatt tttcagcaac ggcgccaaac tgatgaccgt tgacggtccg     360
gcagcaaaac tggatattgt acgtctgcgc gaacgtacca gcgaaaaagt tggcgacgtt     420
cataccaccc aaccggcttg cgttagtatt acccaggcaa ccgaagttgg tagcatctat     480
```

```
accctggacg aaatcgaagc gattggcgac gtctgcaaaa gtagtagtct gggcctgcat    540
atggacggta gtcgttttgc gaacgcactg gttagtctgg gttgttctcc ggcagaaatg    600
acctggaaag caggtgttga cgcactgagt tttggcgcaa ccaaaaacgg cgttctggct    660
gcagaagcaa ttgttctgtt aacaccagc ctggccaccg aaatgagcta tcgtcgtaaa    720
cgcgcaggtc atctgattag caaacatcgt ttcctgagcg cacagattga cgcatatctg    780
accgacgatc tgtggctgcg taacgcacgt aaagcaaacg cagcagcaca acgtctggca    840
caaggtctgg aagtctggg cggcgttgaa gttctgggcg gtaccgaagc aaacattctg    900
ttctgccgta tggactctcc gatgattgac gcactgctga agcgggctt taaatttggc    960 tatgaacgct ggggtccgaa cgttgttcgt tttgtcacca gctttgcaac caccgcagaa   1020
gacgttgatc atctgctgaa ccaagttcgt ctggcagcag atcgtaccca agaacgt      1077
```

<210> SEQ ID NO 210
<211> LENGTH: 359
<212> TYPE: PRT
<213> ORGANISM: Artificial sequence
<220> FEATURE:
<223> OTHER INFORMATION: Engineered sequence

<400> SEQUENCE: 210

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser His Ser Ser Gly Gln Ala Gly Pro Tyr Gly Met Asp Glu Ile Thr
        35                  40                  45

Ala Gln Val Lys Arg Lys Phe Cys Glu Ile Phe Glu Arg Asp Val Glu
    50                  55                  60

Val Phe Leu Val Pro Thr Gly Thr Ala Ala Asn Ala Leu Cys Leu Ser
65                  70                  75                  80

Ala Met Thr Pro Pro Trp Gly Asn Ile Tyr Cys His His Ala Ser His
                85                  90                  95

Ile Asn Asn Asp Glu Cys Gly Ala Pro Glu Phe Phe Ser Asn Gly Ala
            100                 105                 110

Lys Leu Met Thr Val Asp Gly Pro Ala Ala Lys Leu Asp Ile Val Arg
        115                 120                 125

Leu Arg Glu Arg Thr Ser Glu Lys Val Gly Asp Val His Thr Thr Gln
    130                 135                 140

Pro Ala Cys Val Ser Ile Thr Gln Ala Thr Glu Val Gly Ser Ile Tyr
145                 150                 155                 160

Thr Leu Asp Glu Ile Glu Ala Ile Gly Asp Val Cys Lys Ser Ser Ser
                165                 170                 175

Leu Gly Leu His Met Asp Gly Ser Arg Phe Ala Asn Ala Leu Val Ser
            180                 185                 190

Leu Gly Cys Ser Pro Ala Glu Met Thr Trp Lys Ala Gly Val Asp Ala
        195                 200                 205

Leu Ser Phe Gly Ala Thr Lys Asn Gly Val Leu Ala Ala Glu Ala Ile
    210                 215                 220

Val Leu Phe Asn Thr Ser Leu Ala Thr Glu Met Ser Tyr Arg Arg Lys
225                 230                 235                 240

Arg Ala Gly His Leu Ile Ser Lys His Arg Phe Leu Ser Ala Gln Ile
                245                 250                 255

Asp Ala Tyr Leu Thr Asp Asp Leu Trp Leu Arg Asn Ala Arg Lys Ala
```

```
                    260                 265                 270
Asn Ala Ala Ala Gln Arg Leu Ala Gln Gly Leu Glu Gly Leu Gly Gly
            275                 280                 285

Val Glu Val Leu Gly Gly Thr Glu Ala Asn Ile Leu Phe Cys Arg Met
        290                 295                 300

Asp Ser Pro Met Ile Asp Ala Leu Leu Lys Ala Gly Phe Lys Phe Gly
305                 310                 315                 320

Tyr Glu Arg Trp Gly Pro Asn Val Val Arg Phe Val Thr Ser Phe Ala
                325                 330                 335

Thr Thr Ala Glu Asp Val Asp His Leu Leu Asn Gln Val Arg Leu Ala
            340                 345                 350

Ala Asp Arg Thr Gln Glu Arg
        355
```

<210> SEQ ID NO 211
<211> LENGTH: 1083
<212> TYPE: DNA
<213> ORGANISM: Artificial sequence
<220> FEATURE:
<223> OTHER INFORMATION: Engineered sequence

<400> SEQUENCE: 211

```
atgaatggtg aaaccagtcg tccgccggca ctgggttta gcagcgaaaa cattgcaggc      60
gcaagtccgg aagttgcgca agcactggtt aaacatagct ctggtcatag cagcggtcaa     120
gctggtccgt atggtatgga tgaaattacc gcgcaggtta acgtaaatt ctgcgagatc      180
ttcgagcgcg acgttgaagt ttttctggtt ccgaccggta ccgctgctaa cgcactgtgt     240
ctgtctgcaa tgaccccgcc gtggggtaat atttattgcc accatgcaag ccatattaat     300
aacgacgagt gcggcgcacc ggaatttttc agcaacggcg ccaaactgat gaccgttgac     360
ggtccggcag caaaactgga tattgtacgt ctgcgcgaac gtaccagcga aaagttggc      420
gacgttcata ccacccaacc ggcttgcgtt agtattaccc aggcaaccga agttggtagc     480
atctatacc tggacgaaat cgaagcgatt ggcgacgtct gcaaaagtag tagtctgggc      540
ctgcatatgg acggtagtcg ttttgcgaac gcactggtta gtctggggttg ttctccggca    600
gaaatgacct ggaaagcagg tgttgacgca ctgagttttg gcgcaaccaa aaacggcgtt     660
ctggctgcag aagcaattgt tctgtttaac accagcctgg ccaccgaaat gagctatcgt     720
cgtaaacgcg caggtcatct gattagcaaa catcgtttcc tgagcgcaca gattgacgca     780
tatctgaccg acgatctgtg gctgcgtaac gcacgtaaag caaacgcagc agcacaacgt     840
ctggcacaag gtctggaagg tctgggcggc gttgaagttc tgggcggtac cgaagcaaac     900
attctgttct gccgtatgga ctctccgatg attgacgcac tgctgaaagc gggctttaaa     960
tttggctatg aacgctgggg tccgaacgtt gttcgttttg tcaccagctt tgcaaccacc    1020
gcagaagacg ttgatcatct gctgaaccaa gttcgtctgg cagcagatcg tacccaagaa    1080
cgt                                                                  1083
```

<210> SEQ ID NO 212
<211> LENGTH: 361
<212> TYPE: PRT
<213> ORGANISM: Artificial sequence
<220> FEATURE:
<223> OTHER INFORMATION: Engineered sequence

<400> SEQUENCE: 212

Met Asn Gly Glu Thr Ser Arg Pro Pro Ala Leu Gly Phe Ser Ser Glu

```
            1               5                   10                  15
        Asn Ile Ala Gly Ala Ser Pro Glu Val Ala Gln Ala Leu Val Lys His
                        20                  25                  30

Ser Ser Gly His Ser Ser Gly Gln Ala Gly Pro Tyr Gly Met Asp Glu
                        35                  40                  45

Ile Thr Ala Gln Val Lys Arg Lys Phe Cys Glu Ile Phe Glu Arg Asp
                        50                  55                  60

Val Glu Val Phe Leu Val Pro Thr Gly Thr Ala Ala Asn Ala Leu Cys
        65                      70                  75                  80

Leu Ser Ala Met Thr Pro Pro Trp Gly Asn Ile Tyr Cys His His Ala
                        85                  90                  95

Ser His Ile Asn Asn Asp Glu Cys Gly Ala Pro Glu Phe Phe Ser Asn
                        100                 105                 110

Gly Ala Lys Leu Met Thr Val Asp Gly Pro Ala Ala Lys Leu Asp Ile
                        115                 120                 125

Val Arg Leu Arg Glu Arg Thr Ser Glu Lys Val Gly Asp Val His Thr
                        130                 135                 140

Thr Gln Pro Ala Cys Val Ser Ile Thr Gln Ala Thr Glu Val Gly Ser
        145                     150                 155                 160

Ile Tyr Thr Leu Asp Glu Ile Glu Ala Ile Gly Asp Val Cys Lys Ser
                        165                 170                 175

Ser Ser Leu Gly Leu His Met Asp Gly Ser Arg Phe Ala Asn Ala Leu
                        180                 185                 190

Val Ser Leu Gly Cys Ser Pro Ala Glu Met Thr Trp Lys Ala Gly Val
                        195                 200                 205

Asp Ala Leu Ser Phe Gly Ala Thr Lys Asn Gly Val Leu Ala Ala Glu
                        210                 215                 220

Ala Ile Val Leu Phe Asn Thr Ser Leu Ala Thr Glu Met Ser Tyr Arg
        225                     230                 235                 240

Arg Lys Arg Ala Gly His Leu Ile Ser Lys His Arg Phe Leu Ser Ala
                        245                 250                 255

Gln Ile Asp Ala Tyr Leu Thr Asp Asp Leu Trp Leu Arg Asn Ala Arg
                        260                 265                 270

Lys Ala Asn Ala Ala Ala Gln Arg Leu Ala Gln Gly Leu Glu Gly Leu
                        275                 280                 285

Gly Gly Val Glu Val Leu Gly Gly Thr Glu Ala Asn Ile Leu Phe Cys
                        290                 295                 300

Arg Met Asp Ser Pro Met Ile Asp Ala Leu Leu Lys Ala Gly Phe Lys
        305                     310                 315                 320

Phe Gly Tyr Glu Arg Trp Gly Pro Asn Val Val Arg Phe Val Thr Ser
                        325                 330                 335

Phe Ala Thr Thr Ala Glu Asp Val Asp His Leu Leu Asn Gln Val Arg
                        340                 345                 350

Leu Ala Ala Asp Arg Thr Gln Glu Arg
                        355                 360

<210> SEQ ID NO 213
<211> LENGTH: 1026
<212> TYPE: DNA
<213> ORGANISM: Artificial sequence
<220> FEATURE:
<223> OTHER INFORMATION: Engineered sequence

<400> SEQUENCE: 213
atgaatggtg aaaccagtcg tccgccggca ctgggtttta gcagcgaaaa cattgcaggc      60
```

```
gcaagtccgg aagttgcgca agcactggtt aaacatagct ctggtcgtaa attctgcgag    120
atcttcgagc gcgacgttga agtttttctg gttccgaccg gtaccgctgc taacgcactg    180
tgtctgtctg caatgacccc gccgtggggt aatatttatt gccaccatgc aagccatatt    240
aataacgacg agtgcggcgc accggaattt ttcagcaacg cgccaaaact gatgaccgtt    300
gacggtccgg cagcaaaact ggatattgta cgtctgcgcg aacgtaccag cgaaaaagtt    360
ggcgacgttc ataccaccca accggcttgc gttagtatta cccaggcaac cgaagttggt    420
agcatctata ccctggacga aatcgaagcg attggcgacg tctgcaaaag tagtagtctg    480
ggcctgcata tggacggtag tcgttttgcg aacgcactgg ttagtctggg ttgttctccg    540
gcagaaatga cctggaaagc aggtgttgac gcactgagtt ttggcgcaac caaaaacggc    600
gttctggctg cagaagcaat tgttctgttt aacaccagcc tggccaccga atgagctat    660 cgtcgtaaac gcgcaggtca tctgattagc aaacatcgtt tcctgagcgc acagattgac    720
gcatatctga ccgacgatct gtggctgcgt aacgcacgta agcaaacgc agcagcacaa    780 cgtctggcac aaggtctgga aggtctgggc ggcgttgaag ttctgggcgg taccgaagca    840
aacattctgt tctgccgtat ggactctccg atgattgacg cactgctgaa agcgggcttt    900
aaatttggct atgaacgctg gggtccgaac gttgttcgtt ttgtcaccag ctttgcaacc    960
accgcagaag acgttgatca tctgctgaac caagttcgtc tggcagcaga tcgtacccaa   1020
gaacgt                                                             1026
```

<210> SEQ ID NO 214  
<211> LENGTH: 342  
<212> TYPE: PRT  
<213> ORGANISM: Artificial sequence  
<220> FEATURE:  
<223> OTHER INFORMATION: Engineered sequence

<400> SEQUENCE: 214

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Arg Lys Phe Cys Glu Ile Phe Glu Arg Asp Val Glu Val
        35                  40                  45

Phe Leu Val Pro Thr Gly Thr Ala Ala Asn Ala Leu Cys Leu Ser Ala
    50                  55                  60

Met Thr Pro Pro Trp Gly Asn Ile Tyr Cys His His Ala Ser His Ile
65                  70                  75                  80

Asn Asn Asp Glu Cys Gly Ala Pro Glu Phe Phe Ser Asn Gly Ala Lys
                85                  90                  95

Leu Met Thr Val Asp Gly Pro Ala Ala Lys Leu Asp Ile Val Arg Leu
            100                 105                 110

Arg Glu Arg Thr Ser Glu Lys Val Gly Asp Val His Thr Thr Gln Pro
        115                 120                 125

Ala Cys Val Ser Ile Thr Gln Ala Thr Glu Val Gly Ser Ile Tyr Thr
    130                 135                 140

Leu Asp Glu Ile Glu Ala Ile Gly Asp Val Cys Lys Ser Ser Ser Leu
145                 150                 155                 160

Gly Leu His Met Asp Gly Ser Arg Phe Ala Asn Ala Leu Val Ser Leu
                165                 170                 175

Gly Cys Ser Pro Ala Glu Met Thr Trp Lys Ala Gly Val Asp Ala Leu
```

```
                180               185               190
Ser Phe Gly Ala Thr Lys Asn Gly Val Leu Ala Ala Glu Ala Ile Val
            195                 200                 205
Leu Phe Asn Thr Ser Leu Ala Thr Glu Met Ser Tyr Arg Arg Lys Arg
            210                 215                 220
Ala Gly His Leu Ile Ser Lys His Arg Phe Leu Ser Ala Gln Ile Asp
225                 230                 235                 240
Ala Tyr Leu Thr Asp Asp Leu Trp Leu Arg Asn Ala Arg Lys Ala Asn
                245                 250                 255
Ala Ala Ala Gln Arg Leu Ala Gln Gly Leu Glu Gly Leu Gly Gly Val
            260                 265                 270
Glu Val Leu Gly Gly Thr Glu Ala Asn Ile Leu Phe Cys Arg Met Asp
            275                 280                 285
Ser Pro Met Ile Asp Ala Leu Leu Lys Ala Gly Phe Lys Phe Gly Tyr
            290                 295                 300
Glu Arg Trp Gly Pro Asn Val Val Arg Phe Val Thr Ser Phe Ala Thr
305                 310                 315                 320
Thr Ala Glu Asp Val Asp His Leu Leu Asn Gln Val Arg Leu Ala Ala
                325                 330                 335
Asp Arg Thr Gln Glu Arg
            340

<210> SEQ ID NO 215
<211> LENGTH: 1038
<212> TYPE: DNA
<213> ORGANISM: Artificial sequence
<220> FEATURE:
<223> OTHER INFORMATION: Engineered sequence

<400> SEQUENCE: 215
atgaatggtg aaaccagtcg tccgccggca ctgggtttta gcagcgaaaa cattgcaggc      60
gcaagtccgg aagttgcgca agcactggtt aaacatagct ctggtcaagc agatccgcgt     120
aaattctgcg agatcttcga gcgcgacgtt gaagttttc tggttccgac cggtaccgct      180
gctaacgcac tgtgtctgtc tgcaatgacc ccgccgtggg gtaatattta ttgccaccat     240
gcaagccata ttaataacga cgagtgcggc gcaccggaat ttttcagcaa cggcgccaaa     300
ctgatgaccg ttgacggtcc ggcagcaaaa ctggatattg tacgtctgcg cgaacgtacc     360
agcgaaaaag ttggcgacgt tcataccacc caaccggctt gcgttagtat tacccaggca     420
accgaagttg gtagcatcta tccctggac gaaatcgaag cgattggcga cgtctgcaaa      480
agtagtagtc tgggcctgca tatggacggt agtcgttttg cgaacgcact ggttagtctg     540
ggttgttctc cggcagaaat gacctggaaa gcaggtgttg acgcactgag ttttggcgca     600
accaaaaacg gcgttctggc tgcagaagca attgttctgt taacaccag cctggccacc      660 gaaatgagct atcgtcgtaa acgcgcaggt catctgatta gcaaacatcg tttcctgagc     720
gcacagattg acgcatatct gaccgacgat ctgtggctgc gtaacgcacg taaagcaaac     780
gcagcagcac aacgtctggc acaaggtctg gaaggtctgg cggcgttga agttctgggc      840 ggtaccgaag caaacattct gttctgccgt atggactctc cgatgattga cgcactgctg     900
aaagcgggct ttaaatttgg ctatgaacgc tggggtccga cgttgttcg ttttgtcacc      960 agctttgcaa ccaccgcaga agacgttgat catctgctga accaagttcg tctggcagca    1020
gatcgtaccc aagaacgt                                                  1038
```

```
<210> SEQ ID NO 216
<211> LENGTH: 346
<212> TYPE: PRT
<213> ORGANISM: Artificial sequence
<220> FEATURE:
<223> OTHER INFORMATION: Engineered sequence

<400> SEQUENCE: 216

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Asp Pro Arg Lys Phe Cys Glu Ile Phe Glu Arg
        35                  40                  45

Asp Val Glu Val Phe Leu Val Pro Thr Gly Thr Ala Ala Asn Ala Leu
    50                  55                  60

Cys Leu Ser Ala Met Thr Pro Pro Trp Gly Asn Ile Tyr Cys His His
65                  70                  75                  80

Ala Ser His Ile Asn Asn Asp Glu Cys Gly Ala Pro Glu Phe Phe Ser
                85                  90                  95

Asn Gly Ala Lys Leu Met Thr Val Asp Gly Pro Ala Ala Lys Leu Asp
            100                 105                 110

Ile Val Arg Leu Arg Glu Arg Thr Ser Glu Lys Val Gly Asp Val His
        115                 120                 125

Thr Thr Gln Pro Ala Cys Val Ser Ile Thr Gln Ala Thr Glu Val Gly
    130                 135                 140

Ser Ile Tyr Thr Leu Asp Glu Ile Glu Ala Ile Gly Asp Val Cys Lys
145                 150                 155                 160

Ser Ser Ser Leu Gly Leu His Met Asp Gly Ser Arg Phe Ala Asn Ala
                165                 170                 175

Leu Val Ser Leu Gly Cys Ser Pro Ala Glu Met Thr Trp Lys Ala Gly
            180                 185                 190

Val Asp Ala Leu Ser Phe Gly Ala Thr Lys Asn Gly Val Leu Ala Ala
        195                 200                 205

Glu Ala Ile Val Leu Phe Asn Thr Ser Leu Ala Thr Glu Met Ser Tyr
    210                 215                 220

Arg Arg Lys Arg Ala Gly His Leu Ile Ser Lys His Arg Phe Leu Ser
225                 230                 235                 240

Ala Gln Ile Asp Ala Tyr Leu Thr Asp Leu Trp Leu Arg Asn Ala
                245                 250                 255

Arg Lys Ala Asn Ala Ala Gln Arg Leu Ala Gln Gly Leu Glu Gly
            260                 265                 270

Leu Gly Gly Val Glu Val Leu Gly Gly Thr Glu Ala Asn Ile Leu Phe
        275                 280                 285

Cys Arg Met Asp Ser Pro Met Ile Asp Ala Leu Leu Lys Ala Gly Phe
    290                 295                 300

Lys Phe Gly Tyr Glu Arg Trp Gly Pro Asn Val Val Arg Phe Val Thr
305                 310                 315                 320

Ser Phe Ala Thr Thr Ala Glu Asp Val Asp His Leu Leu Asn Gln Val
                325                 330                 335

Arg Leu Ala Ala Asp Arg Thr Gln Glu Arg
            340                 345
```

ENGINEERED ALDOLASE POLYPEPTIDES AND USES THEREOF

PRIORITY

This application corresponds to the U.S. National phase of International Application No. PCT/CN2018/086228, filed May 9, 2018, which, in turn, claims priority to Chinese Patent Application No. 2017-10386955.9 filed May 27, 2017 and Chinese Patent Application No. 2017-10405791.X filed May 27, 2017, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Nov. 22, 2019, is named LNK_204 US_SEQ_listing.txt and is 527,505 bytes in size.

TECHNICAL FIELD

The present invention relates to the field of biotechnology, in particular to engineered aldolase polypeptides and their application in industrial biocatalysis.

BACKGROUND TECHNIQUE

β-hydroxy-α-amino acids are a kind of important amino acids which are critical intermediates to produce a variety of natural products and drugs. They have many important biological activities. The chemical structure of these compounds generally has two chiral centers with multiple stereoisomers (Scheme 1). Current synthesis routes of β-hydroxy-α-amino acids are based on organic chemistry and usually result in poor stereoselectivity, which necessitates tedious and costly resolution and purification steps. In addition, high usage of reagents and large volumes of waste generation exists in the resolution and purification steps, thus resulting in a total low yield and great environmental burden. Therefore, the development of asymmetric synthesis of β-hydroxy-α-amino acid is in great demand. It has been reported that aldolase can condense aldehydes and amino acids to form β-hydroxy-α-amino acids. The condition of this enzymatic reaction is mild and results in little pollution. However, the stereoselectivity of wild-type aldolases is not good enough to meet industrial application request. The present invention provides a series of engineered polypeptides with high stereoselectivity. These engineered polypeptides were developed through directed evolution towards the selection of (2S,3R)-2-amino-3-hydroxy-3-[4(methylsulfonyl)phenyl] propanoic acid, a compound of structural formula A2 shown in Scheme 2.

Brief Description of the Schemes

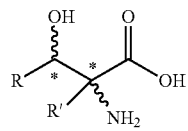

Scheme 1 shows a general formula of β-hydroxy-α-amino acids (* refers to chiral center).

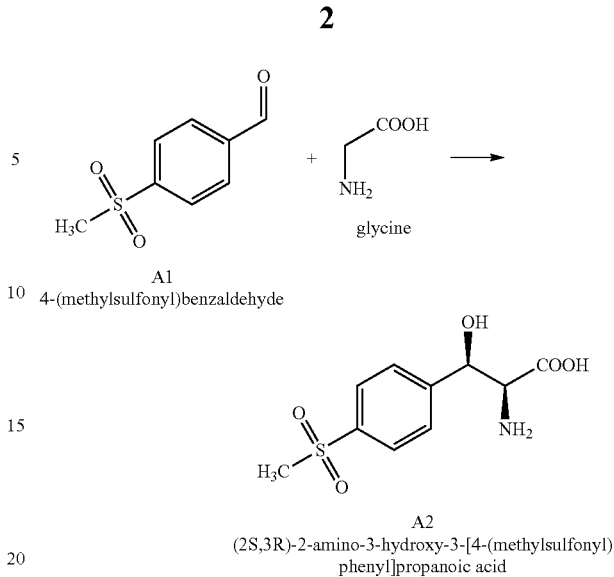

Scheme 2 shows the synthesis of a compound of formula A2 by an asymmetric reaction catalyzed by an engineered aldolase polypeptide of the present invention.

SUMMARY OF THE INVENTION

The present invention provides engineered polypeptides with high stereoselectivity, high catalytic activity and good stability, which can asymmetrically synthesize β-hydroxy-α-amino acids, and in particular asymmetrically synthesize (2S,3R)-2-amino-3-hydroxy-3-[4-(methylsulfonyl)phenyl] propanoic acid. The present invention also provides gene sequences of engineered polypeptides, recombinant expression vectors containing the genes, engineered strains and efficient methods for the production thereof, as well as reaction processes for the asymmetric synthesis of β-hydroxy-α-amino acids using engineered polypeptides.

In the first aspect, the present invention provides engineered aldolase polypeptides with improved catalytic properties. Through substitutions, insertions, or deletions of a number of amino acid residues in directed evolution process, these engineered polypeptides were derived from a wild-type aldolase which is less stereoselective towards the product. The wild-type aldolase is from *Pseudomonas putida* which consists of 357 amino acids and has the sequence shown in SEQ ID No: 2. The wild-type aldolase showed low stereoselectivity for the product. As measured by the inventors, in the reaction of converting 4-(methylsulfonyl)benzaldehyde (i.e. A1) with glycine to produce (2S,3R)-2-amino-3-hydroxy-3-[4-(methylsulfonyl)phenyl] propanoic acid (i.e. A2) in Scheme 2 using SEQ ID No: 2, the diastereomeric excess number (i.e. de) for A2 is ≤52%.

In some embodiments, engineered aldolase polypeptides of the present disclosure are capable of converting A1 and glycine to A2 at a stereoselectivity at least equal to or greater than that of SEQ ID No: 2. Under the indicated reaction conditions, the engineered aldolase polypeptides of the present disclosure are capable of producing A2 in a diastereomeric excess of at least 60%, 65%, 70%, 75%, 80%, 85%, 90%, 91%, 92%, 93% 94%, 95%, 96%, 97%, 98% or 99%. In some embodiments, the reaction conditions comprise 20% organic solvent (including but not limited to dimethyl sulfoxide, ethanol or methanol) and temperature of about 30° C. and a pH of about 6.0.

In some embodiments, the engineered aldolase polypeptides are capable of converting A1 and glycine to A2 at a stereoselectivity higher than that of the polypeptide of SEQ ID NO: 2 under the indicated reaction conditions. The engineered aldolase polypeptides comprise an amino acid sequence that is at least 80%, 85%, 86%, 87%, 88%, 89%, 90%, 91%, 92%, 93%, 94%, 95%, 96%, 97%, 98%, 99% or more identical to the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216.

The identity between two amino acid sequences or two nucleotide sequences can be obtained by commonly used algorithms in the art and can be calculated according to default parameters by using NCBI Blastp and Blastn software, or by using the Clustal W algorithm (Nucleic Acid Research, 22 (22): 4673-4680, 1994). For example, using the Clustal W algorithm, the amino acid sequence identity of SEQ ID NO: 2 to SEQ ID NO: 4 is 94.4%, the amino acid sequence identity of SEQ ID NO: 2 to SEQ ID NO: 182 is 90.7%.

In some embodiments, engineered aldolase polypeptides comprise an amino acid sequence with insertions of one or more than one amino acid residues in SEQ ID NO: 2 and having aldolase activity. For each and every embodiment of the engineered aldose polypeptides of the present disclosure, the insertion fragment may comprise 1 or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, where the relevant functional and/or improved properties of the engineered aldolase described herein are maintained. The insertion fragment can be inserted at the amino terminus or carboxy terminus, or the internal portion of the aldolase polypeptide. In some embodiments, the insertion fragments may comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 amino acid residues. In some embodiments, the number of insertion occurrence can be 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more. In some embodiments, the insertion fragments may comprise 1, 2, 3, 4, 5, 6, 7, 8, 9, 10, 11, 12, 13, 14, 15, 16, 17, 18, 19, 20, 21, 22, 23, 24, 25 or more amino acid residues.

In some embodiments, the engineered aldolase polypeptide SEQ ID NO: 4 has an inserted fragment of 19 amino acid residues within the sequence of SEQ ID No: 2. In some embodiments, the further engineered aldolase polypeptides comprise an amino acid sequence that differs from the sequence of SEQ ID NO: 4 in one or more residue positions selected from: X16, X18, X19, X37, X38, X41, X42, X43, X57, X61, X86, X106, X110, X130, X151, X152, X159, X198, X201, X249, X256, X263, X266, X310, X327, X335, X337, X338, X339, X346. In some embodiments, the further engineered aldolase polypeptide comprise an amino acid sequence comprising at least one of the following features (these features are substitutions of amino acid residues to the reference sequence of SEQ ID NO: 4): D16E, I18Y, I18W, A19V, A37P, G38F, G38Y, G38D, G41D, T42P, D43V, G57D, G57K, T61N, T61K, T61H, T61F, P86G, P86A, I106N, P110A, P110H, P110R, K130R, R151K, R151S, R151N, E152W, T159S, M198I, S201A, A249V, R256H, S263V, S263H, S263T, S263L, S263I, M266Y, G310C, D327E, G335T, G335K, G335R, Y337V, Y337G, Y337I, H338Y, H338T, H338S, H338N, D339R, D339K, D339E, D339G, V346C.

More specifically, in some embodiments, the engineered aldolase polypeptides which were improved over SEQ ID NO: 4 comprise a sequence corresponding to SEQ ID No: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184.

In some embodiments, the engineered aldolase polypeptides comprise an amino acid sequence that differs from the sequence of SEQ ID NO: 2 in one or more residue positions selected from: X16, X18, X19, X37, X38, X41, X42, X43, X67, X87, X91, X111, X132, X133, X140, X179, X182, X230, X237, X244, X247, X291, X302, X305, X308, X316, X318, X319, X320, X327; more specifically, the engineered aldolase polypeptides comprise an amino acid sequence comprising at least one of the following features (these features are substitutions of amino acid residues to the reference sequence of SEQ ID NO: 2): D16E, I18Y, I18W, A19V, A37P, G38F, G38Y, G38D, G38K, G41D, G41F, G41Q, G41H, T42P, T42N, T42K, T42H, T42F, T42M, D43V, P67G, P67A, I87N, P91A, P91H, P91R, K111R, R132K, R132S, R132N, E133W, T140s, M179I, S182A, A230V, R237H, S244V, S244H, S244T, S244L, S244I, M247Y, M247H, G291C, L302M, A305P, D308E, G316T, G316K, G316R, Y318V, Y318G, Y318I, H319Y, H319T, H319S, H319N, D320R, D320K, D320E, D320G, V327C; Or, in addition to the abovementioned differences, engineered aldolase polypeptides comprise insertions or deletions of 1, 2, 3, 4, 5, 6, 7, 8, 9, 10, 11, 12, 13, 14, 15, 16, 18, 19, 20, 21, 22, 23, 24, 25 or 30 of amino acid residues. In some embodiments, the engineered aldolase polypeptides comprise the amino acid sequence of those corresponding to SEQ ID No: 186, 188, 190, 192, 194, 196, 198, 200, 202, 204, 206, 208, 210, 212, 214, 216.

In another aspect, this invention provides polynucleotide sequences encoding engineered aldolase polypeptides. In some embodiments, a polynucleotide can be part of an expression vector having one or more control sequences for the expression of an engineered aldolase polypeptide. In some embodiments, polynucleotides comprise sequences corresponding to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215.

As known to people skilled in the art, due to the degeneracy of the nucleotide codons, the polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216 are not limited to SEQ ID No: 3, 5, 7, 9, 11, 13, 15, 17, 19, 21, 23, 25, 27, 29, 31, 33, 35, 37, 49, 41, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215. The polynucleotide sequences of the engineered polypeptides of the present invention may also be any other polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216.

In another aspect, this disclosure provides polynucleotides comprising sequences encoding engineered aldolase polypeptides, expression vectors and host cells capable of expressing engineered aldolase polypeptides. In some embodiments, the host cell can be bacterial host cell, such as *E. coli*. The host cell can be used to express and isolate the engineered aldolase described herein, or alternatively be directly used in the reaction for conversion of substrates to products. In some embodiments, the engineered aldolase in the form of whole cell, crude extract, isolated enzyme, or purified enzyme can be used alone or in an immobilized form, such as immobilization on a resin.

The present disclosure also provides the process of the asymmetric synthesis of β-hydroxy-α-amino acid compounds using the herein disclosed engineered aldolase polypeptides, the resulting β-hydroxy-α-amino acid products having the structure shown in Formula (I):

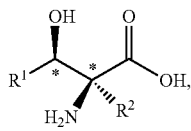
(I)

where the β-hydroxy-α-amino acid products of formula (I) have the indicated stereochemical configuration shown at the chiral center marked with *; the β-hydroxy-α-amino acid products of formula (I) are in diastereomeric excess over the other isomers, where $R^1$ is optionally substituted or unsubstituted aryl or heteroaryl, or optionally substituted or unsubstituted $C_1$-$C_8$ hydrocarbyl;

$R^2$ is —H, —CH$_2$OH, —CH$_2$SH, —CH$_2$SCH$_3$, or optionally substituted or unsubstituted $C_1$-$C_4$ hydrocarbyl, the process comprising that, under suitable reaction conditions of reacting the aldehyde substrate and the amino acid substrate to obtain β-hydroxy-α-amino acid products, the aldehyde substrate of formula (II) and the amino acid substrate of formula (III):

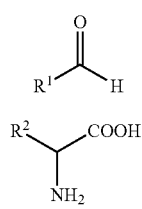
(II)

(III)

were contacted with the aldolase polypeptides, wherein the aldolase polypeptides are engineered aldolase polypeptides described herein. In some embodiments, the engineered aldolase polypeptides have at least 80%, 85%, 86%, 87%, 88%, 89%, 90%, 91%, 92%, 93%, 94%, 95%, 96%, 97%, 98%, 99% or more of sequence identity to SEQ ID NO: 2 and are capable of converting the aldehyde substrate of formula (II) and the amino acid substrate of formula (III) to obtain the β-hydroxy-α-amino acid products of formula (I) at higher conversion or higher stereoselectivity compared to SEQ ID NO: 2.

In some embodiments, the β-hydroxy-α-amino acid product of formula (I) is produced in a diastereomeric excess of at least 60%, 65%, 70%, 75%, 80%, 85%, 90%, 91%, 92%, 93%, 94%, 95%, 96%, 97%, 98%, or 99% or greater.

In some embodiments of this process, the β-hydroxy-α-amino acid products of formula (I) are:

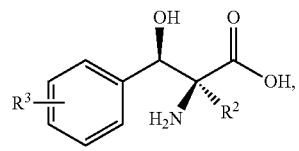

wherein $R^3$ is $C_1$-$C_4$ hydrocarbyl, —H, halogen such as —F, —Cl, —Br and —I, —NO$_2$, —NO, —SO$_2$R', —SOR', —SR', —NR'—C(O)NR', —SO$_2$NH$_2$ or —SONH$_2$, —CN, CF$_3$, wherein each R' is independently selected from —H or ($C_1$-$C_4$) hydrocarbyl;

$R^3$ may also be

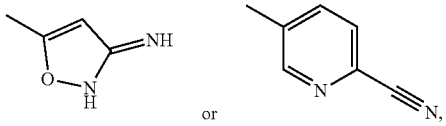

$R^2$ is —H, —CH$_3$, —CH$_2$CH$_3$, —CH(CH$_3$)$_2$, —CH$_2$OH, —CH$_2$SH or —CH$_2$SCH$_3$, and the aldehyde substrate of formula (II) is:

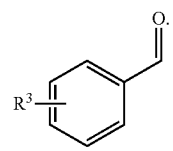

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring. In some embodiments of this process, the β-hydroxy-α-amino acid product of formula (I) is:

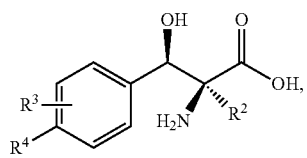

Wherein $R^4$ is defined same as $R^3$ above, $R^3$ and $R^2$ are as defined above, and the aldehyde substrate of formula (II) is:

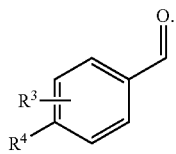

In some embodiments, $R^3$ is in the meta position of the phenyl ring. In some embodiments, $R^3$ is ortho to the phenyl ring.

In some embodiments, the engineered aldolase polypeptides can be used in the production process of diastereomeric excess of the compound of formula A2, (2S,3R)-2-amino-3-hydroxy-3-[4-(methylsulfonyl)phenyl] propanoic acid:

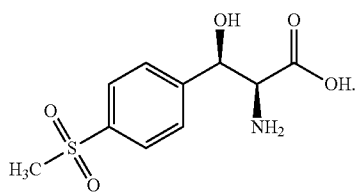

In these embodiments, the production process comprises that, under suitable reaction conditions for converting compound of formula A1 to compound of formula A2, in a suitable organic solvent, in the presence of glycine, the compound of formula A1:

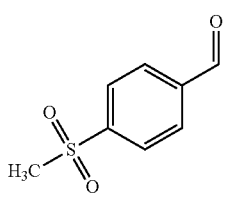

were contacted with the engineered aldolase polypeptides disclosed herein.

In some embodiments of the above process, the compound of formula (I) or the compound of formula A2 is present in a diastereomeric excess of at least 60%, 65%, 70%, 75%, 80%, 85%, 90%, 91%, 92%, 93% 94%, 95%, 96%, 97%, 98% or 99% or more.

Specific embodiments of engineered aldolase polypeptides for use in this method are further provided in the detailed description. An engineered aldolase polypeptide that can be used in the above process can comprise one or more sequences selected from the amino acid sequences corresponding to SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216. In another aspect, this disclosure provides a process of producing (2S,3R)-2-amino-3-hydroxy-3-[4-(methylsulfonyl)phenyl] propanoic acid using an engineered aldolase polypeptide disclosed herein. In some embodiments, the process comprises that, under suitable reaction conditions for converting 4-(methylsulfonyl) benzaldehyde to (2S,3R)-2-amino-3-hydroxy-3-[4-(methylsulfonyl)phenyl] propanoic acid, in the presence of glycine, the 4-(methylsulfonyl)benzaldehyde is contacted with the engineered aldolase polypeptides described herein.

Any of the processes for the production of a compound of formula (I) or a compound of formula A2 using an engineered polypeptide as disclosed herein can be performed under a range of suitable reaction conditions, which including, but not limited to, amino donor, pH, temperature, buffer, solvent system, substrate loading, polypeptide loading, cofactor loading, pressure and reaction time range. For example, in some embodiments, preparing a compound of formula (I) or a compound of formula A2 may be performed, wherein suitable reaction conditions include: (a) about 10 g/L to 200 g/L of a substrate compound (e.g. compound (II) or A1); (b) about 0.5 g/L to 10 g/L of engineered polypeptide; (c) about 30 g/L to 300 g/L of glycine loading; (d) about 0.1 mM-5 mM PLP cofactor; (e) from 0% (v/v) to about 60% (v/v) of organic solvent, including but not limited to, dimethylsulfoxide (DMSO), Dimethylformamide (DMF), isopropyl acetate, methanol, ethanol, propanol or isopropanol (IPA); (F) a pH of about 4.0 to about 8.0; and (g) a temperature of about 10° C. to about 60° C.

In some embodiments, the process is capable of forming the product (2S,3R)-2-amino-3-hydroxy-3-[4-(methylsulfonyl)phenyl] propanoic acid in a diastereomeric excess of at least 60%.

In some embodiments, the process is capable of forming the product (2S,3R)-2-amino-3-hydroxy-3-[4-(methylsulfonyl)phenyl] propanoic acid in a diastereomeric excess of at least 70%.

In some embodiments, the process is capable of forming the product (2S,3R)-2-amino-3-hydroxy-3-[4-(methylsulfonyl)phenyl] propanoic acid in a diastereomeric excess of at least 80%.

In some embodiments, the process is capable of forming the product (2S,3R)-2-amino-3-hydroxy-3-[4-(methylsulfonyl)phenyl] propanoic acid in a diastereomeric excess of at least 85%.

In some embodiments, the process is capable of forming the product (2S,3R)-2-amino-3-hydroxy-3-[4-(methylsulfonyl)phenyl] propanoic acid in a diastereomeric excess of at least 90%.

In some embodiments, the process is capable of forming the product (2S,3R)-2-amino-3-hydroxy-3-[4-(methylsulfonyl)phenyl] propanoic acid in a diastereomeric excess of at least 95%.

In some embodiments, the process is capable of forming the product (2S,3R)-2-amino-3-hydroxy-3-[4-(methylsulfonyl)phenyl] propanoic acid in a diastereomeric excess of at least 99%.

DETAILED DESCRIPTION OF THE INVENTION

1. Definitions

Unless expressly defined otherwise, technical and scientific terms used in this disclosure have the meanings that are commonly understood by people skilled in the art.

"Protein", "polypeptide" and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.). This definition includes D-amino acids and L-amino acids, as well as mixtures of D-amino acids and L-amino acids.

"Engineered aldolase", "engineered aldolase polypeptide", "aldolase polypeptide", "improved aldolase polypeptide", and "engineered polypeptide" are used interchangeably herein.

"Polynucleotide" and "nucleic acid" are used interchangeably herein.

"Cofactor" as used herein refers to a non-protein compound that operates in conjunction with an enzyme in a catalytic reaction. As used herein, "cofactor" is intended to encompass the vitamin B6 family compounds PLP, PN, PL, PM, PNP and PMP, which are sometimes also referred to as coenzymes.

"Pyridoxal phosphate", "PLP", "pyridoxal 5'-phosphate", "PYP" and "P5P" are used interchangeably herein to refer to compounds that act as coenzyme in aldolase reactions.

"Coding sequence" refers to that portion of a nucleic acid (e.g., a gene) that encodes an amino acid sequence of a protein.

"Naturally occurring" or "wild-type" refers to the form found in nature. For example, a naturally-occurring or wild-type polypeptide or polynucleotide sequence is a sequence that is present in an organism that can be isolated from sources in nature and which has not been intentionally modified by manual procedures.

"Recombinant" or "engineered" or "non-naturally occurring" when used with reference to, for example, a cell, nucleic acid or polypeptide, refers to a material or material corresponding to the native or native form of the material, that has been modified in a manner that would not otherwise exist in nature, or is identical thereto but produced or derived from synthetic material and/or by manipulation using recombinant techniques.

"Sequence identity" and "homology" are used interchangeably herein to refer to comparisons between polynucleotide sequences or polypeptide sequences ("sequence identity" and "homology" are generally expressed as a percentage), and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage can be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those skilled in the art will appreciate that there are many established algorithms available to align two sequences. The optimal alignment of sequences for comparison can be conducted, for example, by the local homology algorithm of Smith and Waterman, 1981, Adv. Appl. Math. 2: 482, by the Homology alignment algorithm of Needleman and Wunsch, 1970, J. Mol. Biol. 48: 443, by the search for similarity method of Pearson and Lipman, 1988, Proc. Natl. Acad. Sci. USA 85: 2444, by computerized implementations of these algorithms (GAP, BESTFIT, FASTA, and TFASTA in the GCG Wisconsin Package) or by visual inspection (see generally, Current Protocols in Molecular Biology, FM Ausubel et al. eds., Current Protocols, a Joint Venture between Greene Publishing Associates, Inc. and John Wiley & Sons, Inc., (1995 Supplement) (Ausubel)). Examples of algorithms that are suitable for determining the percent sequence identity and percent sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analysis is publicly available through the National Center for Biotechnology Information website. The algorithm involves first identifying high scoring sequence pairs (HSPS) by identifying short words of length W in the query sequence, which either match or satisfy some positive-valued threshold scores T when aligned with a word of the same length in the database sequence. T is referred to as, the neighborhood word score threshold (Altschul et al., Supra). These initial neighborhood word hits serve as seeds for initiating searches to find longer HSPs that contain them. The word hits are then extended in both directions along each sequence for as far as the cumulative alignment score can be increased. For nucleotide sequences, the cumulative scores are calculated using the parameters M (reward score for matched pair of residues; always >0) and N (penalty score for mismatched residues; always <0). For amino acid sequences, a scoring matrix is used to calculate the cumulative score. The extension of the word hits in each direction are halted when: the cumulative alignment score falls off by the quality X from its maximum achieved value; the cumulative score goes 0 or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, the expected value (E) of 10, M=5, N=−4, and a comparison of both strands as a default value. For amino acid sequences, the BLASTP program uses as defaults the wordlength (W) of 3, the expected value (E) of 10 and the BLOSUM62 scoring matrix (see Henikoff and Henikoff, 1989, Proc Natl Acad Sci USA 89: 10915). Exemplary determination of sequence alignments and % sequence identity can employ the BESTFIT or GAP programs in the GCG Wisconsin Software package (Accelrys, Madison Wis.), using the default parameters provided.

"Reference sequence" refers to a defined sequence that is used as a basis for sequence comparison. The reference sequence may be a subset of a larger sequence, for example, a full-length gene or a fragment of a polypeptide sequence. In general, a reference sequence is at least 20 nucleotides or amino acid residues in length, at least 25 residues long, at least 50 residues in length, or the full length of the nucleic acid or polypeptide. Because two polynucleotides or polypeptides may each (1) comprise a sequence (i.e., a portion of the complete sequence) that is similar between two sequences, and (2) may further comprise sequences that is divergent between the two sequences, sequence comparisons between two (or more) polynucleotides or polypeptides are typically performed by comparing the sequences of the two polynucleotides or polypeptides over a "comparison window" to identify and compare local regions of sequence similarity. In some embodiments, a "reference sequence" is not intended to be limited to a wild-type sequence, and may comprise engineered or altered sequences. For example, "a reference sequence with proline at the residue corresponding to X37 based on SEQ ID NO: 2" refers to a reference sequence wherein the corresponding residue at position X37 in SEQ ID NO: 2 which is alanine, has been altered to proline.

A "comparison window" refers to a conceptual segment of at least about 20 contiguous nucleotide positions or amino acid residues, wherein the sequence may be compared to a reference sequence of at least 20 contiguous nucleotides or amino acids and wherein the portions of the sequence in the comparison window may comprise additions or deletions (i.e., gaps) of 20% or less as compared to a reference sequence (which does not comprise additions or deletions) for optimal alignment of the two sequences. The comparison window can be longer than 20 contiguous residues, and optionally include 30, 40, 50, 100 or more residues.

In the context of the numbering for a given amino acid or polynucleotide sequence, "corresponding to," "reference to" or "relative to" refers to the numbering of the residues of a specified reference when the given amino acid or polynucleotide sequence is compared to the reference sequence. In other words, the residue number or residue position of a given sequence is designated with respect to the reference sequence, rather than by the actual numerical position of the residue within the given amino acid or polynucleotide sequence. For example, a given amino acid sequence such as an engineered aldolase can be aligned to a reference sequence by introducing gaps to optimize residue matches between the two sequences. In these cases, although there are gaps, the numbering of the residue in a given amino acid or polynucleotide sequence is made with respect to the reference sequence to which they have been aligned.

"Amino acid difference" or "residue difference" refers to the difference in amino acid residues at a position of a polypeptide sequence relative to the amino acid residue at a corresponding position in the reference sequence. The positions of amino acid differences are generally referred to herein as "Xn", where n refers to the corresponding position in the reference sequence on which the residue differences are based. For example, "a residue difference at position X38 as compared to SEQ ID NO: 4" refers to the difference in amino acid residues at the polypeptide position corresponding to position 38 of SEQ ID NO: 4. Thus, if the reference polypeptide of SEQ ID NO: 4 has a glycine at position 38, then "a residue difference at position X38 as compared to SEQ ID NO: 4" refers to an amino acid substitution of any residue other than glycine at the position of the polypeptide corresponding to position 38 of SEQ ID NO: 4. In most of the examples herein, the specific amino acid residue difference at the position is indicated as "XnY", wherein "Xn" specified to the corresponding position as described above, and "Y" is the single letter identifier of the amino acid found in the engineered polypeptide (i.e., a different residue than in the reference polypeptide). In some examples (e.g., in Table 1), the present disclosure also provides specific amino acid differences denoted by the conventional notation "AnB", where A is a single letter identifier of a residue in the reference sequence, "n" is the number of residue position in the reference sequence, and B is the single letter identifier for the residue substitution in the sequence of the engineered polypeptide. In some examples, an engineered polypeptide of this disclosure may comprise one or more amino acid residue differences relative to a reference sequence, which is indicated by a list of specific positions at which residue differences are present relative to a reference sequence. In some embodiments, more than one amino acid residue can be used in a specific residue position of an engineered polypeptide, the various amino acid residues that can be used are separated by a "/" (e.g., X38F/X38F).

"Deletion" refers to the modification of a polypeptide by removing one or more amino acids from a reference polypeptide. Deletions can include the removal of one or more amino acids, two or more amino acids, five or more amino acids, ten or more amino acids, fifteen or more amino acids, or twenty or more amino acids, up to 10% of the total number of amino acids of the enzyme, or up to 20% of the total number of amino acids making up the reference enzyme while retaining the enzymatic activity of the engineered aldolase and/or retaining the improved properties of the engineered aldolase. Deletion may involve the internal portion and/or the terminal portion of the polypeptide. In various embodiments, deletions may include a contiguous segment or may be discontinuous.

"Insertion" refers to the modification of a polypeptide by adding one or more amino acids from a reference polypeptide. In some embodiments, the improved engineered aldolase comprises insertions of one or more amino acids to a naturally-occurring aldolase polypeptide as well as insertions of one or more amino acids to other engineered aldolase polypeptides. It can be inserted in the internal portions of the polypeptide or inserted to the carboxyl or amino terminus. As used herein, insertions include fusion proteins known in the art. The insertion can be a contiguous segment of amino acids or separated by one or more amino acids in naturally-occurring or engineered polypeptides.

"Fragment" as used herein refers to a polypeptide having an amino terminal and/or carboxyl terminal deletion, but where the remaining amino acid sequence is identical to the corresponding position in the sequence. Fragments may be at least 10 amino acids long, at least 20 amino acids long, at least 50 amino acids long or longer, and up to 70%, 80%, 90%, 95%, 98% and 99% of the full length aldolase polypeptide.

An "isolated polypeptide" refers to a polypeptide that is substantially separated from other substances with which it is naturally associated, such as proteins, lipids, and polynucleotides. The term comprises polypeptides that have been removed or purified from their naturally occurring environment or expression system (e.g., in host cells or in vitro synthesis). Engineered aldolase polypeptides may be present in the cell, in the cell culture medium, or prepared in various forms, such as lysates or isolated preparations. As such, in some embodiments, the engineered aldolase polypeptide may be an isolated polypeptide.

"Chiral center" refers to a carbon atom connecting four different groups.

"Stereoselectivity" refers to the preferential formation of one stereoisomer over the other in a chemical or enzymatic reaction. Stereoselectivity can be partial, with the formation of one stereoisomer is favored over the other; or it may be complete where only one stereoisomer is formed. When the stereoisomers are enantiomers, the stereoselectivity is referred to as enantioselectivity. It is often reported as "enantiomeric excess" (ee for short). When the stereoisomers are diastereomers, the stereoselectivity is referred to as diastereoselectivity. It is often reported as "diastereomeric excess" (de for short). The fraction, typically a percentage, is generally reported in the art as the diastereomeric excess (i.e., de) derived therefrom according to the following formula: [major diastereomer−minor diastereomer]/[major diastereomer+minor diastereomer]. In some instances, only two diastereomers were detected in the product formed by the engineered aldolase polypeptides of the present disclosure: (2S,3R)-2-amino-3-hydroxy-3-[4-(methylsulfonyl) phenyl] propanoic acid (i.e., A2) and (2S,3S)-2-amino-3- hydroxy-3-[4-(methylsulfonyl)phenyl] propanoic acid (i.e., A3), the de value for A2 in the product is calculated as follows: [A2−A3]/[A2+A3].

"Stereoisomers," "stereoisomeric forms," and similar expressions are used interchangeably herein to refer to all isomers resulting from a difference in orientation of atoms in their space only. It includes enantiomers and compounds that have more than one chiral center and are not mirror images of one another (i.e., diastereomers).

"Improved enzyme properties" refers to an enzyme property that is better or more desirable for a specific purpose as compared to a reference aldolase such as a wild-type aldolase or another improved engineered aldolase. Improved enzyme properties are exhibited by engineered aldolase polypeptides in this disclosure. Enzyme properties that are expected to be improved include, but are not limited to, enzyme activity (which can be expressed as a percentage of substrate conversion), thermal stability, solvent stability, pH activity characteristics, cofactor requirements, tolerance to inhibitors (e.g., substrate or product inhibition), stereospecificity and stereoselectivity (including enantioselectivity or diastereoselectivity).

"Conversion" refers to the enzymatic transformation of a substrate to the corresponding product.

"Percent conversion" or "conversion" refers to the percentage of substrate that is converted to product within a period of time under the specified conditions. Thus, "enzymatic activity" or "activity" of an aldolase polypeptide can be expressed as the "percent conversion" of the substrate to the product.

"Thermostable" means that an aldolase polypeptide that retains similar activity (e.g., greater than 50%) after being exposed to an elevated temperature (e.g., 30-85° C.) for a period of time (0.5-24 h).

"Solvent-stable" refers to an aldolase polypeptide that maintains similar activity (for example more than 50% to 80%) after exposure to varying solvent (ethanol, isopropanol, dimethylsulfoxide (DMSO), tetrahydrofuran, 2-Methyltetrahydrofuran, acetone, toluene, butyl acetate, methyl tert-butyl ether, etc.) for a period of time (e.g., 0.5-24 hours).

"Suitable reaction conditions" refer to those conditions (e.g., enzyme loading, substrate loading, cofactor loading, temperature, pH, buffer, co-solvent, etc.) in the biocatalytic reaction system, under which the aldolase polypeptide of the present disclosure can convert a substrate to a desired product compound. Exemplary "suitable reaction conditions" are provided in the present disclosure and illustrated by examples.

"Hydrocarbyl" refers to a straight or branched hydrocarbon group. The number of subscripts following the symbol "C" specifies the number of carbon atoms that a particular group may contain. For example, "$C_1$-$C_8$" refers to a straight or branched chain hydrocarbyl group having 1 to 8 carbon atoms. Hydrocarbyl groups may optionally be substituted with one or more substituent groups.

"Aryl" means a monovalent aromatic hydrocarbon radical of 6 to about 20 carbon atoms.

"Heteroaryl" and "heteroaromatic" refer to an aryl group in which one or more of the carbon atoms of the parent aromatic ring system is/are replaced by a heteroatom (O, N, or S). "Substituted", when used to modify a specified group or radical, means that one or more hydrogen atoms of the specified group or radical are each replaced, independently of one another, by identical or different substituents. "Substituted hydrocarbyl, aryl, or heteroaryl" refers to a hydrocarbyl, aryl, or heteroaryl group in which one or more hydrogen atoms are replaced by other substituents.

"Optional" or "optionally" means that the described event or circumstance may or may not occur; for example, "optionally substituted aryl" refers to an aryl group that may or may not be substituted, This description includes both substituted aryl groups and unsubstituted aryl groups. As used herein, "compound" refers to any compound encompassed by the structural formulas and/16/47 or chemical names indicated with the compounds disclosed herein. Compounds may be identified by their chemical structure and/or chemical name. When the chemical structure and chemical name conflict, the chemical structure determines the identity of the compound. Unless specifically stated or indicated otherwise, the chemical structures described herein encompass all possible isomeric forms of the described compounds.

2. Improved Engineered Aldolase

Table 1 below illustrates the engineered aldolase polypeptides developed by the present invention. Each row gives the polynucleotide sequence number and amino acid sequence number of a particular engineered aldolase polypeptide, as well as the residue difference compared to SEQ ID No: 4. The level of activity or stereoselectivity of each exemplified engineered aldolase polypeptide is indicated as "+", with the specific meanings given in Table 2.

TABLE 1

| Polynucleotide SEQ ID No | Amino acid SEQ ID No | Residue difference relative to SEQ ID NO: 4 | Activity or Stereoselectivity |
|---|---|---|---|
| 3 | 4 | | + |
| 5 | 6 | A37P; | + |
| 7 | 8 | G38F; | + |
| 9 | 10 | G38Y; | + |
| 11 | 12 | G38D; | + |
| 13 | 14 | T42P; | + |
| 15 | 16 | D43V; | + |
| 17 | 18 | G310C; | + |
| 19 | 20 | D327E; | + |
| 21 | 22 | T61N; | + |
| 23 | 24 | T61K; | + |
| 25 | 26 | T61H; | + |
| 27 | 28 | I18Y; | + |
| 29 | 30 | I18W; | + |
| 31 | 32 | S263V; | + |
| 33 | 34 | S263H; | + |
| 35 | 36 | S263T; | + |
| 37 | 38 | Y337V; | + |
| 39 | 40 | Y337G; | + |
| 41 | 42 | Y337I; | + |
| 43 | 44 | M266Y; | + |
| 45 | 46 | G57D; S263T; M266Y; Y337G; D339R; | ++ |
| 47 | 48 | G57D; T61N; S263T; M266Y; Y337G; D339R; | ++ |
| 49 | 50 | G57K; S263L; Y337G; D339K; | ++ |
| 51 | 52 | G57K; T61N; S263T; Y337G; D339K; | ++ |
| 53 | 54 | G57D; Y337G; D339K; | ++ |
| 55 | 56 | G57D; S263L; Y337G; D339K; | ++ |
| 57 | 58 | G57D; S263T; Y337G; D339K; | ++ |
| 59 | 60 | I18W; G57D; S263V; Y337G; D339K; | ++ |
| 61 | 62 | G57D; S263T; M266Y; Y337G; D339K; | ++ |
| 63 | 64 | Y337G; H338Y; | ++ |
| 65 | 66 | S263T; Y337G; | ++ |
| 67 | 68 | S263T; M266Y; Y337G; D339R; | ++ |
| 69 | 70 | S263V; M266Y; Y337G; | ++ |
| 71 | 72 | S263V; M266Y; Y337G; D339K; | ++ |
| 73 | 74 | S263L; M266Y; Y337G; D339K; | ++ |
| 75 | 76 | G57D; P110A; T159S; S263T; M266Y; Y337G; H338T; D339K; | +++ |

TABLE 1-continued

| Polynucleotide SEQ ID No | Amino acid SEQ ID No | Residue difference relative to SEQ ID NO: 4 | Activity or Stereoselectivity |
|---|---|---|---|
| 77 | 78 | G57D; S263T; M266Y; Y337G; H338T; D339K; | +++ |
| 79 | 80 | G57D; S263T; M266Y; Y337G; H338Y; D339K; | +++ |
| 81 | 82 | G57D; P110A; T159S; S263T; M266Y; Y337G; D339K; | +++ |
| 83 | 84 | G57D; S263I; M266Y; Y337G; D339K; | +++ |
| 85 | 86 | D16E; G57D; S263T; M266Y; Y337G; D339K; | +++ |
| 87 | 88 | G41D; G57D; K130R; S263T; M266Y; Y337G; H338T; D339K; | ++++ |
| 89 | 90 | G57D; M198I; A249V; S263T; M266Y; Y337G; H338T; D339K; | ++++ |
| 91 | 92 | G57D; S263I; M266Y; Y337G; H338S; D339E; | ++++ |
| 93 | 94 | G57D; E152W; T159S; S263T; M266Y; Y337G; H338Y; D339K; | ++++ |
| 95 | 96 | G57D; P110H; S263I; M266Y; Y337G; H338Y; D339K; | ++++ |
| 97 | 98 | G57D; P110R; T159S; S263I; M266Y; Y337G; H338Y; D339E; | ++++ |
| 99 | 100 | G57D; P110R; S263I; M266Y; Y337G; H338Y; D339K; | ++++ |
| 101 | 102 | G57D; P110H; S263I; M266Y; Y337G; H338N; D339K; | ++++ |
| 103 | 104 | G57D; I106N; R151K; S263T; M266Y; Y337G; H338T; D339K; | ++++ |
| 105 | 106 | G57D; R151K; S263T; M266Y; Y337G; H338T; D339K; | ++++ |
| 107 | 108 | G57D; S263T; M266Y; G335T; Y337G; H338T; D339K; | ++++ |
| 109 | 110 | G57D; S263T; M266Y; G335K; Y337G; H338T; D339K; | ++++ |
| 111 | 112 | G57D; P110H; S263I; M266Y; Y337G; H338Y; D339G; | +++++ |
| 113 | 114 | D16E; G57D; P110H; S263I; M266Y; Y337G; H338Y; D339K; V346C; | +++++ |
| 115 | 116 | D16E; G57D; P110H; R151K; T159S; S263I; M266Y; G335K; Y337G; H338Y; D339K; | +++++ |
| 117 | 118 | D16E; G57D; P110H; S263I; M266Y; Y337G; H338Y; D339K; | +++++ |
| 119 | 120 | D16E; G57D; P110H; R151S; S263I; M266Y; G335K; Y337G; H338Y; D339K; | +++++ |
| 121 | 122 | D16E; G57D; P110H; R151N; T159S; S263I; M266Y; G335K; Y337G; H338Y; D339K; | +++++ |
| 123 | 124 | D16E; G57D; T61F; P110H; T159S; S201A; S263I; M266Y; G335K; Y337G; H338Y; D339K; | +++++ |
| 125 | 126 | D16E; G57D; T61F; P86G; P110H; S201A; S263I; M266Y; G335K; Y337G; H338Y; D339K; | +++++ |
| 127 | 128 | D16E; G57D; T61F; P86A; P110H; S201A; S263I; M266Y; G335K; Y337G; H338Y; D339E; | +++++ |
| 129 | 130 | D16E; G57D; P86A; P110H; S201A; S263I; M266Y; G335K; Y337G; H338Y; D339K; | +++++ |
| 131 | 132 | D16E; G57D; P86A; P110H; S201A; S263I; M266Y; G335K; Y337G; H338Y; D339K; | +++++ |
| 133 | 134 | D16E; G57D; P86A; P110H; S201A; R256H; S263I; M266Y; G335K; Y337G; H338Y; D339K; | +++++ |
| 135 | 136 | D16E; G57D; P110H; S263I; M266Y; G335K; Y337G; H338Y; D339K; | +++++ |
| 137 | 138 | D16E; G57D; P86A; P110H; S263I; M266Y; G335K; Y337G; H338Y; D339K | +++++ |
| 139 | 140 | D16E; G57D; P110H; R151K; S263I; M266Y; G335K; Y337G; H338Y; D339K; | +++++ |
| 141 | 142 | D16E; A19V; G57D; P110H; R151S; S263I; M266Y; G335R; Y337G; H338Y; D339K; | +++++ |
| 143 | 144 | D16E; G57D; P110H; R151K; T159S; S263I; M266Y; G335K; Y337G; H338Y; D339K; | +++++ |
| 145 | 146 | D16E; G57D; P110H; R151K; T159S; S263I; M266Y; G335K; Y337G; H338Y; D339E; | +++++ |
| 147 | 148 | D16E; G57D; P110H; R151K; T159S; S263I; M266Y; G335T; Y337G; H338Y; D339K; | +++++ |
| 149 | 150 | D16E; G57D; P110H; T159S; S263I; M266Y; G335K; Y337G; H338Y; D339K; | +++++ |
| 151 | 152 | D16E; G57D; P110H; T159S; S263I; M266Y; G335K; Y337G; H338Y; D339E; | +++++ |
| 153 | 154 | D16E; G57D; P110H; R151K; T159S; S263I; M266Y; G335K; Y337G; H338Y; D339K; | +++++ |
| 155 | 156 | D16E; G57D; P110H; S201A; S263I; M266Y; G335K; Y337G; H338Y; D339K; | +++++ |
| 157 | 158 | D16E; G57D; P110H; S201A; S263I; M266Y; G335K; Y337G; H338Y; D339E; | +++++ |
| 159 | 160 | D16E; G57D; T61F; P86A; P110H; S201A; S263I; M266Y; Y337G; H338Y; D339K; | +++++ |
| 161 | 162 | D16E; G57D; P110H; S201A; S263I; M266Y; Y337G; H338Y; D339K; | +++++ |
| 163 | 164 | D16E; G57D; P110H; T159S; S201A; S263I; M266Y; G335K; Y337G; H338Y; D339K; | +++++ |
| 165 | 166 | D16E; G57D; P86A; P110H; S201A; S263I; M266Y; G335K; Y337G; H338Y; D339E; | +++++ |
| 167 | 168 | D16E; G57D; P86A; P110H; T159S; S201A; S263I; M266Y; Y337G; H338Y; D339K; | +++++ |
| 169 | 170 | D16E; G57D; P110H; S263I; M266Y; G335K; Y337G; H338Y; D339E; | +++++ |
| 171 | 172 | D16E; G57D; P110H; S201A; S263I; M266Y; G335R; Y337G; H338Y; D339K; | +++++ |
| 173 | 174 | D16E; G57D; P86G; P110H; T159S; S263I; M266Y; G335R; Y337G; H338Y; D339K; | +++++ |
| 175 | 176 | D16E; G57D; P86A; P110H; R151S; T159S; R256H; S263I; M266Y; G335K; Y337G; H338Y; D339K; | ++++++ |
| 177 | 178 | D16E; G57D; P86A; P110H; R151S; S201A; S263I; M266Y; G335K; Y337G; H338Y; D339K; | ++++++ |
| 179 | 180 | D16E; G57D; P110H; R151S; S201A; R256H; S263I; M266Y; G335K; Y337G; H338Y; D339K; | ++++++ |
| 181 | 182 | D16E; G57D; P86A; P110H; R151S; T159S; S201A; R256H; S263I; M266Y; G335K; Y337G; H338Y; D339K; | ++++++ |
| 183 | 184 | D16E; G57D; P110H; R151S; S201A; S263I; M266Y; G335K; Y337G; H338Y; D339K; | ++++++ |

TABLE 2

| Activity or Stereoselectivity | Description | Reaction condition |
|---|---|---|
| + | Conversion of substrate A1 ≥ 50%, de for A2 in products 60%, reaction time ≤ 24 hours | Loading of enzyme powder 5 g/L, loading of substrate A1 30 g/L, loading of glycine 123 g/L, 50 μM PLP, 10%(v/v) DMSO, 30° C. |
| ++ | Conversion of substrate A1 ≥ 65%, de for A2 in products 70%, reaction time ≤ 24 hours | Loading of enzyme powder 3 g/L, loading of substrate A1 30 g/L, loading of glycine 123 g/L, 50 μM PLP, 20%(v/v) DMSO, 30° C. |
| +++ | Conversion of substrate A1 ≥ 65%, de for A2 in products 80%, reaction time ≤ 24 hours | Loading of enzyme powder 3 g/L, loading of substrate A1 30 g/L, loading of glycine 123 g/L, 50 μM PLP, 30%(v/v) Methanol, 30° C. |
| ++++ | Conversion of substrate A1 ≥ 65%, de for A2 in products 85%, reaction time ≤ 10 hours | Loading of enzyme powder 3 g/L, loading of substrate A1 30 g/L, loading of glycine 123 g/L, 50 μM PLP, 30%(v/v) Methanol, 30° C. |
| +++++ | Conversion of substrate A1 ≥ 65%, de for A2 in products 90%, reaction time ≤ 8 hours | Loading of enzyme powder 3 g/L, loading of substrate A1 30 g/L, loading of glycine 123 g/L, 50 μM PLP, 30%(v/v) Methanol, 35° C. |
| ++++++ | Conversion of substrate A1 ≥ 65%, de for A2 in products 95%, reaction time ≤ 6 hours | Loading of enzyme powder 1 g/L, loading of substrate A1 30 g/L, loading of glycine 123 g/L, 50 μM PLP, 40%(v/v) Methanol, 40° C. |

The amino acid sequences listed in Table 1 (i.e., even sequence identifiers of SEQ ID NO: 4 to 184) each has insertion of 19 amino acid residues compared to SEQ ID No: 2. Compared to SEQ ID No: 2, SEQ ID NO: 186, 188, 190, 192, 194, 196, 198, 200, 202, 204, 206, 208, 210, 212, 214, 216 each has insertion, deletion or substitution of a different number of amino acid residues. The engineered aldolase polypeptides represented by SEQ ID NO: 186, 188, 190, 192, 194, 196, 198, 200, 202, 204, 206, 208, 210, 212, 214, 216 exhibit higher stereoselectivity than that of SEQ ID No: 2 under the reaction conditions of +, ++, +++, ++++, +++++ or ++++++ as shown in Table 2.

3. Polynucleotides, Control Sequences, Expression Vectors and Host Cells that can be Used to Produce Engineered Aldolase Polypeptides In another aspect, this disclosure provides polynucleotides encoding engineered polypeptides having aldolase activity described herein. The polynucleotides can be linked to one or more heterologous regulatory sequences that control gene expression to produce recombinant polynucleotides that are capable of expressing the engineered polypeptides. Expression constructs comprising a heterologous polynucleotide encoding an engineered aldolase may be introduced into a suitable host cell to express the corresponding engineered aldolase polypeptide.

As apparent to one skilled in the art, the availability of protein sequences and knowledge of codons corresponding to a variety of amino acids provide an illustration of all possible polynucleotides that encode the protein sequence of interest. The degeneracy of the genetic code, in which the same amino acid is encoded by selectable or synonymous codons, allows for the production of an extremely large number of polynucleotides, all of which encode the engineered aldolase polypeptides disclosed herein. Thus, upon determination of a particular amino acid sequence, one skilled in the art can generate any number of different polynucleotides by merely modifying one or more codons in a manner that does not alter the amino acid sequence of the protein. In this regard, this disclosure specifically contemplates each and every possible alteration of a polynucleotide that can be made by selecting a combination based on possible codon selections, for any of the polypeptides disclosed herein, comprising those amino acid sequences of exemplary engineered polypeptides listed in Table 1, and any of the polypeptides disclosed as even sequence identifiers of SEQ ID NOS: 4 to 216 in the Sequence Listing incorporated by reference, all of which are believed to be particularly public.

In various embodiments, the codons are preferably selected to accommodate the host cell in which the recombinant protein is produced. For example, codons preferred for bacteria are used to express genes in bacteria; codons preferred for yeast are used to express genes in yeast; and codons preferred for mammals are used for gene expression in mammalian cells.

In some embodiments, the polynucleotides encode polypeptides comprising amino acid sequences that are at least about 80%, 85%, 86%, 87%, 88%, 89%, 90%, 91%, 92%, 93%, 94%, 95%, 96%, 97%, 98%, 99% or more identical to a reference sequence that is an even sequence identifier of SEQ ID NO: 4-216. Wherein the polypeptides have aldolase activity and one or more of the improved properties described herein, for example, the ability to convert compound A1 to compound A2 with increased stereoselectivity compared to the polypeptide of SEQ ID NO: 2.

In some embodiments, the polynucleotides encode engineered aldolase polypeptides comprising amino acid sequences having a percentage of identity described above and having one or more amino acid residue differences as compared to SEQ ID NO: 4. In some embodiments, the present disclosure provides engineered polypeptides having aldolase activity, wherein the engineered polypeptide has at least 80% sequence identity to the reference sequence of SEQ ID NO: 4 and comprises a combination of residue difference that is selected from the following positions: X16, X18, X19, X37, X38, X41, X42, X43, X57, X61, X86, X106, X110, X130, X151, X152, X159, X198, X201, X249, X256, X263, X266, X310, X327, X335, X337, X338, X339, X346.

In some embodiments, the polynucleotides encoding the engineered aldolase polypeptides comprise sequences having odd sequence identifier of SEQ ID NO: 3-215.

In some embodiments, the polynucleotides encode polypeptides as described herein; but at the nucleotide level, the polynucleotides have about 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to reference polynucleotides encoding engineered aldolase polypeptides as described herein. In some embodiments, the reference polynucleotides are selected from the sequences having the odd sequence identifiers of SEQ ID NOs: 3-215.

The isolated polynucleotides encoding engineered aldolase polypeptides can be manipulated to enable the expression of the engineered polypeptides in a variety of ways, which comprises further modification of the sequences by codon optimization to improve expression, insertion into suitable expression elements with or without additional control sequences, and transformation into a host cell suitable for expression and production of the engineered polypeptides.

Depending on the expression vector, manipulation of the isolated polynucleotide prior to insertion of the isolated polynucleotide into the vector may be desirable or necessary. Techniques for modifying polynucleotides and nucleic acid sequences using recombinant DNA methods are well known in the art. Guidance is provided below: Sambrook et al., 2001, Molecular Cloning: A Laboratory Manual, Third Edition, Cold Spring Harbor Laboratory Press; and Current Protocols in Molecular Biology, Ausubel. F. Eds., Greene Pub. Associates, 1998, 2010 Year update.

In another aspect, this disclosure also relates to recombinant expression vectors, depending on the type of host they are to be introduced into, including a polynucleotide encoding an engineered aldolase polypeptide or variant thereof, and one or more expression regulatory regions, such as promoters and terminators, origin of replication and the like. Alternatively, the nucleic acid sequence of the present disclosure can be expressed by inserting the nucleic acid sequence or the nucleic acid construct comprising the sequence into an appropriate expression vector. In generating the expression vector, the coding sequence is located in the vector such that the coding sequence is linked to a suitable control sequence for expression.

The recombinant expression vector can be any vector (e.g., a plasmid or virus) that can be conveniently used in recombinant DNA procedures and can result in the expression of a polynucleotide sequence. The choice of vector will generally depend on the compatibility of the vector with the host cell to be introduced into. The vector can be linear or closed circular plasmid. The expression vector may be an autonomously replicating vector, i.e., a vector that exists as an extrachromosomal entity whose replication is independent of chromosomal replication such as plasmids, extrachromosomal elements, minichromosomes, or artificial chromosomes. The vector may contain any tools for ensuring self-copying. Alternatively, the vector may be a vector that, when introduced into a host cell, integrates into the genome and replicates with the chromosome into which it is integrated. Moreover, a single vector or plasmid or two or more vectors or plasmids that together comprise the total DNA to be introduced into the genome of the host cell may be used. Many expression vectors useful to the embodiments of the present disclosure are commercially available. An exemplary expression vector can be prepared by inserting a polynucleotide encoding an engineered aldolase polypeptide to plasmid pACYC-Duet-1 (Novagen).

In another aspect, this disclosure provides host cells comprising polynucleotides encoding engineered aldolase polypeptides of the present disclosure. The polynucleotide is linked to one or more control sequences for expression of aldolase polypeptides in a host cell. Host cells for expression of polypeptides encoded by the expression vectors of the present disclosure are well known in the art, including, but not limited to, bacterial cells such as *E. coli*, *Streptomyces*, and *Salmonella typhimurium*; fungals (e.g., *Saccharomyces cerevisiae* or *Pichia pastoris*); insect cells such as *Drosophila* S2 and *Spodoptera* Sf9; animal cells such as CHO, COS, BHK, 293 and Bowes melanoma cells; and plant cells. An exemplary host cell is *E. coli* BL21 (DE3). The above host cells may be wild-type or may be engineered cells through genomic edition, such as knockout of the wild-type aldolase gene carried in the host cell's genome. Suitable media and growth conditions for the above host cells are well known in the art.

Polynucleotides used to express engineered aldolases can be introduced into cells by a variety of methods known in the art. Techniques comprise, among others, electroporation, bio-particle bombardment, liposome-mediated transfection, calcium chloride transfection, and protoplast fusion. Different methods of introducing polynucleotides into cells are obvious to those skilled in the art.

4. Process of Producing an Engineered Aldolase Polypeptide

Engineered aldolase can be obtained by subjecting a polynucleotide encoding an aldolase to mutagenesis and/or directed evolution. An exemplary directional evolution technique can be found in "Biocatalysis for the Pharmaceutical Industry: Discovery, Development, and Manufacturing" (2009 John Wiley & Sons Asia (Pte) Ltd. ISBN: 978-0-470-82314-9).

When the sequence of an engineered polypeptide is known, the encoding polynucleotide may be prepared by standard solid-phase methods according to known synthetic methods. In some embodiments, fragments of up to about 100 bases can be synthesized separately and then ligated (e.g., by enzymatic or chemical ligation methods or polymerase-mediated methods) to form any desired contiguous sequence. For example, the polynucleotides and oligonucleotides of the present disclosure can be prepared by chemical synthesis using, for example, the classic phosphoramidite methods described by Beaucage et al., 1981, Tet Lett 22: 1859-69, or Matthes et al. People, 1984, EMBO J. 3: 801-05, as typically practiced in automated synthesis methods. According to the phosphoramidite method, oligonucleotides are synthesized, purified, annealed, ligated, and cloned into a suitable vector, for example, in an automated DNA synthesizer. In addition, essentially any nucleic acid is available from any of a variety of commercial sources.

In some embodiments, the present disclosure also provides a process for preparing or producing an engineered aldolase polypeptide that is capable of converting Compound A1 to Compound A2 under suitable reaction conditions, wherein the process comprises culturing a host cell capable of expressing a polynucleotide encoding an engineered polypeptide under culture conditions suitable for the expression of the polypeptide. In some embodiments, the process of preparing a polypeptide further comprises isolating the polypeptide. Engineered polypeptides may be expressed in suitable cells and isolated (or recovered) from the host cell and/or culture medium using any one or more of the well-known techniques for protein purification, the techniques for protein purification include, among others, lysozyme treatment, sonication, filtration, salting out, ultra-centrifugation and chromatography.

5. Methods of Using an Engineered Aldolase and Compounds Prepared Therewith

In another aspect, the engineered aldolase polypeptides described herein can asymmetrically condense aldehyde substrates and amino acid substrates. The present disclosure also provides process of preparing a wide range of compounds (I) or structural analogs thereof using an engineered aldolase polypeptide disclosed herein. In some embodiments, engineered aldolase polypeptides can be used in a process of preparing a compound of structural formula (I):

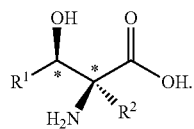

(I)

the β-hydroxy-α-amino acid product of formula (I) has the indicated stereochemical configuration at the chiral center marked with an *; the β-hydroxy-α-amino acid product of formula (I) is in diastereomeric excess over the other isomers, where $R^1$ is optionally substituted or unsubstituted aryl or heteroaryl, or optionally substituted or unsubstituted $C_1$-$C_8$ alkyl; $R^2$ is —H, —$CH_2OH$, —$CH_2SH$, —$CH_2SCH_3$, or optionally substituted or unsubstituted $C_1$-$C_4$ hydrocarbyl. The process herein comprises that, under reaction conditions suitable for converting the aldehyde substrate and the amino acid substrate to β-hydroxy-α-amino acid product, the aldehyde substrate of formula (II) and the amino acid substrate of formula (III)

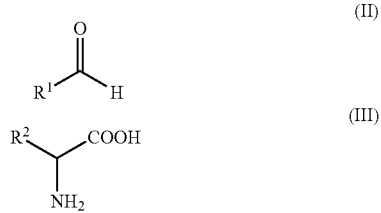

are contacted with an aldolase polypeptide, wherein the aldolase polypeptide is an engineered aldolase polypeptide described herein. In some embodiments, the engineered aldolase polypeptides have at least 80%, 85%, 86%, 87%, 88%, 89%, 90%, 91%, 92%, 93%, 94%, 95%, 96%, 97%, 98%, 99% or more of sequence identity with SEQ ID NO:4, and are capable of condensing the aldehyde substrate of formula (II) and the amino acid substrate of formula (III) to form β-Hydroxy-α-amino acid product of formula (I) with a higher conversion and/or higher stereoselectivity than SEQ ID NO: 2.

In some embodiments, the β-hydroxy-α-amino acid product of formula (I) is present in a diastereomeric excess of at least 60%, 65%, 70%, 75%, 80%, 85%, 90%, 91%, 92%, 93%, 94%, 95%, 96%, 97%, 98%, or 99% or greater.

As noted above, aldolase polypeptides useful in the process of the present disclosure may be characterized according to the ability of condensation of 4-(methylsulfonyl)benzaldehyde and glycine to (2S,3R)-2-amino-3-hydroxy-3-[4-(methylsulfonyl)phenyl] propanoic acid. Thus, in any of the embodiments of the process disclosed herein, the process may be carried out, wherein the aldolase polypeptides are capable of condensing 4-(methylsulfonyl)benzaldehyde and glycine to (2S,3R)-2-amino-3-hydroxy-3-[4-(methylsulfonyl)phenyl] propanoic acid with a higher conversion and/or higher stereoselectivity than SEQ ID NO: 2, and have at least 80%, 85%, 86%, 87%, 88%, 89%, 90%, 91%, 92%, 93%, 94%, 95%, 96%, 97%, 98%, 99% or more of sequence identity with SEQ ID NO:4.

In some embodiments of the above process, $R^1$ is optionally substituted or unsubstituted $C_1$-$C_8$ alkyl.

In some embodiments, $R^1$ is optionally substituted or unsubstituted phenyl. In some embodiments, $R^1$ is optionally substituted or unsubstituted pyridyl. In some embodiments, $R^1$ is optionally substituted or unsubstituted aryl or heteroaryl. In some embodiments, $R^1$ is optionally substituted or unsubstituted phenyl, and substitution occurs at either (ortho, meta or para) of the phenyl ring or any two of the substitutions occurring simultaneously on the phenyl ring, the substituents are selected from the group consisting of $C_1$-$C_4$ hydrocarbyl, halogen (e.g., —F, —Cl, —Br and —I), —$NO_2$, —NO, —$SO_2R'$ or —SOR', —SR', —NR'R', —OR', —$CO_2R'$ or —COR', —C(O)NR', —$SO_2NH_2$ or —$SONH_2$, —CN, $CF_3$, wherein each R' is independently selected from —H or ($C_1$-$C_4$) alkyl. In some embodiments, ($C_1$-$C_4$) alkyl is a halogen-substituted hydrocarbon.

In some embodiments of the above process, $R^2$ is —H, —$CH_3$, —$CH_2CH_3$, —$CH(CH_3)_2$, —$CH_2OH$, —$CH_2SH$, or —$CH_2SCH_3$.

In some embodiments, the β-hydroxy-α-amino acid product of formula (I) is present in a diastereomeric excess of at least 60%, 65%, 70%, 75%, 80%, 85%, 90%, 91%, 92%, 93%, 94%, 95%, 96%, 97%, 98%, 99% or greater.

In some embodiments of this process, the β-hydroxy-α-amino acid product of formula (I) is (2S,3R)-(+)-2-amino-3-hydroxy-2,4-methylpentanoic acid:

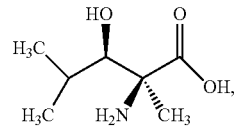

and the amino acid substrate of formula (III) is L-alanine, the aldehyde substrate of formula (II) is isobutyraldehyde:

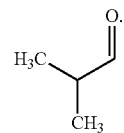

In some embodiments of this process, the β-hydroxy-α-amino acid product of formula (I) is (2S,3R)-(+)-2-amino-3-hydroxy-4-methylpentanoic acid:

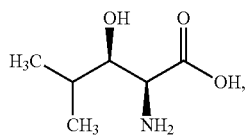

and the amino acid substrate of formula (III) is glycine, the aldehyde substrate of formula (II) is isobutyraldehyde:

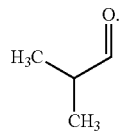

In some embodiments of this process, the β-hydroxy-α-amino acid product of formula (I) is (2S,3R)-2-amino-3-hydroxydecanoic acid:

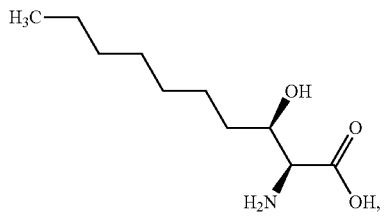

and the amino acid substrate of formula (III) is glycine, the aldehyde substrate of formula (II) is n-octanal:

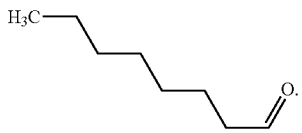

In some embodiments of this process, the β-hydroxy-α-amino acid product of formula (I) is (2S,3R, 4E)-2-amino-3-hydroxy-4-hexenoic acid:

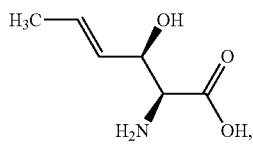

and the amino acid substrate of formula (III) is glycine, the aldehyde substrate of formula (II) is crotonaldehyde:

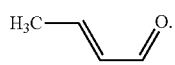

In some embodiments of this process, the β-hydroxy-α-amino acid product of formula (I) is (2S,3S)-2-amino-3-[(4S) 3-dioxolan-4-yl]-3-hydroxypropanoic acid:

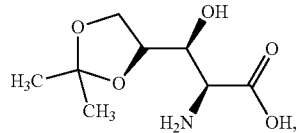

and the amino acid substrate of formula (III) is glycine, the aldehyde substrate of formula (II) is (4S)-2,2-di methyl-1,3-dioxolane-4-carbaldehyde:

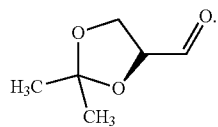

In some embodiments of this process, the β-hydroxy-α-amino acid product of formula (I) is (2S,3S)-2-amino-3-hydroxy-3-(1H-imidazol-2-yl) propanoic acid:

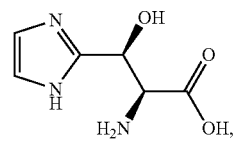

and the amino acid substrate of formula (III) is glycine, the aldehyde substrate of formula (II) is 1H-imidazole-2-carboxaldehyde:

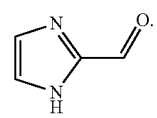

In some embodiments of this process, the β-hydroxy-α-amino acid product of formula (I) is (2S,3R)-2-amino-3-hydroxy-3-(pyridin-3-yl) propanoic acid:

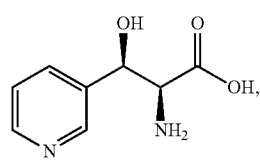 [SMILES: N[C@H](C(=O)O)[C@H](O)c1cccnc1]

and the amino acid substrate of formula (III) is glycine, the aldehyde substrate of formula (II) is pyridine carboxaldehyde:

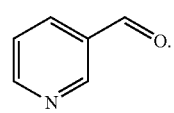

In some embodiments of this process, the β-hydroxy-α-amino acid product of formula (I) is (2S,3R)-2-amino-3-hydroxy-5-phenylpentanoic acid:

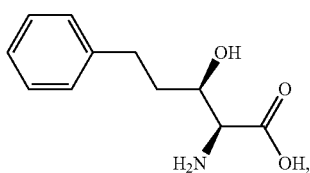 [SMILES: N[C@H](C(=O)O)[C@H](O)CCc1ccccc1]

and the amino acid substrate of formula (III) is glycine, the aldehyde substrate of formula (II) is 3-phenylpropionaldehyde:

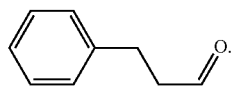

In some embodiments of this process, the β-hydroxy-α-amino acid product of formula (I) is (2S,3R)-2-amino-5-(benzyloxy)-3-hydroxyvaleric acid:

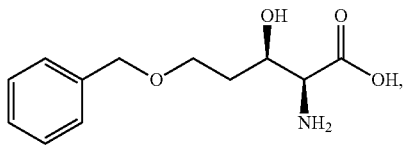 [SMILES: N[C@H](C(=O)O)[C@H](O)CCOCc1ccccc1]

and the amino acid substrate of formula (III) is glycine, the aldehyde substrate of formula (II) is 3-(benzyloxy) propanal:

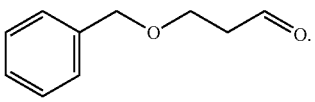 [SMILES: O=CCCOCc1ccccc1]

In some embodiments of this process, the β-hydroxy-α-amino acid product of formula (I) is (2S,3R)-2-amino-3-(1,3-1,3-benzodioxol-5-yl)-3-hydroxypropanoic acid:

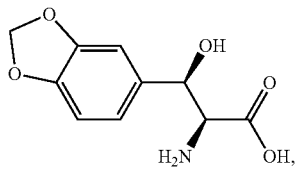 [SMILES: N[C@H](C(=O)O)[C@H](O)c1ccc2c(c1)OCO2]

and the amino acid substrate of formula (III) is glycine, the aldehyde substrate of formula (II) is methylenedioxybenzene-5-carbaldehyde:

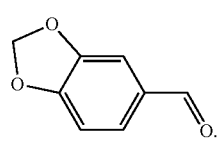 [SMILES: O=Cc1ccc2c(c1)OCO2]

In some embodiments of this process, the β-hydroxy-α-amino acid product of formula (I) is (2S,3R)-2-amino-4-(2-amino-6-hydroxy-9H-purin-9-Yl)-3-hydroxybutyrate:

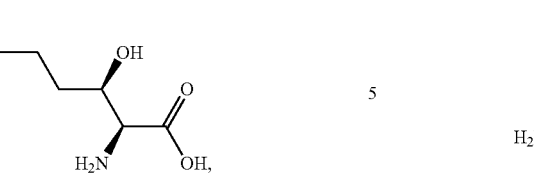

and the amino acid substrate of formula (III) is glycine, the aldehyde substrate of formula (II) is (2-amino-6-hydroxy-9H-purin-9-yl) acetaldehyde:

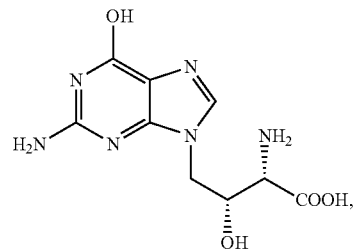 [SMILES: Nc1nc(O)c2ncn(C[C@@H](O)[C@H](N)C(=O)O)c2n1]

In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments, the β-hydroxy-α-amino acid product of structural formula (I) is:

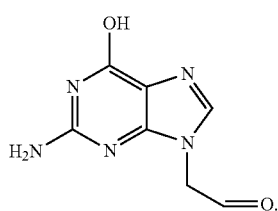

Wherein $R^3$ is $C_1$-$C_4$ hydrocarbyl, —H, halogen (such as —F, —Cl, —Br and —I), —NO$_2$, —NO, —SO$_2$R' or —SOR', —SR', —NR'R', —OR', —CO$_2$R' or —COR', —C(O)NR', —SO$_2$NH$_2$ or —SONH$_2$, —CN, CF$_3$, wherein each R' is independently selected from —H or ($C_1$-$C_4$) hydrocarbyl; $R^3$ may also be

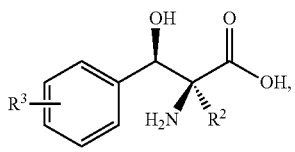

$R^2$ is —H, —CH$_3$, —CH$_2$CH$_3$, —CH(CH$_3$)$_2$, —CH$_2$OH, —CH$_2$SH or —CH$_2$SCH$_3$, the aldehyde substrate of formula (II) is:

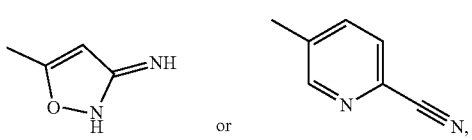

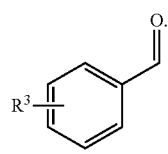

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring. In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98% or 99% or more.

In some embodiments of this process, the β-hydroxy-α-amino acid product of formula (I) is:

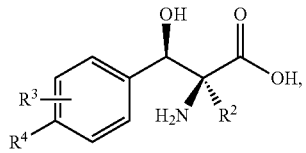

Wherein $R^4$ is $R^3$ as defined above, $R^3$ and $R^2$ are as defined above, the aldehyde substrate of formula (II) is:

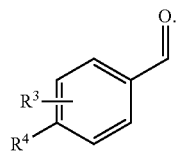

In some embodiments, $R^3$ is in the meta position of the phenyl ring. In some embodiments, $R^3$ is ortho to the phenyl ring. In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments of this process, the β-hydroxy-α-amino acid product of formula (I) is (2S,3R)-2-amino-3-hydroxy-3-benzoic acid:

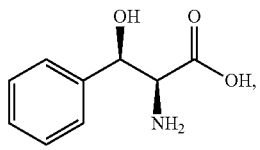 [SMILES: N[C@H](C(=O)O)[C@H](O)c1ccccc1]

and the amino acid substrate of formula (III) is glycine, the aldehyde substrate of formula (II) is benzaldehyde:

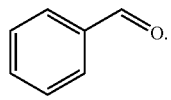

In some embodiments of this process, the β-hydroxy-α-amino acid product of formula (I) is (2S,3R)-2-amino-3-hydroxy-3-(4-methylphenyl) propanoic acid

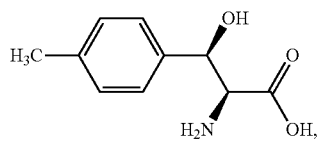

and the amino acid substrate of formula (III) is glycine, the aldehyde substrate of formula (II) is 4-methyl benzaldehyde:

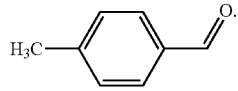

In some embodiments of this process, the β-hydroxy-α-amino acid product of structural formula (I) is (2S,3R)-2-amino-3-(2-chlorophenyl)-3-hydroxypropanoic acid:

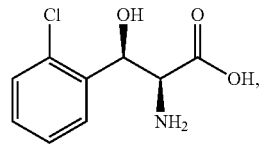 [SMILES: N[C@H](C(=O)O)[C@H](O)c1ccccc1Cl]

and the amino acid substrate of formula (III) is glycine, the aldehyde substrate of formula (II) is 2-chlorobenzaldehyde:

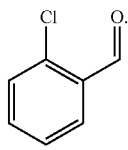

In some embodiments of this process, the β-hydroxy-α-amino acid product of formula (I) is (2S,3R)-2-amino-3-(3,4-dihydroxybenzene)-3-hydroxypropanoic acid:

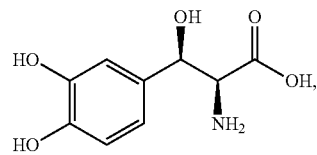 [SMILES: N[C@H](C(=O)O)[C@H](O)c1ccc(O)c(O)c1]

and the amino acid substrate of formula (III) is glycine and the aldehyde substrate of formula (II) is 3,4-dihydroxybenzaldehyde:

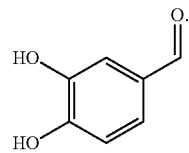

In some embodiments of this process, the β-hydroxy-α-amino acid product of formula (I) is (2S,3R)-2-amino-3-hydroxy-3-(4-hydroxyphenyl) propanoic acid:

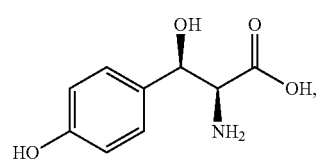

and the amino acid substrate of formula (III) is glycine, the aldehyde substrate of formula (II) is 4-hydroxybenzaldehyde:

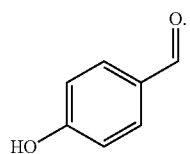

In some embodiments of this process, the β-hydroxy-α-amino acid product of formula (I) is (2S,3R)-2-amino-3-hydroxy-3-(3-nitrophenyl) propanoic acid:

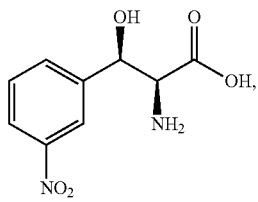 [SMILES: N[C@H](C(=O)O)[C@H](O)c1cccc([N+](=O)[O-])c1]

and the amino acid substrate of formula (III) is glycine, the aldehyde substrate of formula (II) is 3-nitrobenzaldehyde:

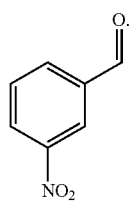

In some embodiments of this process, the β-hydroxy-α-amino acid product of formula (I) is (2S,3R)-2-amino-3-(4-fluoro-3-nitrophenyl)-3-hydroxypropanoic acid:

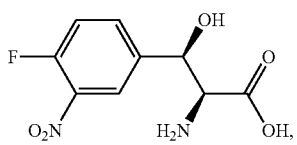

and the amino acid substrate of formula (III) is glycine and the aldehyde substrate of formula (II) is 4-fluoro-3-nitrobenzaldehyde:

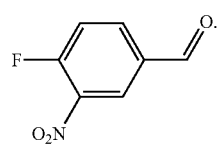

In some embodiments of this process, the β-hydroxy-α-amino acid product of formula (I) is (2S,3R)-2-amino-3-hydroxy-2-methyl-3-(3-nitrophenyl) propanoic acid:

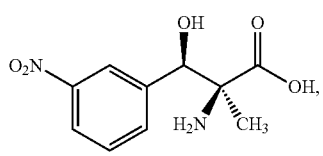 [SMILES: C[C@@](N)(C(=O)O)[C@H](O)c1cccc([N+](=O)[O-])c1]

and the amino acid substrate of formula (III) is L-alanine, the aldehyde substrate of formula (II) is 3-nitrobenzaldehyde:

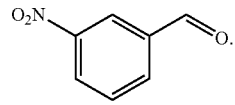 [SMILES: O=Cc1cccc([N+](=O)[O-])c1]

In some embodiments of this process, the β-hydroxy-α-amino acid product of formula (I) is (2S,3R)-2-amino-3-hydroxy-3-(2-nitrophenyl) propanoic acid:

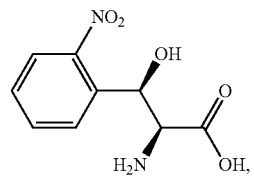 [SMILES: N[C@H](C(=O)O)[C@H](O)c1ccccc1[N+](=O)[O-]]

and the amino acid substrate of formula (III) is glycine, the aldehyde substrate of formula (II) is 2-nitrobenzaldehyde:

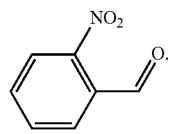 [SMILES: O=Cc1ccccc1[N+](=O)[O-]]

In some embodiments of this process, the β-hydroxy-α-amino acid product of formula (I) is (2S,3R)-2-amino-3-hydroxy-3-(4-nitrophenyl) propanoic acid:

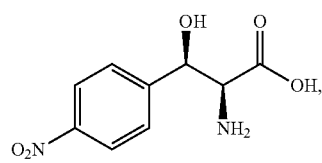 [SMILES: N[C@H](C(=O)O)[C@H](O)c1ccc([N+](=O)[O-])cc1]

and the amino acid substrate of formula (III) is glycine, the aldehyde substrate of formula (II) is 4-nitrobenzaldehyde

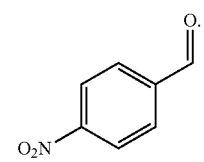 [SMILES: O=Cc1ccc([N+](=O)[O-])cc1]

In some embodiments of this process, the β-hydroxy-α-amino acid product of formula (I) is (2S,3R)-2-amino-3-hydroxy-3-(4-mercaptophenyl) propanoic acid:

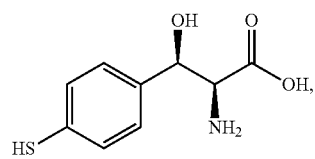

and the amino acid substrate of formula (III) is glycine, the aldehyde substrate of formula (II) is 4-mercaptobenzaldehyde:

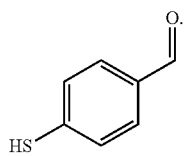

In some embodiments of this process, the β-hydroxy-α-amino acid product of formula (I) is (2S,3R)-2-amino-3-hydroxy-3-(4-mercaptomethylbenzene) propanoic acid:

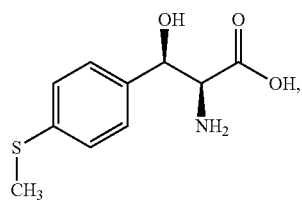

and the amino acid substrate of formula (III) is glycine, the aldehyde substrate of formula (II) is 4-mercaptomethylbenzaldehyde:

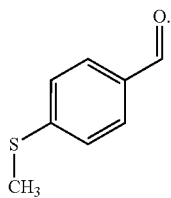

In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments, the improved engineered aldolase polypeptide can be used in the preparation of a diastereomeric excess of the compound of formula A2 (2S,3R)-2-amino-3-hydroxy-3-[4-(methylsulfonyl)phenyl] propanoic acid:

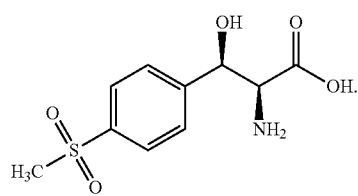

In these embodiments, the process comprises that, in a suitable organic solvent, in the presence of glycine, under reaction conditions suitable for converting the compound of formula A1 to a compound of formula A2, the compound of formula A1 is contacted with the engineered aldolase polypeptides disclosed herein:

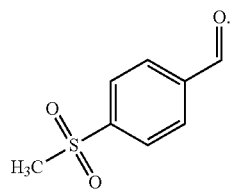

In some embodiments of the above process, the compound of Formula (I) or the compound of Formula A2 is present in a diastereomeric excess of at least 60%, 65%, 70%, 75%, 80%, 85%, 90%, 91%, 92%, 93% 94%, 95%, 96%, 97%, 98%, or 99% or greater.

Engineered aldolase polypeptides that can be used in the above process comprise amino acid sequences selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216.

As described herein and exemplified in the examples, the present disclosure contemplates a range of suitable reaction conditions that may be used in the process herein, including but not limited to pH, temperature, buffers, solvent systems, substrate loadings, mixtures of product diastereomers, polypeptide loading, cofactor loading, pressure, and reaction time. Additional suitable reaction conditions for performing a method of enzymatically converting substrate compounds to a product compound using engineered aldolase polypeptides described herein can be readily optimized by routine experimentation, which including but not limited to that the engineered aldolase polypeptide is contacted with substrate compounds under experimental reaction conditions of varying concentration, pH, temperature, solvent conditions, and the product compound is detected, for example, using the methods described in the Examples provided herein.

As described above, engineered polypeptides having aldolase activity for use in the process of the present disclosure generally comprises amino acid sequences that have at least 80%, 85%, 86%, 87%, 88%, 89%, 90%, 91%, 92%, 93%, 94%, 95%, 96%, 97%, 98% or 99% sequence identity to the reference amino acid sequence selected from any one of the even numbered sequences of SEQ ID NO: 4 to 216.

The substrate compounds in the reaction mixture can be varied, taking into consideration of, for example, the amount of the desired product compound, the effect of the substrate concentration on the enzyme activity, the stability of the enzyme under the reaction conditions, and the percent conversion of substrate to product. In some embodiments of the process, the suitable reaction conditions include at least about 0.5 to about 200 g/L, about 1 to about 200 g/L, about 5 to about 200 g/L, about 10 to about 200 g/L, or about 50 to about 200 g/L of loading of substrate (II) or substrate A1. In some embodiments, suitable reaction conditions include at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L or even more of loading of substrate (II) or substrate A1. The values for the substrate loading provided herein are based on the molecular weight of compound (II) or A1, however it is also contemplated that the equivalent molar amounts of various hydrates and salts of compound (II) or A1 may also be used in the process.

In the process described herein, the engineered aldolase polypeptides use an amino acid and an aldehyde compound to form a product compound. In some embodiments, the amino acids in the reaction conditions include compounds selected from glycine, D,L-alanine, D,L-serine, D,L-cysteine, D,L-leucine, D,L-isoleucine, D,L-methionine, D,L-threonine or D,L-valine. In some embodiments, the amino acid is glycine. In some embodiments, suitable reaction conditions include amino acids present in a loading of at least about 1 times of the molar loading of substrate (II). In some embodiments, glycine is present at a loading of 5, 6, 7, 8, 9 or 10 times of the molar loading of substrate (II).

Suitable reaction conditions for the process generally also include the presence of a cofactor in the reaction mixture. Because the engineered aldolases typically use members of the vitamin B6 family, the reaction conditions may include one or more compounds selected from pyridoxal-5'-phosphate (also known as pyridoxal-phosphate, PLP, P5P), pyridoxine (PN), Pyridoxal (PL), pyridoxamine (PM), and their phosphorylated counterparts; pyridoxine phosphate (PNP), and pyridoxamine phosphate (PMP). In some embodiments, suitable reaction conditions may include a cofactor selected from the group consisting of PLP, PN, PL, PM, PNP and PMP, at a concentration of about 0.1 g/L to about 10 g/L, about 0.2 g/L to about 5 g/L, about 0.5 g/L to about 2.5 g/L. In some embodiments, the cofactor is PLP. Accordingly, in some embodiments, suitable reaction conditions may include cofactor PLP at a concentration of about 0.1 g/L to about 10 g/L, about 0.2 g/L to about 5 g/L, about 0.5 g/L to about 2.5 g/L. In some embodiments, the reaction conditions include about 10 g/L or less, about 5 g/L or less, about 2.5 g/L or less, about 1.0 g/L or less, about 0.5 g/L or Less, or a PLP concentration of about 0.2 g/L or less.

In some embodiments of the process (e.g., where whole cells or lysates are used), the cofactor is present naturally in the cell extract and does not need to be supplemented. In some embodiments of the process (e.g., using partially purified, or purified aldolase), the process may further include the step of adding cofactor to the enzymatic reaction mixture. In some embodiments, cofactor is added either at the beginning of the reaction and/or additional cofactor is added during the reaction.

In the embodiments of the reaction, the reaction conditions may include a suitable pH. As noted above, the desired pH or desired pH range can be maintained by using an acid or base, a suitable buffer, or a combination of buffer and added acid or base. The pH of the reaction mixture can be controlled before and/or during the reaction. In some embodiments, suitable reaction conditions include a solution pH of about 4 to about 8, a pH of about 5 to about 7, a pH of about 6 to about 7. In some embodiments, the reaction conditions include a solution pH of about 4, 4.5, 5, 5.5, 6, 6.5, 7, 7.5 or 8.

In embodiments of the processes herein, suitable temperatures can be used for the reaction conditions, taking into consideration of, for example, the increase in reaction rate at higher temperatures, the activity of the enzyme for sufficient duration of the reaction. Accordingly, in some embodiments, suitable reaction conditions include a temperature of about 10° C. to about 60° C., about 25° C. to about 50° C., about 25° C. to about 40° C., or about 25° C. to about 30° C. In some embodiments, suitable reaction temperatures include a temperature of about 25° C., 30° C., 35° C., 40° C., 45° C., 50° C., 55° C., or 60° C. In some embodiments, the temperature during the enzymatic reaction can be maintained at a certain temperature throughout the reaction. In some embodiments, the temperature during the enzymatic reaction may be adjusted over a temperature profile during the course of the reaction.

The processes of using the engineered aldolases are generally carried out in a solvent. Suitable solvents include water, aqueous buffer solutions, organic solvents, and/or co-solvent systems, which generally include aqueous solvents and organic solvents. The aqueous solutions (water or aqueous co-solvent systems) can be pH-buffered or unbuffered. In some embodiments, the processes of using an engineered aldolase polypeptide are generally carried out in an aqueous co-solvent system comprising an organic solvent (e.g., methanol, ethanol, propanol, isopropanol (IPA), dimethyl sulfoxide (DMSO), dimethylformamide (DMF), isopropyl acetate, ethyl acetate, butyl acetate, 1-octanol, heptane, octane, methyl tert-butyl ether (MTBE), Toluene, etc.), ionic liquids (for example, 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of the aqueous co-solvent system may be miscible with the aqueous component, providing a single liquid phase, or may be partially miscible or immiscible with the aqueous component, providing two liquid phases. Exemplary aqueous co-solvent system comprises water and one or more organic solvents. In general, the organic solvent component of the aqueous co-solvent system is selected such that it does not completely inactivate the aldolase. Suitable co-solvent system can be readily identified by measuring the enzymatic activity of a particular engineered aldolase with a defined substrate of interest in the candidate solvent system, utilizing enzymatic activity assays, such as those described herein. In some embodiments of the process, suitable reaction conditions include an aqueous co-solvent comprising ethanol at a concentration of about 1% to about 60% (v/v), about 1% to about 40% (v/v), about 2% to about 40% (v/v), about 5% to about 40% (v/v), from about 10% to about 40% (v/v), from about 10% to about 30% (v/v), or about 10% to about 20% (v/v). In some embodiments of the process, suitable reaction conditions include an aqueous co-solvent comprising ethanol at a concentration of at least about 1%, 5%, 10%, 15%, 20%, 25%, 30%, 35%, 40%, 45%, 50%, 55%, or 60% (v/v).

Suitable reaction conditions can include a combination of reaction parameters that provide for the biocatalytic conversion of the substrate compounds to its corresponding product compound. Accordingly, in some embodiments of the process, the combination of reaction parameters comprises: (a) substrate A1 loading of about 10 g/L to about 200 g/L; (b) glycine loading is about 5 to 10 times the molar amount of substrate A1; (c) engineered polypeptide concentration of about 0.5 g/L to 10 g/L; (d) PLP cofactor concentration of about 0.1 mM to 10 mM; (e) DMSO or ethanol concentration of about 20% (v/v) to about 60% (v/v); (f) pH of about 4.0 to 8.0; and (g) temperature of about 10° C. to 60° C.

Exemplary reaction conditions include the assay conditions provided in Table 2 and Example 3. In carrying out the reaction described herein, the engineered aldolase polypeptide may be added to the reaction mixture in the partially purified or purified forms, whole cells transformed with the gene encoding the engineered aldolase polypeptide, and/or as cell extracts and/or lysates of such cells. Whole cells transformed with the gene encoding the engineered aldolase or cell extracts, lysates thereof, and isolated enzymes can be used in a wide variety of different forms, including solids (e.g., lyophilized, spray dried, or the like) or semisolid (e.g., a crude paste). The cell extract or cell lysate may be partially purified by precipitation (e.g., ammonium sulfate, polyethyleneimine, heat treatment or the like), followed by desalting procedures (e.g., ultrafiltration, dialysis, and the like) prior to lyophilization. Any of the enzyme preparations can be stabilized by crosslinking using known crosslinking agents, such as glutaraldehyde, or immobilization to a solid phase material (such as a resin).

In some embodiments of the reactions described herein, the reaction is performed under suitable reaction conditions described herein, wherein the engineered aldolase polypeptide is immobilized to a solid support. Solid supports useful for immobilizing the engineered aldolase enzyme for carrying out the reaction include but are not limited to beads or resins such as polymethacrylates with epoxy functional groups, polymethacrylates with amino epoxy functional groups, polymethacrylates, styrene/DVB copolymer or polymethacrylates with octadecyl functional groups. Exemplary solid supports include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, wherein an engineered polypeptide is expressed in the form of a secreted polypeptide, a culture medium containing the secreted polypeptide can be used in the process herein.

In some embodiments, the solid reactants (e.g., enzymes, salts, etc.) can be provided to the reaction in a variety of different forms, including powders (e.g., lyophilized, spray dried, etc.), solutions, emulsions, suspensions and the like. The reactants can be readily lyophilized or spray-dried using methods and instrumentation known to one skilled in the art. For example, the protein solution can be frozen at −80° C. in small aliquots, and then added to the pre-chilled lyophilization chamber, followed by the application of a vacuum.

In some embodiments, the order of addition of reactants is not critical. The reactants may be added together to the solvent at the same time (e.g., monophasic solvent, a biphasic aqueous co-solvent system, etc.), or alternatively, some reactants may be added separately, and some may be added together at different time points. For example, the cofactor, aldolase, and substrates may be added first to the solvent. For improved mixing efficiency when using aqueous co-solvent systems, aldolase and cofactors may be added and mixed into the aqueous phase first. The organic phase can then be added and mixed in, followed by addition of the substrates. Alternatively, the substrates can be premixed in the organic phase prior to addition to the aqueous phase.

Different features and embodiments of the present disclosure are exemplified in the following representative examples, which are intended to be illustrative and not restrictive.

EXAMPLES

The following examples further illustrate the present invention, but the present invention is not limited thereto. In the following examples, experimental methods with conditions not specified, were conducted at the commonly used conditions or according to the supplier's suggestion.

Example 1: Gene Cloning and Construction of Expression Vectors

The amino acid sequence of the wild-type aldolase from *Pseudomonas putida* can be retrieved from NCBI, and its coding nucleic acids were then synthesized by a vendor using conventional techniques in the art and cloned into the expression vector pACYC-Duet-1. The recombinant expression plasmid was transformed into *E. coli* BL21 (DE3) competent cells under the conditions of 42° C. and thermal shock for 90 seconds. The transformation solution was plated on LB agar plates containing chloramphenicol which was then incubated overnight at 37° C. Recombinant transformants were obtained.

Example 2: Recombinant Expression of Aldolase Polypeptides

The resulting transformant such as recombinant *E. coli* BL21 (DE3) from example 1 was inoculated into LB medium containing chloramphenicol (peptone 10 g/L, yeast extract 5 g/L, NaCl 10 g/L, pH 7.0) which was then cultured in a shaking incubator at 30° C., 250 rpm overnight. The overnight culture was subcultured into a 1 L flask containing 250 mL of TB medium (tryptone 12 g/L, yeast extract 24 g/L, glycerol 4 mL/L, PBS) at 30° C., 250 rpm in a shaking incubator. When the $OD_{600}$ of subculture broth reached 0.6~0.8, IPTG was added to induce the expression of recombinant aldolase at a final concentration of 0.1 mmol/L. After expression overnight, the culture was centrifuged to get resting cells. The pelleted resting cells were suspended in a pH 7.4 buffer, and then sonicated in an ice bath to get cell lysate. The supernatant of cell lysate was collected by centrifugation as a crude enzyme solution of the recombinant aldolase, and the supernatant was further freeze-dried using a lyophilizer to obtain crude enzyme powder.

According to the recombinant expression process using shaking flasks as mentioned above, a miniaturized expression process in 96-well plate was performed by proportionally reducing the scale. The crude enzyme solution was obtained through chemical lysis rather than ultrasonication.

Example 3: Reaction Conditions and Analytical Methods for Measuring Activity and Stereoselectivity of Aldolase Polypeptides 4-(methylsulfonyl)benzaldehyde was added at a final concentration of 10 g/L in a 96-well plate, where 4-(methylsulfonyl)benzaldehyde was dissolved in dimethyl sulfoxide (DMSO) prior to its addition. The final concentration of DMSO in the system was 10% (v/v), while glycine was added at 10 times the molar amount of 4-(methylsulfonyl)benzaldehyde (i.e., 40.75/L), and pyridoxal phosphate (PLP) was added at the final concentration of 0.05 mmol/L; and finally the crude enzyme solution was added. The total volume of the reaction was 200 μl. After the reaction was run for 4 hours, the reaction was quenched with 50% acetonitrile to inactivate aldolase polypeptides. The quenched reaction was centrifuged and resulting supernatant was diluted and then subjected to HPLC analysis to determine the substrate conversion and the de value for product A2.

Enzymatic reaction was scaled up to 5 mL of total reaction volume on the basis of the above 96-well microplate reaction. The loading of 4-(methylsulfonyl)benzaldehyde was 30 g/L, the loading of glycine was 123 g/L, the final concentration of PLP was 0.05 mmol/L, the final concentration of DMSO in the system was 10% (v/v), and enzyme powder loading was 5 g/L. The reaction was carried out for 24 hours, during which time sampling was carried out. After inactivation of reaction samples with 50% acetonitrile, the supernatant of quenched reaction samples was taken to analyze the conversion and the de value during the reaction.

The analytical method: the quenched reaction solution was centrifuged and the supernatant was diluted with 50% acetonitrile to a product concentration of less than 1 g/L. 10 μl of this diluted sample was injected into an Agilent 1260 HPLC to analyze the conversion. The column was Phenomenex Chirex 3126 (D)-penicillamine 150*4.6 mm, mobile phase was 3 mM copper sulfate:methanol=85:15, at a flow rate of 1 mL per minute, at a column temperature of 50° C., and the detection wavelength was 235 nm. The retention time of (2S,3R)-2-amino-3-hydroxy-3-[4-(methylsulfonyl) phenyl] propanoic acid was 7.476 min; the retention time of (2R,3R)-2-amino-3-hydroxy-3-[4-(methylsulfonyl)phenyl] propanoic acid was 7.915 minutes; the retention time of 4-(methylsulfonyl)benzaldehyde was 9.069 minutes; the retention time of (2S,3S)-2-amino-3-hydroxy-3-[4-(methylsulfonyl)phenyl] propanoic acid was 14.573 minutes; the retention time of (2R,3S)-2-amino-3-hydroxy-3-[4-(methylsulfonyl)phenyl] propanoic acid was 15.008 minutes. The total analysis time was 20 minutes.

Example 4: Construction of Aldolase Mutant Library

Quikchange kit (supplier: Agilent) was preferably used here. The sequence design of the mutagenesis primers was performed according to the instructions of the kit. The PCR system consisted of 10 µl of 5× Buffer, 1 µl of 10 mM dNTP, 1 µl of plasmid DNA template (50 ng/µl), 0.75 µl (10 uM) each of the upstream and downstream primers, 0.5 µl of high fidelity enzyme and 36 µl of ddH2O, The PCR primer has a NNK codon at the mutation position.

PCR amplification steps: (1) 98° C., pre-denaturation 3 min; (2) 98° C. denaturation 10 s; (3) annealing and extension 3 min at 72° C.; steps of (2)~(3) repeated 25 times; (5) extension 10 min at 72° C.; (6) cooling to 4° C. 2 µl of DpnI was added to the PCR product and the plasmid template was eliminated by overnight digestion at 37° C. The digested PCR product was transformed into E. coli BL21 (DE3) competent cells and plated on LB agar plates containing chloramphenicol to obtain a site-saturation mutagenesis library.

Example 5: High-Throughput Screening of Aldolase Mutant Libraries

Mutant colonies were picked from the LB agar plates, inoculated into 200 µl of LB medium (containing chloramphenicol) in a 96-well shallow plate and cultured overnight at 30° C. 20 µl of the above culture was used to inoculate 400 µl of TB medium (including chloramphenicol) in a deep-well plate. When $OD_{600}$ of deep-well culture reached 0.6~0.8, and IPTG was added to induce expression at a final concentration of 1 mM, and the expression undertook at 30° C. overnight. Once the overnight expression was done, the culture was centrifuged at 4000 rpm for 10 minutes to obtain cell pellets to which 200 µl of a chemical lysis reagent (1 g/L lysozyme, 0.5 g/L PMBS) was added to break the cells. Then cell lysate was centrifuged at 4000 rpm for 10 minutes, and subsequently 60 µl of supernatant per well were transferred into a deep well plate containing the reaction solution described in Example 3. The reaction was shaken at 20~40° C. for desired time, and finally quenched with 50% acetonitrile. Samples were taken for analysis.

Example 6: Fermentation Process for the Expression of Engineered Aldolase

A single microbial colony of E. coli containing a plasmid bearing the target aldolase gene was inoculated into a 50 mL LB broth containing 30 µg/mL chloramphenicol (5.0 g/L Yeast Extract, 10 g/L Tryptone, 10 g/L sodium chloride). Cells were incubated overnight (at least 16 hours) with shaking at 250 rpm in a 30° C. shaker. When the OD600 of the culture reached 1.6 to 2.2, the culture was used to inoculate medium in fermentor.

A 5 L fermentor containing 2.0 L of growth medium was sterilized in a 121° C. autoclave for 30 minutes. The fermentor was inoculated with the abovementioned culture. Temperature of fermentor was maintained at 37° C. The growth medium in fermentor was agitated at 200-800 rpm and air was supplied to the fermentation vessel at 2-8 L/min to maintain the dissolved oxygen level at 30% saturation or greater. The culture was maintained at pH 7.0 by addition of 25-28% v/v ammonium hydroxide. Cell growth was maintained by feeding a feed solution containing 500 g/L of dextrose glucose monohydrate, 12 g/L ammonium chloride, and 5 g/L magnesium sulfate heptahydrate. After the $OD_{600}$ of culture reached 25±5, the temperature of fermentor was decreased and maintained at 30° C., and the expression of aldolase polypeptides was induced by the addition of isopropyl-β-D-thiogalactopyranoside (IPTG) to a final concentration of 1 mM. Fermentation process then continued for additional 18 hours. After the fermentation process was complete, cells were harvested using a Thermo Multifuge X3R centrifuge at 8000 rpm for 10 minutes at 4° C. Harvested cells were used directly in the downstream recovery process or stored frozen at −20° C.

6 g of cell pellet was resuspended in 30 mL of 100 mM potassium phosphate buffer containing 250 µM pyridoxal 5'-phosphate (PLP), pH 7.5 at 4° C. The cells were then homogenized into cell lysate using a homogenizer. The cell lysate was clarified using a Thermo Multifuge X3R centrifuge at 8000 rpm for 10 minutes at 4° C. The clarified supernatant was dispensed into a shallow container, frozen at −20° C. and lyophilized to enzyme powder. The aldolase enzyme powder was stored frozen at −20° C.

Example 7: Asymmetric Synthesis of (2S,3R)-2-amino-3-hydroxy-3-[4-(methylsulfonyl)phenyl] Propanoic Acid from Aldehydes and Amino Acids Catalyzed by Aldolase Polypeptides Taking a total volume of 1.0 L as an example, the following items were added to the reaction vessel: 123 g of glycine, 30 g of 4-(methylsulfonyl)benzaldehyde, 958 mL of a 30% (v/v) aqueous methanol solution, 3 g of enzyme powder of SEQ ID NO: 158, 5 mL of PLP stock solution (10 mM). The reaction temperature was set at 30° C. and the stirring speed was 400 rpm. After 6 hours of reaction, the total conversion of the substrate was ≥65% and de ≥90% for the product A2.

Example 8: Asymmetric Synthesis of (2S,3R)-2-amino-3-hydroxy-3-(4-nitrophenyl) Propanoic Acid from Aldehydes and Amino Acids Catalyzed by Aldolase Polypeptides

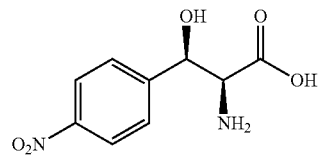 [SMILES: N[C@H](C(=O)O)[C@H](O)c1ccc([N+](=O)[O-])cc1]

Taking a total volume of 1.0 L as an example, the following items were added to the reaction vessel: 178 g of glycine, 30 g of p-nitrobenzaldehyde, 942 mL of a 40% (v/v) aqueous ethanol solution, 4 g of enzyme powder of SEQ ID NO: 120, 5 mL of PLP stock solution (10 mM). The reaction temperature was set at 35° C. and the stirring speed was 400 rpm. After 6 hours of reaction, the total conversion of the substrate was ≥10% and de ≥95% for the product (2S,3R)-2-amino-3-hydroxy-3-(4-nitrophenyl) propanoic acid.

Example 9: Asymmetric Synthesis of (2S,3R)-2-amino-3-(3,4-dihydroxybenzene)-3-hydroxypropionic Acid from Aldehydes and Amino Acids Catalyzed by Aldolase Polypeptides

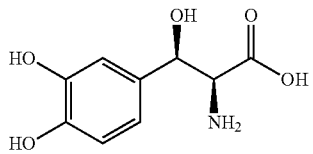 [SMILES: N[C@H](C(=O)O)[C@H](O)c1ccc(O)c(O)c1]

Taking a total volume of 1.0 L as an example, the following items were added to the reaction vessel: 55 g of glycine, 10 g of 3,4-dihydroxybenzaldehyde, 960 mL of deionized water, 10 g of enzyme powder of SEQ ID NO: 86, 5 mL of PLP stock solution (10 mM). The reaction temperature was set at 30° C. and the stirring speed was 400 rpm. After 2 hours of reaction, the total conversion of the substrate was ≥30%.

It should be understood that after reading the above contents of the present invention, those skilled in the art may make various modifications or changes to the present invention. And these equivalent forms also fall within the scope of the appended claims of the present invention.

The invention claimed is:

1. An engineered aldolase polypeptide that condenses 4-(methylsulfonyl)benzaldehyde with glycine to produce (2S,3R)-2-amino-3-hydroxy-3-[4-(methylsulfonyl)phenyl] propanoic acid, said polypeptide comprising an amino acid sequence having a D16E substitution as compared to SEQ ID NO: 2 or SEQ ID NO: 4, further wherein the amino acid of said engineered aldolase polypeptide is selected from the group consisting of SEQ ID NOs: 86, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 196, 198, 200, 208, 210, 212, 214, 216.

2. The aldolase polypeptide of claim 1, wherein said engineered aldolase polypeptide condenses 4-(methylsulfonyl)benzaldehyde with glycine to produce (2S,3R)-2-amino-3-hydroxy-3-[4-(methylsulfonyl)phenyl] propanoic acid in a diastereomeric excess of at least 60% under suitable reaction conditions that include about 30 g/L 4-(methylsulfonyl) benzaldehyde, about 123 g/L glycine, about 50 µM pyridoxal 5'-phosphate (PLP), and about 20% (v/v) DMSO, at about 30° C.

3. An engineered aldolase polypeptide, which is a polypeptide of (a) or (b) below:
   (a) a polypeptide comprising an amino acid sequence selected from the group consisting of SEQ ID NOs: 86, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 196, 198, 200, 202, 204, 206, 208, 210, 212, 214, and 216; or
   (b) a polypeptide comprising an amino acid sequence having (i) at least 85% sequence identity to one of the amino acid sequences recited in (a), and (ii) a D16E amino acid substitution relative to said one amino acid sequence recited in (a); wherein said polypeptide comprises aldolase activity.

4. A polypeptide immobilized on a solid material by a chemical bond or a physical adsorption method, wherein the polypeptide comprises the engineered aldolase polypeptide according to claim 1.

5. An aldolase catalyst obtained by culturing host cells, each of which carries an expression vector comprising a polynucleotide encoding the engineered aldolase polypeptide of claim 1, wherein said aldolase catalyst comprises cells or culture fluid containing the aldolase polypeptides, or an article processed therewith, further wherein the article refers to an extract obtained from the culture of transformant cell, an isolated product obtained by isolating or purifying an aldolase from the extract, or an immobilized product obtained by immobilizing transformant cell, an extract thereof, or isolated product of the extract.

6. A process of preparing a β-hydroxy-α-amino acid of formula (I):

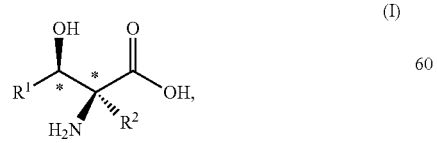
(I)

wherein the β-hydroxy-α-amino acid of formula (I) has the indicated stereochemical configuration at the chiral center marked with an *;

further wherein:
R¹ is selected from among optionally substituted or unsubstituted aryl, optionally substituted or unsubstituted heteroaryl, and optionally substituted or unsubstituted C1-C8 hydrocarbyl;
R² is selected from among —H, —CH₂OH, —CH₂SH, —CH₂SCH₃, and optionally substituted or unsubstituted C₁-C₄ hydrocarbyl;
wherein the process comprises the steps of:
(a) contacting an aldehyde substrate of formula (II) and an amino acid substrate of formula (III):

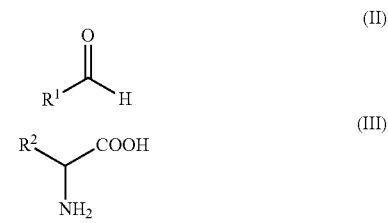

with the engineered polypeptide of claim 1, under suitable reaction conditions; and
(b) producing the β-hydroxy-α-amino acid of formula (I), wherein the β-hydroxy-α-amino acid of formula (I) is obtained in diastereomeric excess.

7. The process of claim 6, wherein the β-hydroxy-α-amino acid of formula (I) is:

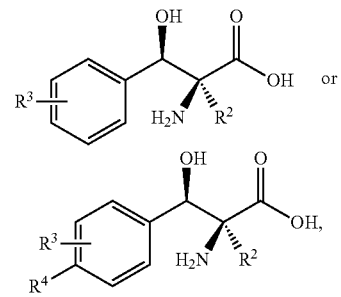

further wherein:
R² is —H, —CH₃, —CH₂CH₃, —CH(CH₃)₂, —CH₂OH, —CH₂SH or —CH₂SCH₃;
R³ is C₁-C₄ hydrocarbyl, —H, a halogen selected from among —F, —Cl, —Br and —I, —NO₂, —NO, —SO2R', —SOR', —SR', —NR'R', —OR', —CO₂R', —COR', —C(O)NR', —SO₂NH₂, —SONH₂, —CN, or —CF₃, wherein each R' is independently selected from —H or (C₁-C₄) hydrocarbyl;
R³ can also be

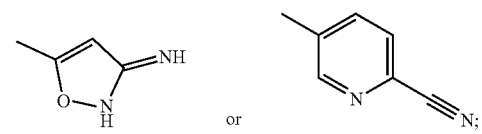

R⁴ is a C₁-C₄ hydrocarbyl, —H, a halogen selected from among —F, —Cl, —Br and —I, —NO₂, —NO, —SO₂R, —SOR, —SR', —NR'R', —OR', —CO₂R', —COR', —C(O)NR', —SO₂NH₂, —SONH₂, —CN, or —CF₃, wherein each R' is independently selected From —H or (C₁-C₄) hydrocarbyl;
and the aldehyde substrate of formula (II) is:

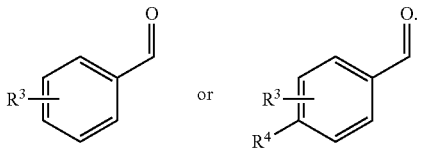

8. The process of claim 7, wherein R³ is:
in the para position of the phenyl ring;
in the meta position of the phenyl ring;
in the ortho position of the phenyl ring;
in the both para position and the meta position of the phenyl ring;
in both the para position and the ortho position of the phenyl ring; or
in both the meta position and the ortho position of the phenyl ring.

9. The process of claim 6, wherein the β-hydroxy-α-amino acid of formula (I) is selected from among:

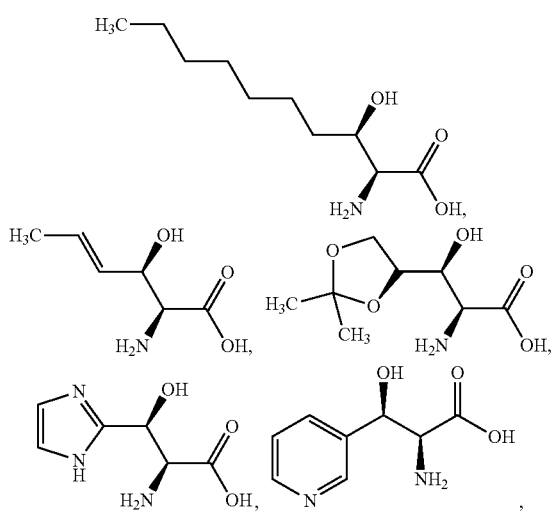

-continued

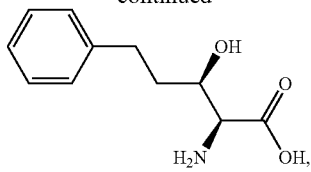

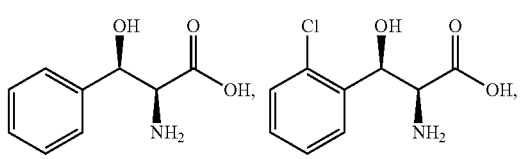

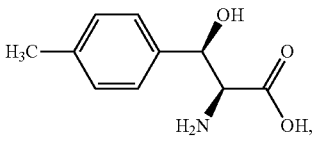

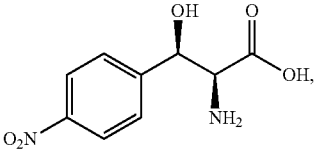

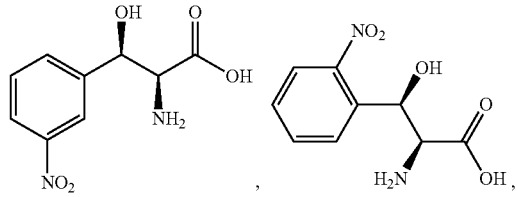

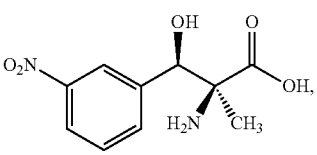

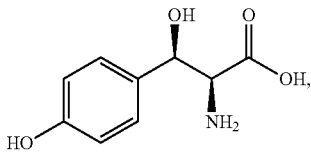

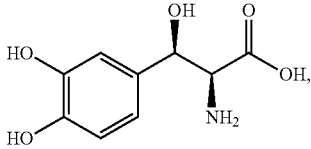

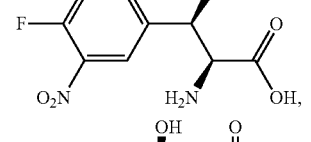

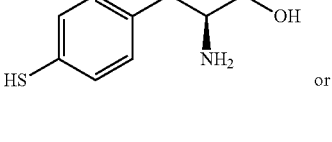

or

-continued

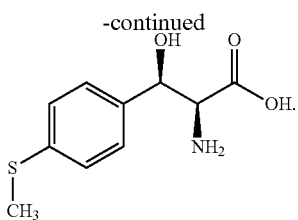

10. A process for preparing a compound of formula A2:

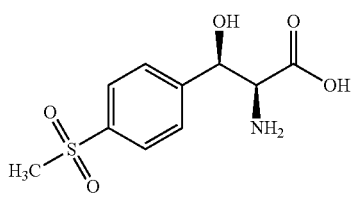

wherein the process comprises the steps of:
(a) contacting a compound of formula A1

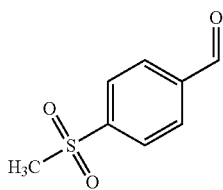

with the engineered aldolase polypeptide of claim 1 in a suitable solvent and in the presence of glycine, under suitable reaction conditions; and
(b) converting the compound of formula A1 to the compound of formula A2.

11. The process of claim 6, wherein the β-hydroxy-α-amino acid product is present in diastereomeric excess of at least 60%.

12. The process of claim 6, wherein the reaction is carried out in a solvent comprising water, methanol, ethanol, propanol, isopropanol, isopropyl acetate, dimethylsulfoxide (DMSO) or dimethylformamide (DMF).

13. The process of claim 6, wherein the reaction conditions include a temperature of 10° C. to 60° C.

14. The process of claim 6, wherein the reaction conditions include pH 4.0 to pH 8.0.

15. The process of claim 6, wherein the aldehyde substrate is present at a loading of 5 g/L to 200 g/L.

16. The engineered aldolase polypeptide of claim 2, wherein said (2S, 3R)-2-amino-3-hydroxy-3-[4-(methylsulfonyl)phenyl] propanoic acid is produced in a diastereomeric excess of at least 80%.

17. The engineered aldolase polypeptide of claim 2, wherein said (2S, 3R)-2-amino-3-hydroxy-3-[4-(methylsulfonyl)phenyl] propanoic acid is produced in a diastereomeric excess of 95% or more.

18. An aldolase catalyst obtained by (i) culturing a host cell that carries an expression vector comprising a polynucleotide encoding the engineered aldolase polypeptide of claim 1 and (ii) obtaining an aldolase polypeptide from the culture, wherein said aldolase catalyst comprises cells or culture fluid containing the aldolase polypeptides, or an article processed therewith, further wherein the article refers to an extract obtained from the culture of transformant cell, an isolated product obtained by isolating or purifying an aldolase from the extract, or an immobilized product obtained by immobilizing transformant cell, an extract thereof, or isolated product of the extract.

19. The engineered aldolase polypeptide according to claim 3, wherein said polypeptide comprises an amino acid sequence having (i) at least 90% sequence identity to one of the amino acid sequences recited in (a), and (ii) a D16E amino acid substitution relative to said one amino acid sequence recited in (a); wherein said polypeptide comprises aldolase activity.

20. The engineered aldolase polypeptide according to claim 3, wherein said polypeptide comprises an amino acid sequence having (i) at least 95% sequence identity to one of the amino acid sequences recited in (a), and (ii) a D16E amino acid substitution relative to said one amino acid sequence recited in (a); wherein said polypeptide comprises aldolase activity.

* * * * *

UNITED STATES PATENT AND TRADEMARK OFFICE
CERTIFICATE OF CORRECTION

PATENT NO. : 11,274,287 B2
APPLICATION NO. : 16/616370
DATED : March 15, 2022
INVENTOR(S) : Haibin Chen et al.

It is certified that error appears in the above-identified patent and that said Letters Patent is hereby corrected as shown below:

In the Specification

At Column 3, Line 63, replace the term "118W" with the term -- I18W --.

At Column 3, Line 65, replace the term "1106N" with the term -- I106N --.

At Column 3, Line 66, replace the term "R1515" with the term -- R151S --.

At Column 3, Line 66, replace the term "T1595" with the term -- T159S --.

At Column 3, Line 66, replace the term "M1981" with the term -- M198I --.

At Column 4, Line 23, replace the term "118W" with the term -- I18W --.

At Column 4, Line 27, replace the term "T140s" with the term -- IT140S --.

At Column 4, Line 27, replace the term "M1791" with the term -- M179I --.

At Column 4, Line 30, replace the term "Y3181" with the term -- Y318I --.

Signed and Sealed this
Fourteenth Day of February, 2023

Katherine Kelly Vidal
*Director of the United States Patent and Trademark Office*